(12) United States Patent
Blair et al.

(10) Patent No.: US 9,385,668 B2
(45) Date of Patent: Jul. 5, 2016

(54) CABLELESS HIGH POWER RF/MICROWAVE POWER AMPLIFIER WITH MULTIPLE POWER AMPLIFIER UNITS

(71) Applicant: DAICO INDUSTRIES, INC., Carson, CA (US)

(72) Inventors: Eddie Blair, Huntington Beach, CA (US); Ruben X. Mao, Irvine, CA (US); Scott Honma, Carson, CA (US)

(73) Assignee: DAICO INDUSTRIES, INC., Carson, CA (US)

( * ) Notice: Subject to any disclaimer, the term of this patent is extended or adjusted under 35 U.S.C. 154(b) by 0 days.

(21) Appl. No.: 14/691,449

(22) Filed: Apr. 20, 2015

(65) Prior Publication Data

US 2016/0112019 A1    Apr. 21, 2016

Related U.S. Application Data

(60) Provisional application No. 62/065,390, filed on Oct. 17, 2014, provisional application No. 62/096,811, filed on Dec. 24, 2014.

(51) Int. Cl.
*H03F 3/68* (2006.01)
*H03F 3/19* (2006.01)
(Continued)

(52) U.S. Cl.
CPC ............... *H03F 3/19* (2013.01); *H03F 1/0205* (2013.01); *H03F 3/211* (2013.01); *H03F 3/68* (2013.01); *H03F 2200/451* (2013.01); *H03F 2203/21142* (2013.01)

(58) Field of Classification Search
CPC ......... H03F 3/211; H03F 3/602; H03F 3/604; H03F 3/72; H03F 1/0288; H03F 3/24; H03F 2200/451; H03F 1/0277; H03G 1/0088

USPC .............................................. 330/124 R, 295
See application file for complete search history.

(56) References Cited

U.S. PATENT DOCUMENTS 4,160,960 A    7/1979  Bikker
5,008,633 A    4/1991  Hom
(Continued)

FOREIGN PATENT DOCUMENTS

WO    WO2016/060781 A1    4/2016

OTHER PUBLICATIONS

U.S. Appl. No. 14/691,413, filed Apr. 20, 2015, entitled "Combined High Power RF/Microwave Amplifier With Multiple Power Amplifier Units and Automatic Failure Protection."
(Continued)

*Primary Examiner* — Khanh V Nguyen
(74) *Attorney, Agent, or Firm* — McDermott Will & Emery LLP

(57) ABSTRACT

A cableless high power RF or microwave amplifier may amplifies an RF or microwave signal. The amplifier may include: an input signal divider (DIV) that has a DIV input connector that receives the RF or microwave signal and that divides this input signal into multiple sub-input signals, each of which is delivered to a DIV output connector; multiple power amplifier units (PAUs), each of which has a PAU input connector that receives an RF or microwave signal and a PAU output connector that delivers an amplified version of the received RF or microwave signal; and an output signal switching combiner unit (SCU) that has multiple SCU input connectors and that coherently sums the signals at the multiple SCU input connectors and delivers this to an SCU output connector. Each of the PAU output connectors may be electrically connected to a different one of the SCU input connectors without connecting cables.

14 Claims, 47 Drawing Sheets

(51) Int. Cl.
*H03F 1/02* (2006.01)
*H03F 3/21* (2006.01)

(56) References Cited

U.S. PATENT DOCUMENTS

| | | | |
|---|---|---|---|
| 5,256,987 A * | 10/1993 | Kibayashi et al. | 330/295 |
| 5,467,063 A | 11/1995 | Burns et al. | |
| 5,986,500 A * | 11/1999 | Park et al. | 330/51 |
| 6,323,742 B1 | 11/2001 | Ke | |
| 6,463,269 B2 | 10/2002 | DeMarco | |
| 6,798,314 B2 | 9/2004 | Nation | |
| 6,844,793 B2 | 1/2005 | Kenington | |
| 7,046,101 B2 | 5/2006 | Mruz et al. | |
| 7,123,114 B2 | 10/2006 | Yoon et al. | |
| 7,298,206 B2 * | 11/2007 | Pickerd et al. | 330/124 R |
| 7,327,996 B2 | 2/2008 | Chen et al. | |
| 7,514,994 B2 | 4/2009 | Fraysse | |
| 7,589,588 B2 | 9/2009 | Ohnishi et al. | |
| 8,189,338 B2 | 5/2012 | Turner | |
| 8,710,927 B2 | 4/2014 | Kamitani et al. | |
| 8,723,618 B2 | 5/2014 | Hirota et al. | |
| 2003/0001668 A1 | 1/2003 | Mruz et al. | |
| 2005/0174194 A1 | 8/2005 | Wu et al. | |
| 2009/0295473 A1 | 12/2009 | Dupuy et al. | |
| 2011/0149526 A1 | 6/2011 | Turner | |
| 2012/0274414 A1 | 11/2012 | Hung et al. | |
| 2013/0093534 A1 | 4/2013 | Mei | |
| 2016/0112013 A1 | 4/2016 | Mao et al. | |
| 2016/0112020 A1 | 4/2016 | Blair et al. | |
| 2016/0112021 A1 | 4/2016 | Blair et al. | |
| 2016/0112027 A1 | 4/2016 | Blair et al. | |

OTHER PUBLICATIONS

U.S. Appl. No. 14/691,422, filed Apr. 20, 2015, entitled "RF/Microwave High Power Switching Combiner Unit."

U.S. Appl. No. 14/971,427, filed Apr. 20, 2015, entitled "T-Shaped Power Amplifier Cooling Plate."

U.S. Appl. No. 14/691,430, filed Apr. 20, 2015, entitled "RF/Microwave Power Divider With Port to Port Isolation."

U.S. Appl. No. 14/691,454, filed Apr. 20, 2015, entitled "Combined RF/Microwave Amplifiers With Individual Power Supplies."

PCT Application No. PCT/US2015/050748, filed Sep. 17, 2015, entitled "High Power RF/Mircowave Amplifier Having Multiple Amplifier Units and Automatic Failure Protection, Switching Combiner Unit, T-Shaped Amplifier Cooling Plate, Power Divider With Port-To-Port Issolation, Cableless Connections, and Individiual Power Supplies."

USPTO. 2015. Non-final Office Action issued Dec. 17, 2015, for U.S. Appl. No. 14/691,413.

USPTO. 2016. Non-final Office Action issued Jan. 15, 2015 for U.S. Appl. No. 14/691,430.

ISA/US. 2016. International Search Report and Written Opinion of the International Searching Authority for PCT Application PCT/US2015/050748, dated Jan. 28, 2016.

USPTO. 2016. Non-final Office Action issued Mar. 17, 2016, for U.S. Appl. No. 14/691,422, filed Apr. 20, 2015, entitled "RF/Microwave High Power Switching Combiner Unit,".

USPTO. 2016. Non-final Office Action issued Mar. 22, 2016, for U.S. Appl. No. 14/691,413, filed Apr. 20, 2015, entitled "Combined High Power RF/Microwave Amplifier With Multiple Power Amplifier Units and Automatic Failure Protection,".

USPTO. 2016. Non-final Office Action dated Apr. 21, 2016 for U.S. Appl. No. 14/691,430, filed Apr. 20, 2015, entitled "RF/Microwave Power Divider with Port to Port Isolation," published Apr. 21, 2016 as US-2016-0112027-A1.

USPTO. 2016. Non-final Office Action dated May 16, 2016, for U.S. Appl. No. 14/691,427, filed Apr. 20, 2015, entitled "T-Shaped Power Amplifier Cooling Plate," published Apr. 21, 2016 as US-2016-0112013-A1.

\* cited by examiner

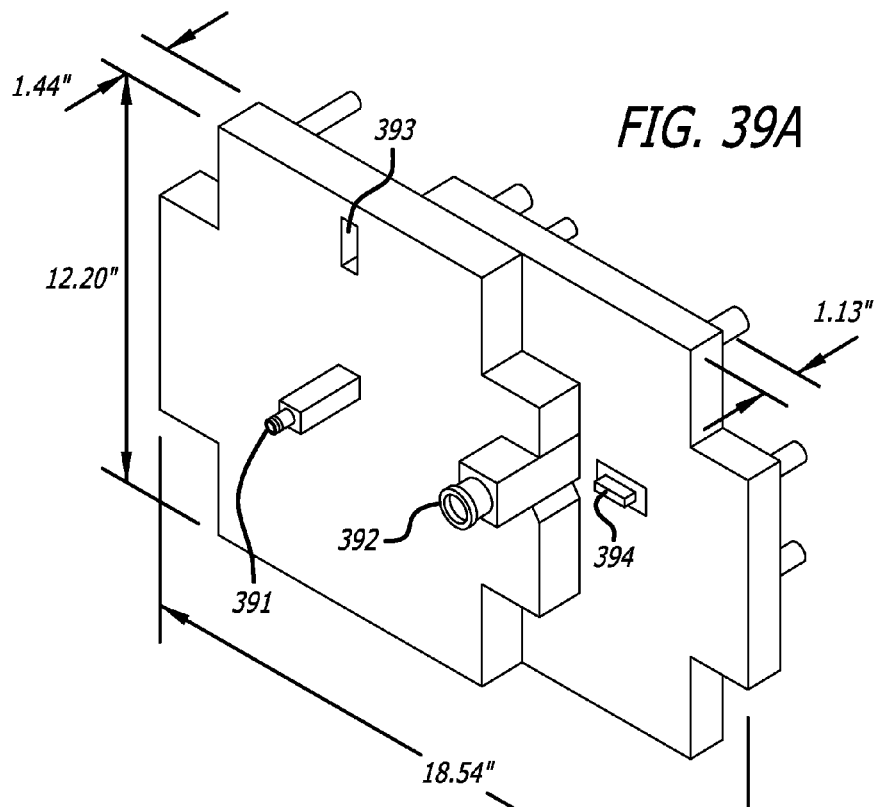
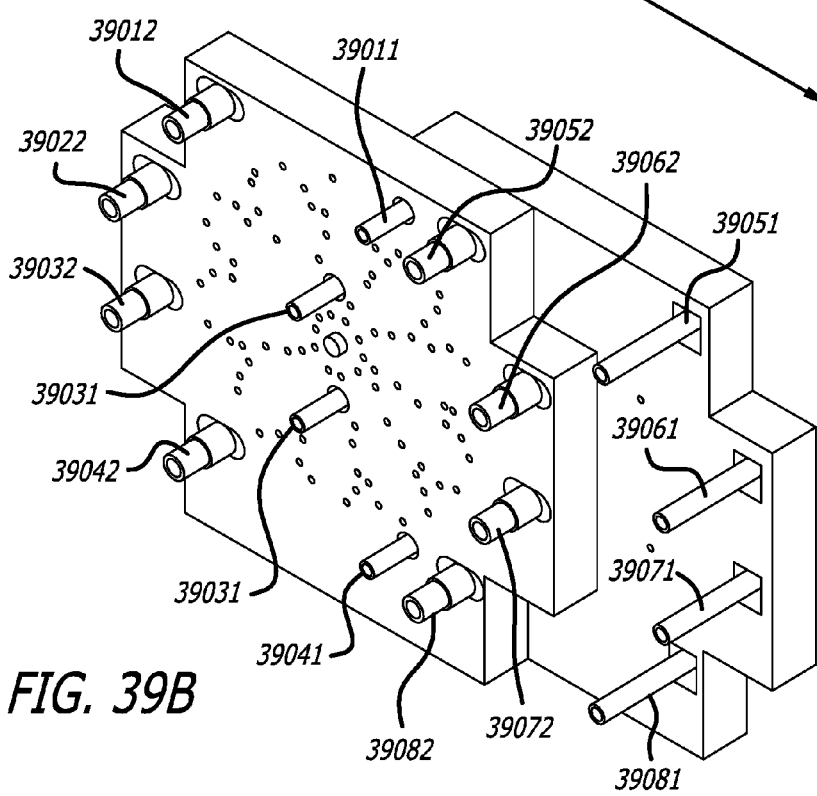

CABLELESS HIGH POWER RF/MICROWAVE POWER AMPLIFIER WITH MULTIPLE POWER AMPLIFIER UNITS

CROSS-REFERENCE TO RELATED APPLICATIONS

This application is based upon and claims priority to U.S. provisional patent application 62/065,390, entitled "HIGH POWER DENSITY RF/MICROWAVE SOLID STATE POWER AMPLIFIER ARCHITECTURE," filed Oct. 17, 2014, and U.S. provisional patent application 62/096,811, entitled "ULTRA HIGH POWER SOLID STATE (M+N) REDUNDANT CHPA ARCHITECTURE," filed Dec. 24, 2014. The entire content of both of these applications is incorporated herein by reference.

BACKGROUND

1. Technical Field

This disclosure relates to high power, solid state amplifiers for radio frequency and microwave signals, including pulse and CW radar signals.

2. Description of Related Art

RF and microwave power amplifiers may need to operate under pulsed conditions, such as in civilian and military radar systems. They may need to provide a high peak power to gain surveillance/transmit distance capacity.

Klystron and TWT systems may deliver very high transmit power (megawatts), while occupying relatively small physical volumes. However, these radar systems may provide a mean time between failures (MTBF) of only hundreds of hours. This can be problematic in mission-critical applications, such as in radar on a military ship or in an airport control tower.

Solid state power devices are now capable of delivering 1 kW peak power per device or more. Efforts have been made to achieve solid state high power (>>10 kW) amplifiers (SSH-PAs) by combining multiple solid state power devices utilizing multiple stage, conventional passive combining schemes, such as balun, Wilkinson, hybrid, and radial combiners. However, the power level and power density of SSHPAs may not be as great as the rival Klystron.

Reliability can also be a problem. The MTBF of a power amplifier unit (PAU) that includes one or more power devices may be the replica of the failure rate $\lambda_{PAU}$ (per $10^6$ hours) where the power device failure rate $\lambda_p$ dominates the total $\lambda_{PAU}$. According to MIL-HBK-217:

$$\lambda_p = \lambda_b \pi_T \pi_A \pi_M \pi_Q \pi_E \quad (1)$$

where $\pi_T$, $\pi_A$, $\pi_M$, $\pi_Q$, and $\pi_E$ are as specified below.

The temperature factor may depend on the junction temperature $T_J$ of a power device ($\pi_T = 0.1$ with $T_J = 100°$ C.) as follows:

$$\pi_T = 0.1 e^{\{-2903(1/(TJ+273)-1/373)\}} \quad (2)$$

Application factor may be irrelevant to the specific power device ($\pi_A = 0.64$ with 4% duty cycle as an example):

$$\pi_A = 0.06(\text{Duty Cycle \%}) + 0.4 \quad (3)$$

Matching factor: $\pi_M = 1.0$ for the Input and Output match device
Quality factor: $\pi_Q = 5.0$ for Lower Part
Environmental factor: $\pi_E = 4.0$ for naval sheltered NS as an example For a power device used in a naval-sheltered environment, assuming 100° C. peak junction temperature with ~4% duty cycle pulse operation:

$$\lambda_p = 1.28 \lambda_b \quad (4)$$

where the $\lambda_b$ base failure rate may be determined by operating frequency F in GHz and peak power P in watts:

$$\lambda_b = 0.032 e^{\{0.354(F)+0.00558(P)\}} \quad (5)$$

Assuming an operating frequency F=1.0 GHz, the following Table 1 presents estimated MTBF of SSHPA utilizing conventional combining architecture with various power levels per device.

Assuming an operating frequency F=1.0 GHz, the following Table 1 presents estimated MTBF of SSHPA utilizing conventional combining architecture with various power levels per device.

TABLE 1

Estimated MTBF of Conventionally Combining SSHPA

| Power Device Conventionally Combined to form HPA | | | Estimated MTBF (Hr) for HPA* including power devices and passive components | | | |
|---|---|---|---|---|---|---|
| Peak Power (W) | λp (per 106 Hr) | MTBF (Hr) | 5 kW | 10 kW | 20 kW | 40 kW |
| 500 | 0.74 | 1,350 kHr | 75 kHr | 37.5 kHr | 18.75 kHr | 9.375 kHr |
| 1000 | 12.08 | 82.7 kHr | 9.2 kHr | 4.6 kHr | 2.3 kHr | 1.15 kHr |
| 2000 | 3203.44 | 310 Hr | 69 Hr | 35 Hr | 17.5 Hr | 8.75 Hr |

*The estimation is based on 1.5 times total power device failure rate, as the overall failure rate of SSHPA. The actual MTBF of SSHPA may vary depending upon specific applications, environments, etc.

Thus, further increasing device unit power may not reliably achieve a needed high power. With moderate unit power, the reliability of power under 10 kW may be feasible based on conventional combining architecture. However, it may not be sufficiently reliable for power levels greater than 100 kW. The use of lower power devices in HPA may also create mechanical complications and may not have a needed power density.

This analysis may apply for ultra-long pulse, ultra-high duty cycle, and CW operation power amplifiers with lower output power, because significant junction temperature increases may dramatically decrease the reliability of HPA according to equations 2 and 3.

In general, RF and microwave SSHPAs utilizing conventional combining architecture summing up multiple solid state power devices can face ultra-high power and ultra-high power density challenges in comparison to rival technologies due to limitations in power device availability and/or reliability.

Therefore, the need continues for an RF or microwave amplifier that can handle ultra-high power in excess of 10 kW with high power density and/or ultra-reliability for various signaling applications, including pulsed and continuous wave (CW) operations.

SUMMARY

A cableless high power RF or microwave amplifier may amplifies an RF or microwave signal. The amplifier may include: an input signal divider (DIV) that has a DIV input connector that receives the RF or microwave signal and that divides this input signal into multiple sub-input signals, each of which is delivered to a DIV output connector; multiple power amplifier units (PAUs), each of which has a PAU input connector that receives an RF or microwave signal and a PAU output connector that delivers an amplified version of the received RF or microwave signal; and an output signal switching combiner unit (SCU) that has multiple SCU input connectors and that coherently sums the signals at the multiple SCU input connectors and delivers this to an SCU output connector. Each of the PAU output connectors may be electrically connected to a different one of the SCU input connectors without connecting cables.

Each of the PAU output connectors and each of the SCU input connectors may be blind mate connectors.

Each of the DIV output connectors may be connected to a different one of the PAU input connectors without connecting cables.

Each of the DIV output connectors and each of the PAU input connectors may be blind mate connectors.

The PAU input connector and the PAU output connector of each PAU may both lie within the same plane.

All of the DIV output connectors may lie within the same plane.

All of the SCU input connectors may lie within the same plane.

All of the DIV output connectors and all of the SCU input connectors may lie in the same plane.

All of the DIV output connectors may be equidistant from a central point.

All of the SCU input connectors may be equidistant from a central point.

All of the DIV output connectors may be equidistant from a central point that is at a different location than the central point from which all of the SCU input connectors are equidistant.

The DIV and SCU may be in a common housing.

The cableless high power RF or microwave amplifier may include, for each PAU: an electronic switch between the DIV output connector that is connected to the PAU and the PAU input connector to which the DIV output connector is connected; and a sense switch that causes the electronic switch to open when the PAU is removed from the high power RF or microwave amplifier, but before any electrical connection to the PAU is broken.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 29A illustrates a CHPA module; FIG. 29B illustrates a PSB module; FIG. 29C illustrates an IDD module with PSUs; FIG. 29D illustrates an ICU module located in an IDDM; and FIG. 29E illustrates a 4-way OCM with an output coupler.

FIGS. 39A and 39B illustrate an example of a consolidated (7+1)DSCU which may have a significant proportional profile reduction in comparison to the (9+1)DIV/SCU shown in FIG. 33 and which may be assembled with matched cables.

DETAILED DESCRIPTION OF ILLUSTRATIVE EMBODIMENTS

Figure 1:
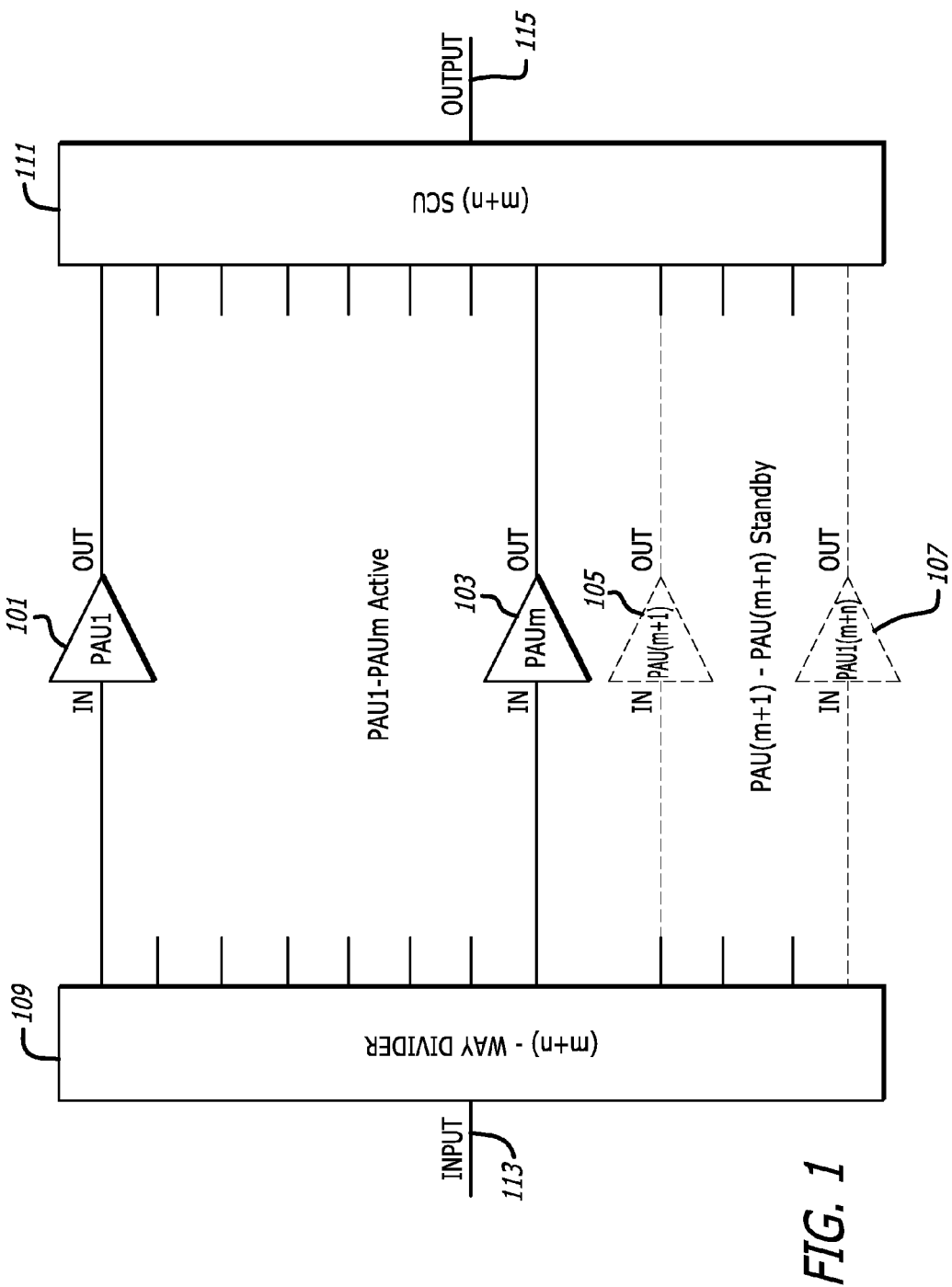
FIG. 1 is a simplified block diagram of an example of a redundant, combined high power amplifier (CHPA) architecture.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The following abbreviations are used in this disclosure:
Ao Operation availability
BAM Basic amplifier module
OAF Canadian Air Force
COM Combiner
CHPA Combined high power amplifier
DAU Driver amplifier unit
DIV Divider
DSCU Divider switching combiner unit
HPA High power amplifier
ICU Interface control unit
ICM Interface control module
IDD Input driver divider
IDDM Input Driver and Divider Module
LRU Line replaceable units
m Normally online LRUs
n Normally standby LRUs
MTBCF Mean time between critical failures
MTBF Mean time between failures
OCM Output combining module
PAE Power added efficiency
PAU Power amplifier unit
PSB Power supply bank
PSU Power supply unit
SCU Switching combiner unit
SS Solid state
SSHPA Solid state high power amplifier
SSTX Solid state transmitter Architectures for various ultra-high power RF and/or microwave solid-state (SS) combined high power amplifiers (CHPAs) will now be disclosed.

Built-in redundancy may be provided. The CHPA may be configured using multiple, identical solid state (SS) power amplifier units (PAUs), which may be line replaceable units (LRUs). The CHPA may have "m" online PAUs and "n" standby PAUs. The "m" online PAUs may be coherently combined to deliver an ultra-high power output. Each of the "n" standby PAUs in a standby mode is available to be automatically switched online to replace a failure in one of the "m" online PAUs.

A divider (DIV) may divide an input signal into multiple input signals, one for each PAU. A switching combiner unit (SCU) may combine the outputs from all of the online PAUs.

The CHPA may automatically detect a failure in any of the "m" online PAUs. The CHPA may also automatically replace an online PAU that has been detected to have failed with a standby PAU (failover), if available. Then, the failed previously online PAU is placed in an offline mode.

The CHPA may effectively remove the failed LRU from the critical path and thus provide continuous CHPA operation. The redundant architecture with automatic failure detection and replacement may enable an SS CHPA to deliver ultra-high power with outstanding operational availability and system reliability.

The CHPA architecture may also provide graceful degraded operation if more than "n" LRUs fail. In such a case, the SCU's impedance may automatically optimize to ensure optimized (high) combining efficiency.

A failed offline LRU may be removed for repair without interrupting operation. One or more of the online LRUs may also be safely removed, again without operational interruption.

True, hot swappable functionality may thus be provided by a combination of these features.

Multiple CHPAs can be combined into a single ultra-high power amplifier to meet higher system power levels and greater reliability requirements. The various features discussed herein may enable an ultra-high power SS CHPA to be constructed that meets or exceeds mission critical application requirements, such as with coherent radar transmitter systems.

FIG. 1 is a simplified block diagram of an example of a redundant, combined high power amplifier (CHPA) architecture. As illustrated in FIG. 1, the CHPA may include "m" online high power amplifiers, such as PAUs 101 and 103; "n" standby high power amplifiers, such as PAUs 105 and 107, an input power divider (DIV) 109, and a switching combiner unit (SCU) 111.

Each high power amplifier, such as PAUs 101, 103, 105, and 107, may be a high power solid state amplifier capable of producing a high power output, such as in the range of 2 to 5 kW or 1 to 10 kW. Each high power amplifier may be configured to amplify input signals in the RF or microwave frequency range. The signals may be pulsed, continuous, or of any other type.

The input power divider (DIV) 109 may be a divider circuit that divides a signal at its input 113 into several outputs, one for each PAU. The outputs may each have the same amplitude and phase characteristics. Each signal for an online PAU may be delivered to the online PAU to be amplified. Each signal for a standby or an offline PAU may be terminated in the input of the PAU not to be amplified.

The switching combiner unit 111 may coherently sum up the outputs from each online PAU into a single output at an output 115. The switching combiner unit 111 may also isolate the output port of standby and offline PAUs from the outputs of SCU and online PAUs.

The system may include an interface control unit (not shown in FIG. 1, but shown in FIG. 2 as ICU 250) that communicates with controllers built-in the PAUs and that detects when one of the online PAUs fails. The interface control unit may automatically deactivate a PAU that has been detected to have failed with a standby PAU, switching the failed PAU to offline and one of the standby PAUs to online. The interface control unit may similarly command the switching combiner unit 111 to start combining the output from the activated PAU and to isolate the combined output from the failed PAU.

The number "n" of standby units may be based on a target MTBF of the PAUs and take into consideration other factors, such as other reliability requirements, size limitations, and/or cost limitations.

The architecture may not allow a PAU failure to interrupt operation of CHPA. Only the input power divider 109 and the switching combiner unit 111 may be in the radio/microwave signal critical path.

The mean time between critical failure (MTBCF) and operation availability ($A_O$) of the described CHPA may be expressed as:

$$MTBCF_{CHPA} = \frac{MTBF_{DIV} MTBF_{SCU}}{MTBF_{DIV} + MTBF_{SCU}} \quad (6)$$

$$A_{OCHPA} = \left\{\frac{MTBF_{DIV} - MTR_{DIV}}{MTBF_{DIV}}\right\}\left\{\frac{MTBF_{SCU} - MTR_{SCU}}{MTBF_{SCU}}\right\} \quad (7)$$

where MTR stands for mean time to replace.

A 40 kW ultra-high power HPA may utilize a (9m+1 n) redundancy scheme for shipboard applications. The practical MTBFs for the PAUs, DIV, and SCU may be greater than 50 kHrs, 500 kHrs, and 150 kHrs, respectively.

The design goal of the MTR for the DIV and the SCU may be 2 hours. Accordingly, the DIV and SCU designs may ensure in this example a MTBCF of about 115 kHrs and an operation availability of about 99.998% with output power reaching an ultra-high power level of 40 kW.

The disclosed architecture may make an ultra-high power SSHPA feasible and its reliability superior to legacy radar transmitter technologies. The disclosed architecture may be suitable for mission critical high power RF and microwave applications.

Figure 2:
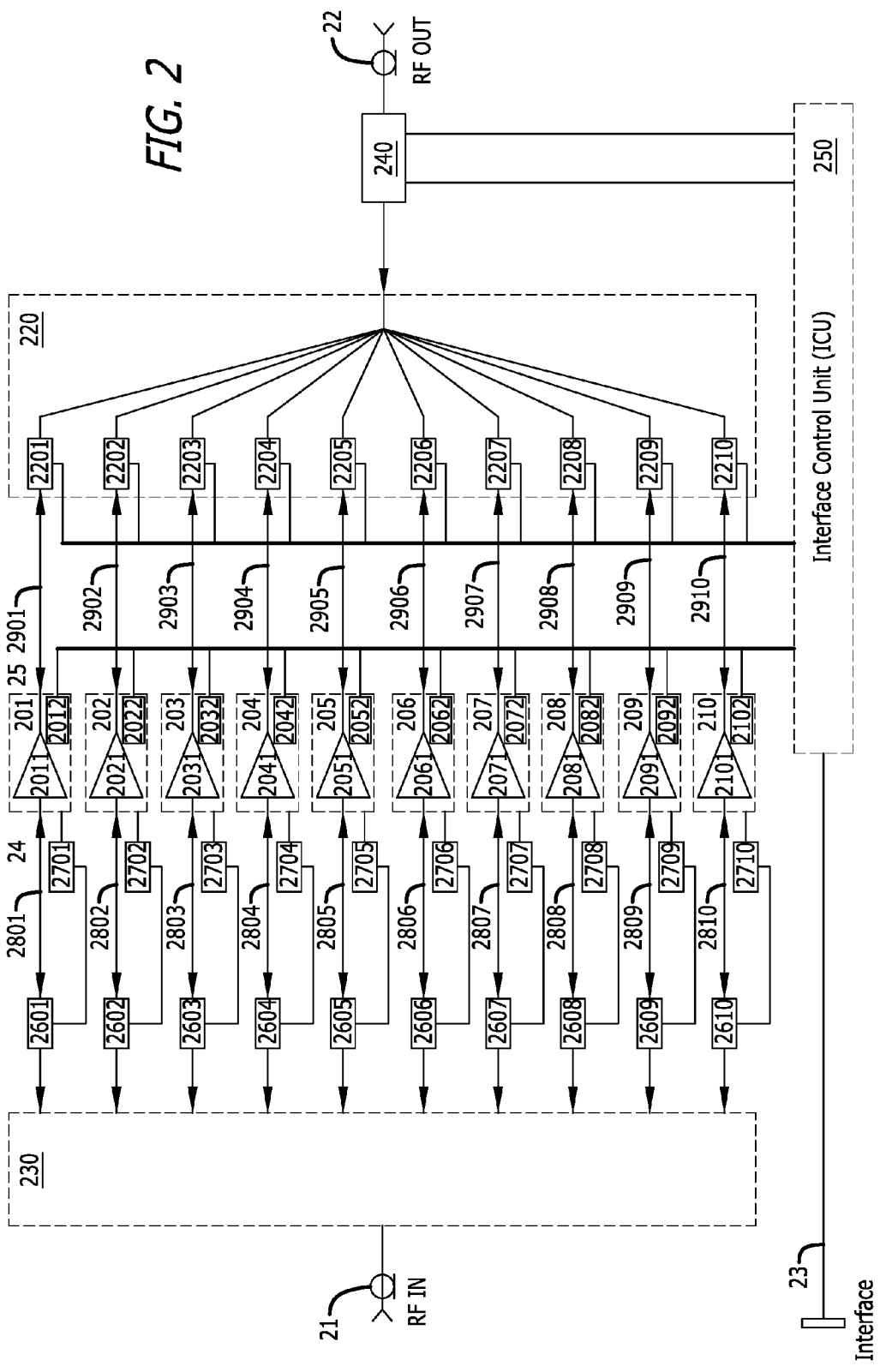
FIG. 2 is a simplified block diagram of an example of a 40 kW (9m+1n) combined high power amplifier (CHPA) with an interface control unit and other control components.

FIG. 2 is a simplified block diagram of an example of a 40 kW (9m+1 n) combined high power amplifier (CHPA) with an interface control unit (ICU) 250 and other control components. A different number of "m" and "n" PAUs may instead be used. The CHPA may include an input power divider (DIV) 230 of the type discussed above, PAUs 201-210 of the type discussed above, and a switching combiner unit (SCU) 220 of the type discussed above.

The interface control unit (ICU) 250 may effectuate automatic fail-over. The PAUs 201 to 209 may be initially online and the PAU 210 may be initially standby.

Each PAU may deliver 5 kW peak power and may include a PAU controller, such as PAU controllers 2012, 2022, 2032, 2042, 2052, 2062, 2072, 2082, 2092, and 2102.

Each PAU controller may monitor one or more operating conditions of its PAU that may be relevant to the operational status of the PAU, such as RF input to the PAU, RF output from the PAU, VSWRs, pulse width, pulse duty cycle, one or more temperatures, one or more voltages, and/or one or more currents. Information about these monitored characteristics may be delivered by each PAU controller to the interface control unit 250 and/or another subsystem.

Each PAU controller may be able to make adjustments to its PAU based on one or more control signals from the interface control unit 250 and/or one or more other control signals, such as adjustments in the gain and/or phase of its PAU and/or a change in its online status. Each PAU controller may be able to provide protection, including protection against over-voltage, over-current, over-temperature, over-pulse width, over-pulse duty cycle, and/or a high VSWR. These built-in shutdown protections may prevent damage to the PAU when the PAU encounters various over-limit conditions.

The signal combiner unit 220 may include high power RF switches 2201 to 2210. Initially, the RF switches 2201 to 2209 may be on (e.g., through) and the switch 2210 may be off (e.g., isolated). The outputs of the PAUs 201-210 may be connected to the switching combiner unit 220 via high power, matched cables 2901 to 2910. The summed 40 kW power output from the switching combiner unit 220 may be delivered through an output coupler 240 to an RF output port 22. The output coupler 240 may couple CHPA forward power and reflected power to the ICU 250 to be detected thereby to monitor CHPA operating status.

The interface control unit 250 may monitor the parametric status of all PAUs through their built-in PAU controllers and report this status to the upper level control unit if needed via an I/O interface 23. The output coupler 240 may sample forward and reflected signals and send these sampled signals to the interface control unit 250 as part of the CHPA status monitoring.

When a failure or out of specification condition is detected among any of the monitored parameters during the amplification of an input signal by the PAU controller or the interface control unit 250, the interface control unit 250 may delay taking corrective action until the input signal ceases, such as after a pulse in a radar signal is finished, but before the next pulse begins.

For example, the interface control unit 250 may have determined that the PAU 201 has failed or is no longer operating within a specified parameter based on the report from the controller 2012. As soon as the interface control unit 250 detects the cessation of the input signal or is advised of its completion by an acknowledge signal received over the interface 23, the interface control unit 250 may place the failed PAU 201 offline via its controller 2012, turn off its RF switch 2201 inside the switching combiner unit 220, place the PAU 210 online via its controller 2102 to replace failed PAU 201, and turn on its RF switch 2210 inside the switching combiner unit 220. This intra-pulse detection and inter-pulse automatic fail-over scheme may avoid switching actions during the presence of a high power RF signals which otherwise might cause a high power RF switch failure or other critical failure or problem.

The automatic fail-over action may not interrupt power pulse transmission, which might result in the delivery of a defect pulse with −1 dB lower power in the worst case. The RF switches in the switching combiner unit 220, such as the RF switch 2201, may provide a high degree of isolation when off (e.g., isolated), thus preventing harmful radiation from flowing back to the cabinet of a failed and offline PAU 201 after it is physically removed from service.

The PAUs may each receive their input through a detachable blind mate interface, such as through one of the TNC connectors 24. Similarly, the PAUs may each deliver their output through another detachable blind mate interface, such as through one of the SC connectors 25. This may enable each PAU to be easily detached and removed from the rest of the system for repair, testing, and/or replacement.

Positional sense switches 2701-2710 may each detect the presence of their respective PAU. When a PAU is fitted into its input TNC connector 24 and output SC connector 25, its respective positional sense switch may be configured and oriented to close. Conversely, When a PAU is detached from its input TNC connector 24 and output SC connector 25, its respective positional sense switch may be configured and oriented to open. The switch may be set to detect the detachment of a PAU after the removal process begins, but before any electrical connection is broken.

The combined high power amplifier (CHPA) that is illustrated in FIG. 2 may include input RF switches 2601 to 2610 that are connected to and controlled by their respective positional sense switches 2701 to 2710. The input RF switches 2601 to 2610 may be connected to their respective PAU through matched connection cables 2801-2810.

Thus, the removal of a PAU from the CHPA may automatically stop its input signal from reaching its input TNC connector. Conversely, the insertion of a PAU into the CHPA may cause its input signal to be delivered to its input TNC connector. Thus, each PAU may be hot swappable.

Figure 3:
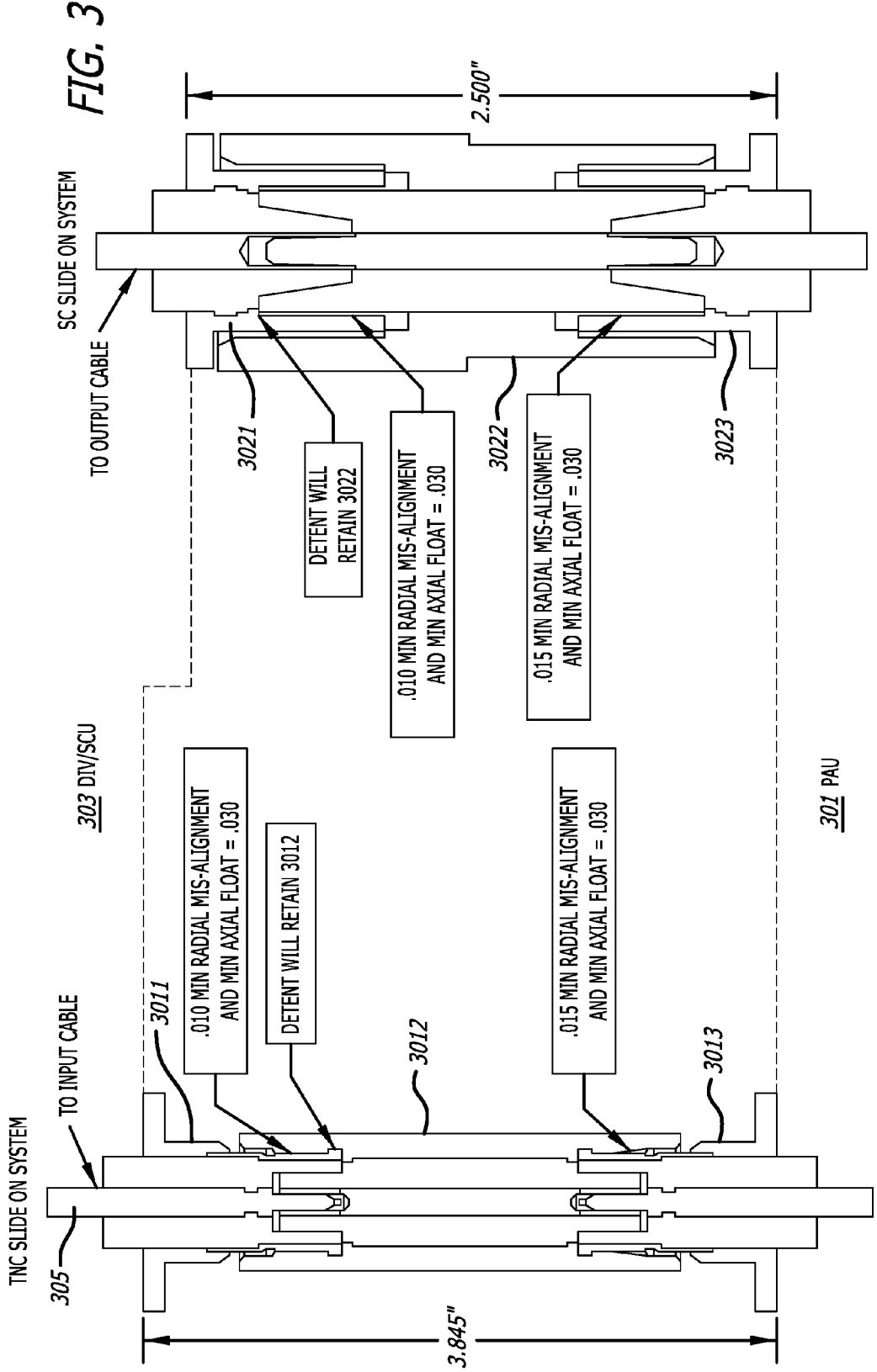
FIG. 3 illustrates the mechanical layout of an example interface between a PAU and a combined input power divider/switching combiner unit.

FIG. 3 illustrates the mechanical layout of an example interface between a PAU 301 (which may be of any of the types discussed above) and a combined input signal divider and switching combiner unit (DIV/SCU) 303 including an input power divider/switching combiner unit (which may be any of the types discussed above). This interface may be used in the CHPAs illustrated in FIGS. 1 and 2.

This interface may include the male end of a slide-on blind mate TNC connector 3013 and the male end of a high power slide-on blind mate SC connector 3023 fastened to the exterior of the PAU 301, the male end of a slide-on blind mate TNC connector 3011 and the male end of a slide-on-blind mate SC connector 3021 fastened to the exterior of the combined DIV/SCU 303, and matched connecting TNC RF barrel 3012 and SC RF barrel 3022 proving an electrical connection between the shield and central conductor of their paired connectors, respectively. The SC connectors may facilitate an output power of at least 5 kW peak power. This scheme may be used on each PAU.

The use of blind mate connectors may allow each PAU to be connected and disconnected from the circuit with a simple sliding motion. A divided RF input signal may thus propagate from a matched input cable 305 to the slide-on blind mate TNC connector 3011 on the exterior of the combined DIV/SCU 303, then through the TNC RF barrel 3012 to the slide-on blind mate TNC connector 3013 on the exterior of the PAU 301, and then through the slide-on blind mate TNC connector 3013 to the PAU 301. The input signal may be amplified by the PAU 301 and then sent through the high power slide-on blind mate SC connector 3023 on the exterior of the PAU 301 through the SC RF barrel 3022, and then through the blind mate slide-on SC connector 3021 on the outside of the combined DIV/SCU 303.

The mating connectors and the positional sense switch associated with each TNC connector may be configured such that: (1) electrical contact is made between both sets of mating connectors on the PAU 301 before the position sense switch detects the connection; and (2) electrical contact is not broken between any set of mating connectors on the PAU 301 until after the position sense switch detects that the PAU 301 is being detached.

Each corresponding set of blind mate slide-on connectors may be configured to allow at least 25 mils of radial misalignment and at least 60 mils of axial float. The position sense switches may be configured to detect a connection and disconnection when there are only 20 mils of axial separation. This may enable the interface control unit 250 to detect the removal of a PAU and to deactivate it before its electrical connections are broken. This may similarly allow a PAU to be inserted into an empty slot and for its electrical connections to be established before power is applied to the inserted PAU by the interface control unit 250.

For example, when an online PAU is removed during operation, such as the PAU 201 in FIG. 2, the positional sense switch 2701 may sense the removal before any electrical contact with the PAU has been broken, such as when the displacement is greater than 20 mils from a nominal position. The positional sense switch 2701 may send a control signal to the input RF switch 2601 to isolate the RF input signal from the PAU 201. Due to the lack of input signal to PAU 201, the PAU 201 may not provide any output power. The absence of this output power may be detected by the interface control unit 250 which may then deactivate the PAU that is being removed within no more than 100 μS following detection of that removal by the input RF switch 2601. This is based on the assumption that it will take more than 100 μS for the PAU 201 to be moved past the point of tripping the input RF switch 2601 until the first of its electrical connections with the circuit are broken. Deactivating the input to the PAU 201 and the PAU 201 before any of its electrical connections with the circuit are broken may help insure that there is no high VSWR condition or arcing damaged caused by the removal of an online PAU 201, thus further facilitating hot swapping.

Figure 33:
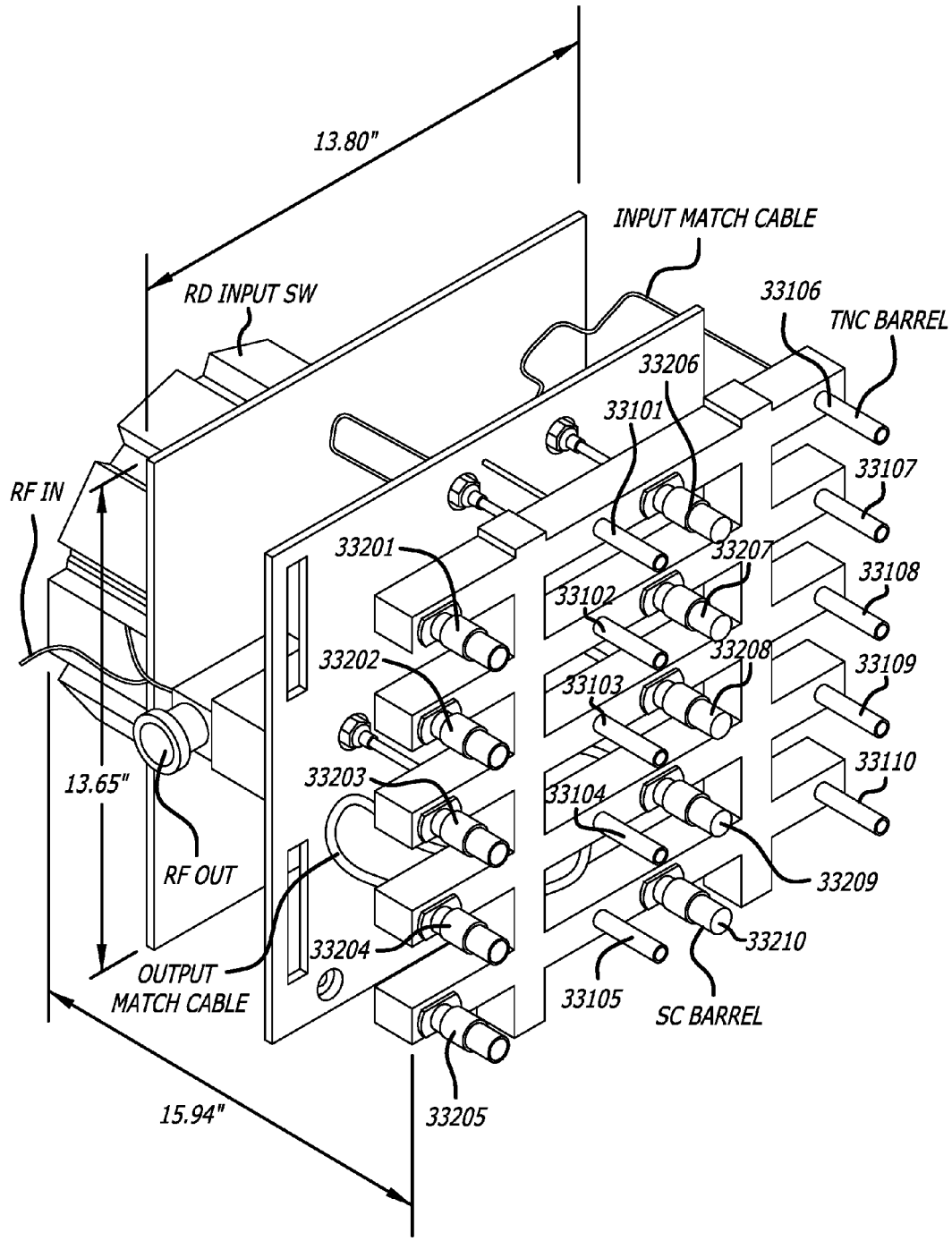
FIG. 33 illustrates an example of a 10-way input power divider and switching combiner unit (DIV/SCU) combined into a single unit.

The TNC and SC blind mate slide-on connectors may each include a detent to hold their respective barrels in place, as shown in FIG. 33, during removal of the PAU 301. 33101 to 33110 are TNC barrels to the inputs of 10 PAUs, and 33201 to 33210 are SC barrels to the outputs of 10 PAUs.

Figure 4:
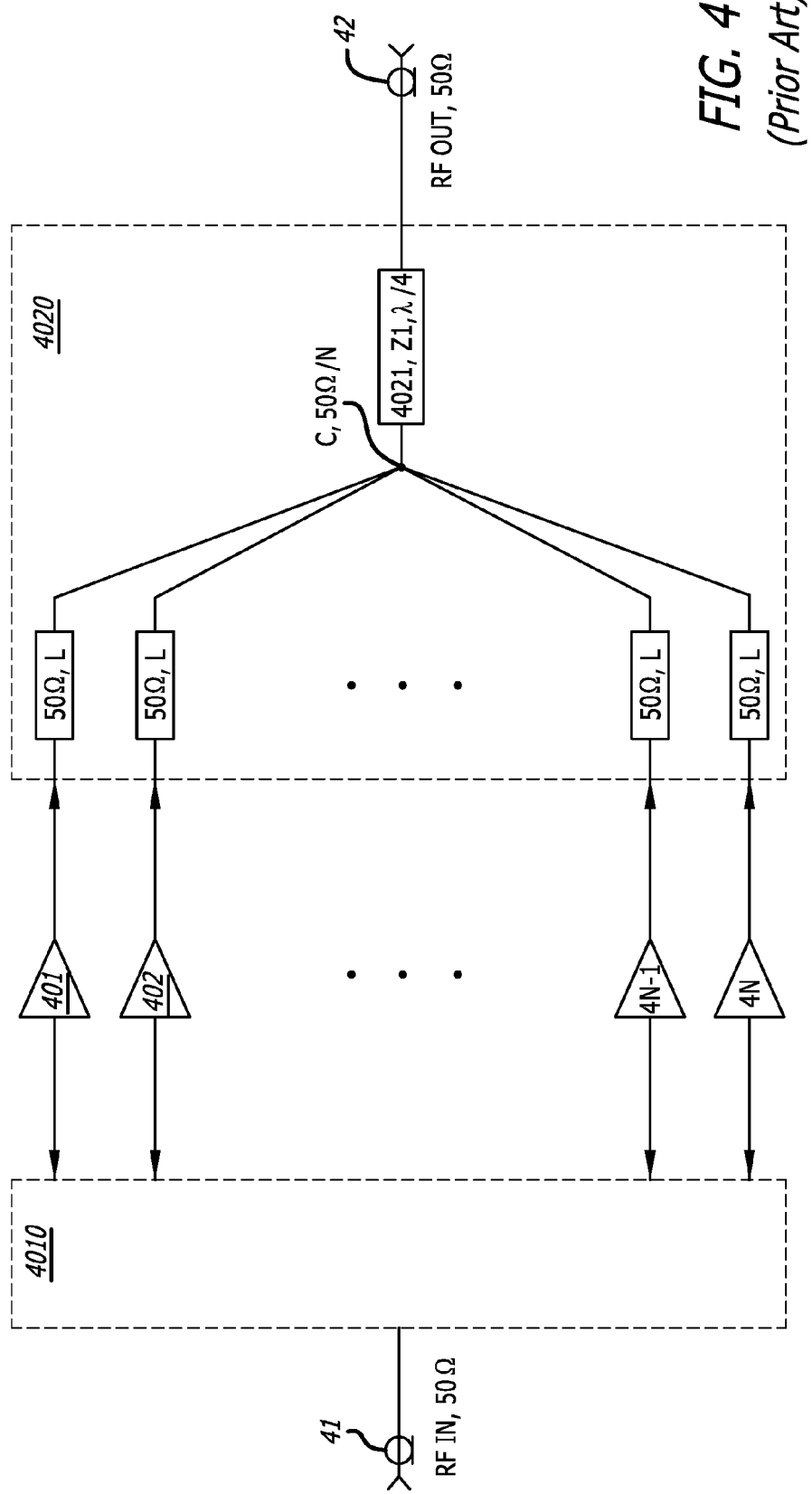
FIG. 4 illustrates an example of a prior art high power combined amplifier that uses a conventional radial combiner with "n" inputs.

FIG. 4 illustrates an example of a prior art high power combined amplifier that uses a conventional radial combiner 4020 with "n" inputs. The combined amplifier includes an input port 41, an input power divider 4010, and PAUs 401-4N. The conventional radial combiner 4020 ties "n" 50Ω input ports to a common port and transfers the (50/N) ohm impedance to 50Ω output impedance. The coherent amplified RF signals are provided as inputs to the "n" input ports of the conventional radial combiner 4020. All of the "n" RF signals travel through 50Ω lines with equal length L, join at the geometric center node "C," and are coherent. Hence, the impedance of node "C" is 50 Ω/N. An impedance transformer 4021 has an impedance Z1 expressed in equation 8 and a λ/4 electrical length:

$$Z1 = \frac{50\Omega}{\sqrt{N}} \quad (8)$$

and will transfer the (50/N)Ω impedance to a 50Ω output impedance at an output port 42. More than one step transformer may be used to increase bandwidth.

The conventional radial combiner 4020 may not have sufficient port-to-port isolation to allow a high power or ultra-high power output combiner to operate safely with a failed PAU at one of its ports for any period of time. When a single PAU fails, such as PAU 401, the total power loss at the output port 42 may exceed 2/N times the nominal power. Due to the VSWR effects of operating the high power radial combiner with just a single failed PAU in one port, the mismatch may cause power reflections that may damage the combiner and all of the other operating PAUs over time.

This may be especially true in the case of a "short" failure located at a multiple of a 180° electrical length from node "C." The "short" may parallel with 50 Ω/(N−1) to create near 0Ω impedance at "C." Then, nearly 100% of the output power may be reflected back to all of the PAUs. This may well cause a catastrophic failure.

When a PAU is physically removed, the corresponding input port of the combiner may be left un-terminated or un-isolated, so that all of the other PAUs may contribute significant power to the total of (N−1)/N of PAU outputs at the open port. Thus, the large harmful radiation may also be present if one of the PAUs is physically removed while in the transmit mode. Under such conditions, the CHPA with a conventional radial combiner may not meet standards for EMI/EMC compliance and safety regulations, at a minimum. Even worse, when the open port is located at an odd number of quarter wavelengths from the node C, the effective near 0Ω impedance at "C" may cause catastrophic failure.

This entire system may need to be shut down while each failed PAU is replaced. But this may result in an extremely low operation availability. So making an ultra-high power CHPA with a conventional radial combiner may not be a viable solution.

The practical MTBFs for the PAUs, DIVs, and radial COMs that have been described may be at least 50 kHrs, 500 kHrs, and 150 kHrs, respectively. Then, the MTBCF of a conventional CHPA including 10 PAUs may be less than 5 kHrs.

Figure 5:
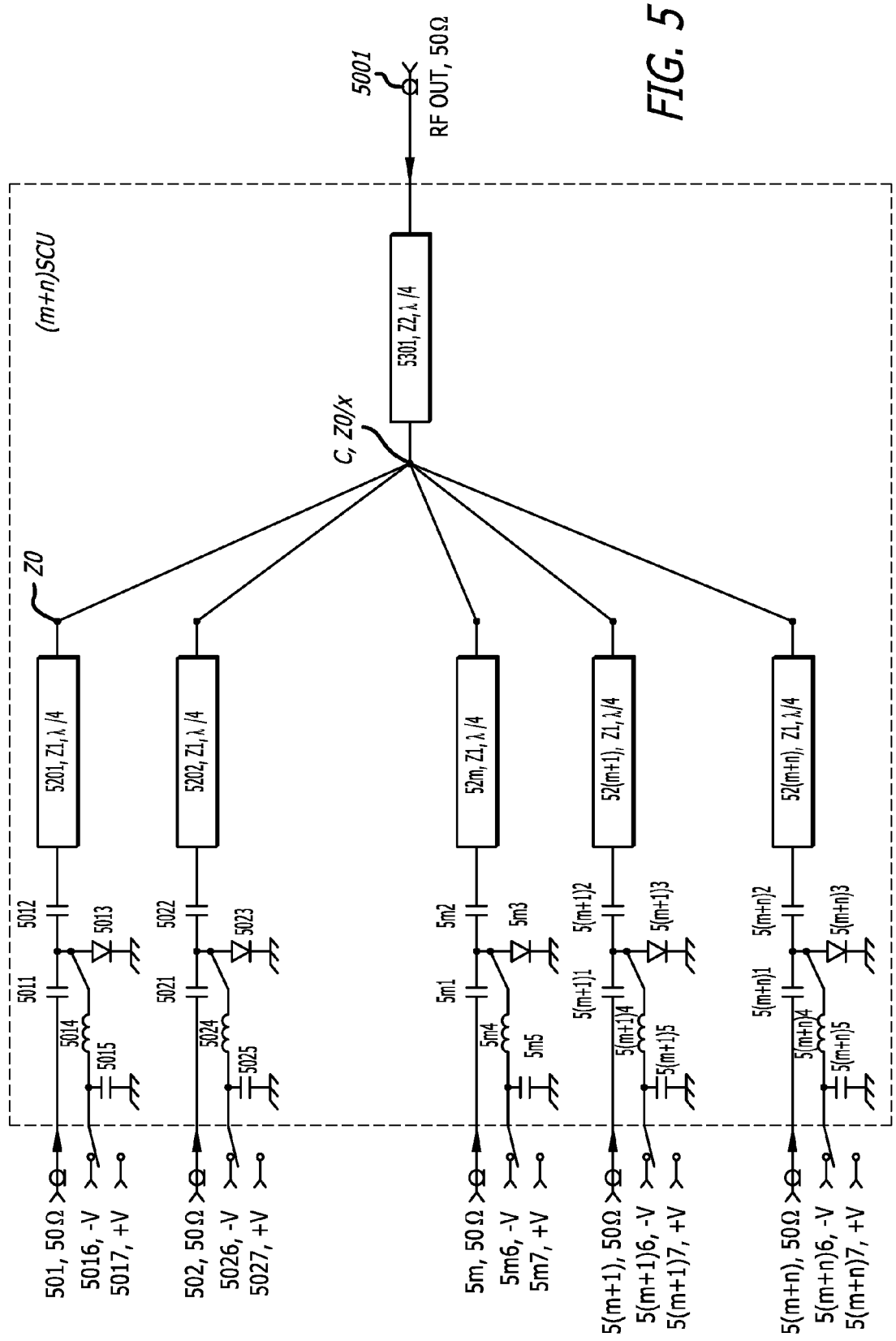
FIG. 5 illustrates an example of a switching combiner unit (SCU) circuit that can automatically and safely disconnect an input port in response to a shutdown command.

FIG. 5 illustrates an example of a switching combiner unit (SCU) circuit that can automatically and safely disconnect an input port in response to a shutdown command, such as a shutdown command from an interface control unit, such as the interface control unit 250 in FIG. 2. Such an SCU may be used as the SCU 111 in FIG. 1 and/or the SCU 220 illustrated in FIG. 2.

The SCU illustrated in FIG. 5 may include high power RF switches to all input ports among which "m" ports are initially switched on and "n" ports are initially switched off. Thus, the SCU introduces redundancy to the combining scheme. When a PAU to one of "m" on ports fails, its port may be switched off (isolated) and one of "n" ports may be switched on at about the same time so that the output impedance and output power may remain unchanged.

High power PIN diode RF switches 5013-5(m+n)3 may be used as the switches. However, any other type of switch may be used instead, such as a FET, bipolar transistor, mechanical switch, or electro-mechanical switch.

In an initial default mode, the coherent high power RF signals from "m" online PAUs may be input to 50Ω input ports 501 to 5m.

The switching functionality associated with the first input port 501 will now be explained. The same explanation applies to the other input ports and their associated −V control inputs 5026 to 5(m+n)6, +V control inputs 5017 to 5(m+n)7, capacitors 5025 to 5(m+n)5, 5021 to 5(m+n)1, and 5022 to 5(m+n) 2, inductors 5024 to 5(m+n)5, and transmission lines 5202 to 52(m+n).

The RF signal from the input port 501 may propagate through two blocking capacitors 5011 and 5012, between which the high power PIN diode 5013 may shunt between the RF line and ground. A reverse voltage −V at a −V control input 5016 may be filtered by a capacitor 5015 and passed through an RF coil 5014 and then to the PIN diode 5013, causing an effective resistance of the PIN diode 5013 to be in the tens of thousands of ohms. Thus, the RF insertion loss due to the addition of the PIN diode may be negligible.

All "m" signals through identical RF switches and transmission lines 5201 to 52m with Z1 impedance and λ/4 electrical length may merge at the center C of the radial shape SCU, at which the "n" off ports also intercept. For the initially off input ports, a forward voltage +V may be applied at +V control inputs 5(m+1)7 to 5(m+n)7. This may cause the effective resistance of the PIN diodes 5(m+1)3 to 5(m+n)3 to be about 0.25Ω. The 0.25Ω low impedance in the places of forward biased diodes may be transferred to near 10 kΩ at node "C" when Z1=50Ω. The paralleling effect from "n" number of nearly 10 kΩ resistors at "C" may be insignificant.

Thus, the forward biased diodes may isolate their respective input ports from the common junction "C."

The selection of Z0 may be associated with the default "m" and operation bandwidth. With a large "m" value and a broad bandwidth requirement, making Z0 greater than 50Ω may increase the impedance Z0/x at node "C." This may ease the impedance transformation by transformer 5301 with Z2 impedance and λ/4 electrical length. The multiple sections of quarter wavelength lines may be implemented at Z2 line to increase the bandwidth. When an (m+n)SCU is designed to operate at optimal power delivery at an output 5001 to 50Ω, the random parameter x in node "C" may be "m" to achieve the best VSWR (theoretically 1:1) with "m" PAUs online. Even with (n+1) failed PAUs and (m−1) PAUs online, the SCU presents {m/(m−1)}50Ω, instead of 50Ω nominally with <n failed PAUs.

The larger "m" is, the closer SCU output impedance may be to 50Ω. For example, for m=9, the VSWR of SCU may be 1.125:1 when 8 ports are on. Therefore, graceful degradation may be achieved with outstanding combining efficiency. On the other hand, more than "m" ports of the (m+n)SCU can be placed "on" in order to achieve higher than nominal power delivery. Thus, the disclosed (m+n)SCU may be flexible so that it can be implemented in various applications.

Table 2 below demonstrates the effect on (m+n)SCU VSWR with different numbers of online PAUs and (9+1) SCU.

TABLE 2

(m + n)SCU VSWR with different numbers of online PAUs and (9 + 1)SCU

| (m + n)SCU Optimized for "m" PAUs | | (9 + 1)SCU Optimized for 9 PAUs operation | | | |
|---|---|---|---|---|---|
| # "online" PAUs | Output VSWR | # "online" PAUs | VSWR | Power Loss (dB) | Output Power (%) |
| m + 1 | (m + 1)/m | 10 | 1.11:1 | −0.012 | 110.8% |
| m | 1:1 | 9 | 1:1 | 0.00 | 100% |
| m + 1 | m/(m − 1) | 8 | 1.13:1 | −0.016 | 88.5% |
| m − 2 | m/(m − 2) | 7 | 1.29:1 | −0.07 | 76.5% |
| m − 3 | m/(m − 3) | 6 | 1.50:1 | −0.18 | 64% |

Note that, in the (9+1)SCU example, the SCU may present excellent 1.29:1 VSWR and −0.07 dB transmitted power loss due to mismatch with 7 PAUs online or 3 failed PAUs. If more than 3 ports are "off," the (9+1)SCU may show 1.50:1 VSWR and −0.18 dB power loss which may be undesirable. In this case, the entire SCU can be programmed to be shut down by its interface control unit. As suggested by this last sentence, the various switching control signals that have been described may originate from an interface control unit, such as the interface control unit 250 shown in FIG. 2.

The parameter x can also be optimized by considering that (m+n)SCU may support nominal y PAUs online, graceful degradation with y−1 PAUs online, and high power mode and high power operation with y+1 PAUs online. Then, $$x = \sqrt{(y-1)(y+1)} \tag{9}$$

The corresponding VSWR for (y−1) ports on and (y+1) ports on may be the same as equation 10, so symmetric VSWR performance can be achieved:

$$VSWR = \sqrt{(y+1)/(y-1)} \tag{10}$$

If y=8 in (9+1)SCU, then x=7.937. Therefore, the SCU VSWR may be 1.134:1 for 9 and 7 PAUs online, while 1.007:1 for 8 PAUs operation. The optimal design approach may be subject to specific application requirements.

Figure 6A:
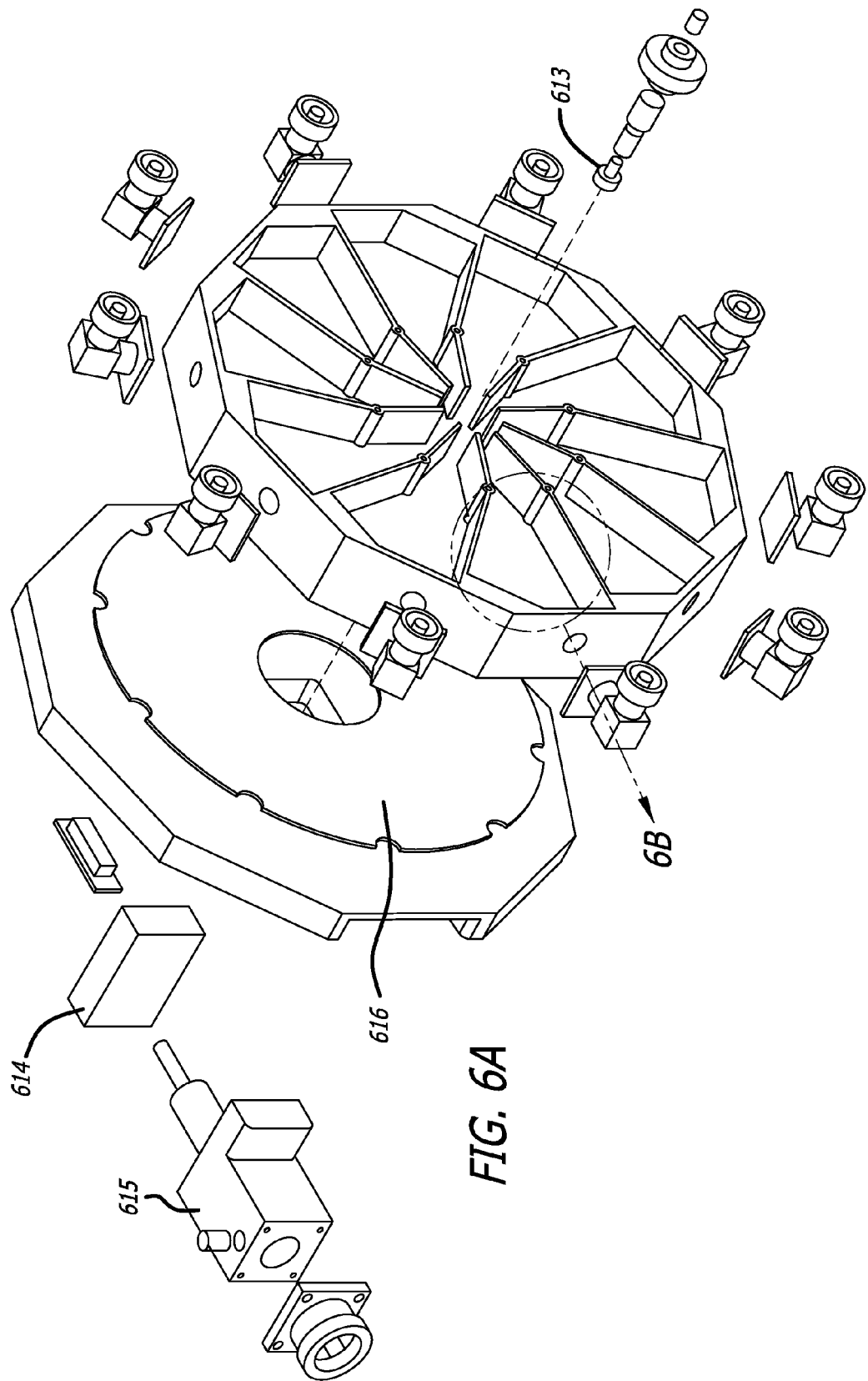
FIG. 6A illustrates an exploded view of an example of a switching combiner unit.
Figure 6C:
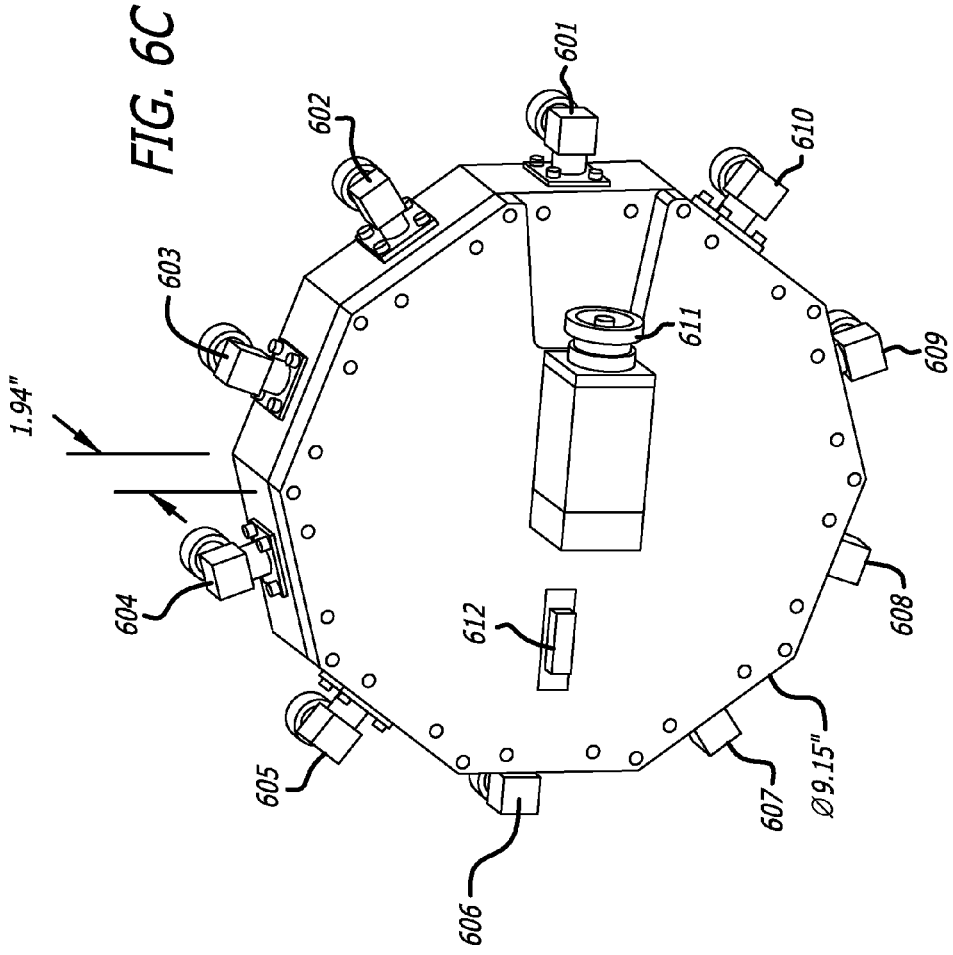
FIG. 6C illustrates the switching combiner unit fully assembled.
Figure 6B:
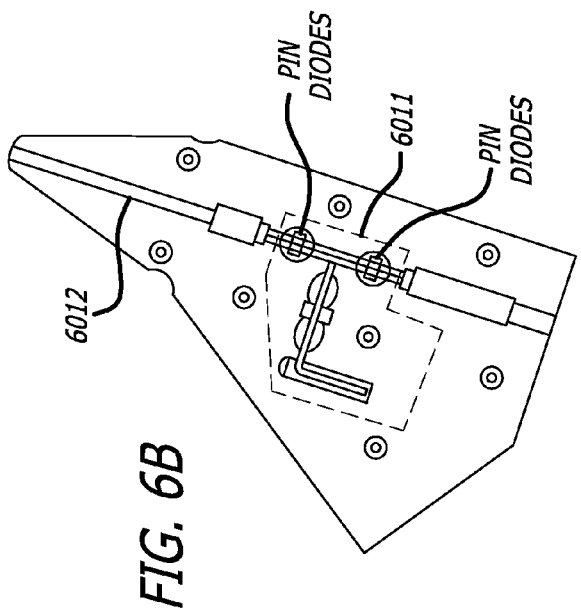
FIG. 6B illustrates an enlarged view of a port section of the switching combiner unit.

FIG. 6A illustrates an exploded view of an example of a switching combiner unit (SCU); FIG. 6B illustrates an enlarged view of a port section of the switching combiner unit; and FIG. 6C illustrates the switching combiner unit fully assembled. This SCU may be used as the SCU 111 in FIG. 1 or the SCU 220 in FIG. 2. The SCU in FIGS. 6A-6C may contain the circuit illustrated in FIG. 5.

The SCU may be configured for 9 initially online PAUs and 1 initially standby PAU (a (9+1)SCU) that can deliver more than 40 kW peak power with nominal 9 ports on, each of which may receive about 5 kW nominal peak power operating at 3.8% nominally and up to 6% maximum duty cycle under pulsed condition for an approximately 900 MHz radar application. Right angle SC connector RF input ports 601 to 610 may be capable of handling more than 5 kW peak power, and 50Ω output port 611 may be a 7/16 DIN connector specially designed to handle more than 40 kW peak power.

Each of the ten input circuit branches may have a uniform layout consistent with a conventional radial combiner, with a center node 613 being low impedance. The impedance transformations from the center node 613 to the 50Ω output port 611 may be implemented by two sections of impedance transformations. One may be a strip-line transformer 614 and another may be a coaxial transformer 615.

Each of the input ports may be associated with PIN diode switching circuitry of the type discussed above in connection with FIG. 5. Multiple diodes may be implemented to increase switching isolation.

A high power RF switch 6011 utilizing PIN diodes may be separated by a λ/4 transmission line impedance transformer 6012 from the center node 613. A reverse voltage applied to the diode through an interface Sub-D connector 612 may place the PIN diode switch on, and a forward voltage may turn the input port 601 off. The same may apply to the switching circuits for the other ports.

A distribution board interface 616 may be between the Sub-D connector 612 and the ten RF switches. +V/−V bias may be supplied via the Sub-D connector 612 and may be distributed via the distribution board interface 616 to the location of its corresponding diodes.

In another embodiment, a high isolation passive input power divider design may have the symmetric splitting circuitry like the one in radial combiner and built-in terminations that divide the input signal uniformly and absorb the reflected signal due to the output port mismatch. The built-in terminators to each output port may independently absorb the reflected signal from its corresponding port and may not superimposition to other output ports. This may be superior to a radial divider which may have no port-to-port isolation and to a Wilkinson divider which may have poor port-to-port isolation.

Figure 7:
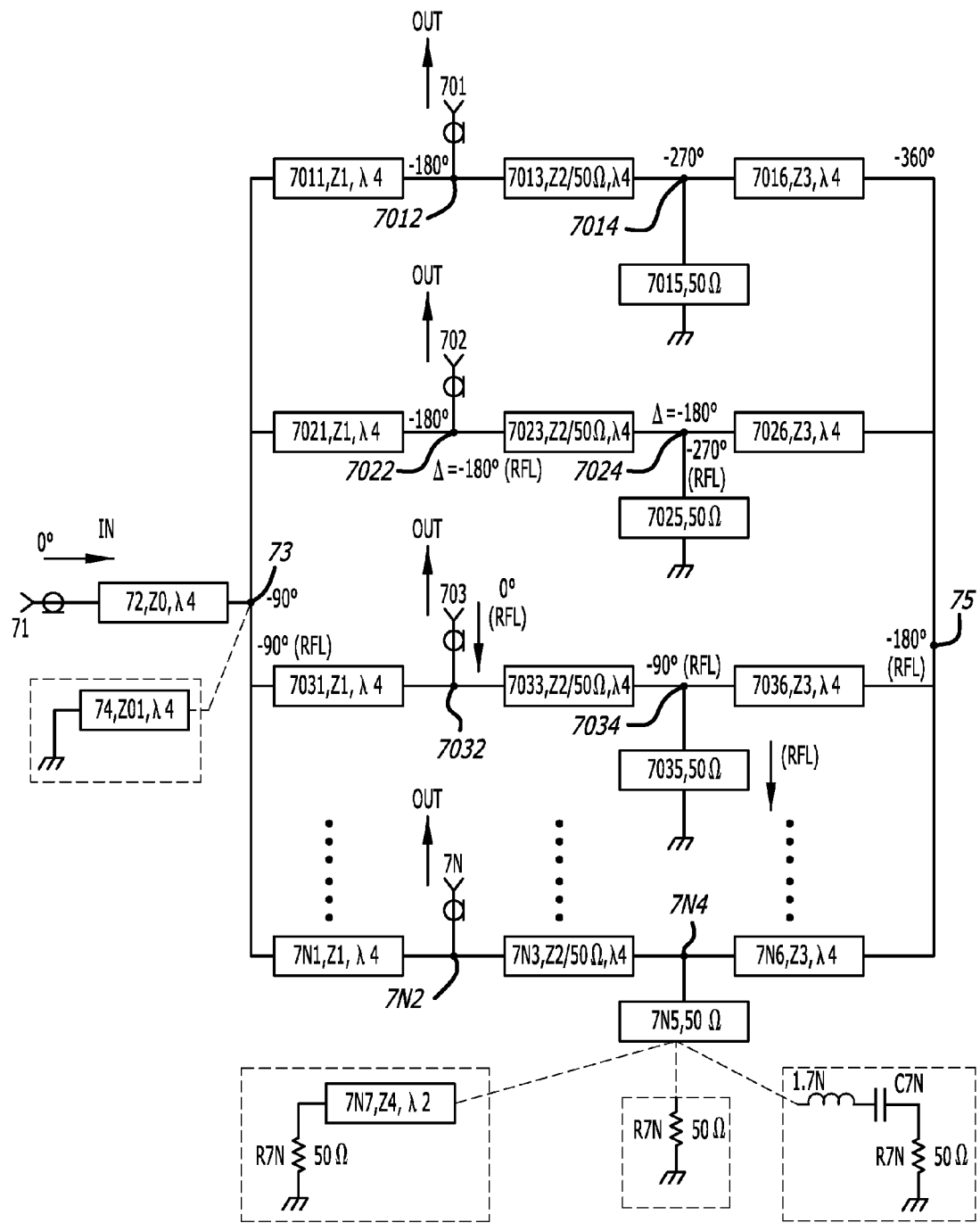
FIG. 7 is a schematic of an example of an N-way input power divider that may provide high port-to-port isolation.

FIG. 7 is a schematic of an example of an N-way input power divider (DIV) that may provide high port-to-port isolation. This divider may be used as the divider 109 in FIG. 1 or the divider 230 in FIG. 2.

An input RF signal may enter an input port 71 and travel through a Z0 transmission line 72. The input signal may then be divided into "n" ways equally at junction 73. The divided input signals may propagate to their respective output ports 701 to 7N. In addition, the signal at a junction 7012 may travel through a Z2 λ/4 transmission line 7013 with a −270° phase at a junction 7014, so is the signal −270° phase at 7024.

The forward signal at the 50Ω load 7015 may continue its path through a Z3 λ/4 transmission line 7016 and a Z3 λ/4 transmission line 7026 to a 50Ω load 7025 with −450° phase. That is to say, there is a forward signal from 7023 and a reverse signal from the transmission line 7013 with Δφ=−

180° at the 50Ω load 7025. Thus, the 50Ω loads 7015 to 7N5 are virtual grounds to the output ports 701 to 7N. The 0Ω virtual ground is transformed to near infinite high impedance at the junctions 7012 to 7N2. Therefore, the N-way divider, from input port 71 input to output ports 701 to 7N can be designed following conventional radial combiner design rules, as in FIG. 4, except that $L=\lambda/4$.

Assume that there is a reflected signal inputted at an output port 703, due to a mismatch at the output port 703. The signal may travel through the Z2/50Ω transmission line 7033 to a 50Ω load 7035. In addition, the signal may travel through a Z1 transmission line 7031 and a Z3 transmission line 7036, the phase changes for reflected signal paths are noted (RFL). The two signals may eventually meet at an output port, such as the output port 702, with $\Delta\phi=-180°$ phase and cancel each other. Therefore, the signal input from one output port, such as the output port 703, will not be present at any other output port, such as the output port 702. Thus, outstanding port-to-port isolation may be achieved.

The circuit illustrated in FIG. 7 may provide more than a 12% bandwidth around the center frequency. Other wideband features may be added. For example, a $\lambda/4$ transmission line or multiple parallel higher impedance lines may be added at the junction 73. A series tuned LC circuit, including L7N and C7N, may in addition or instead be added at the input of the built-in 50Ω load. A −180° series circuit can be implemented using a $\lambda/2$ Z4 transmission line 7N7. Optional broadband circuits may be included, as illustrated in dash boxes at the bottom of FIG. 7 and may improve the bandwidth by more than 28% from the center frequency.

Figure 8A:
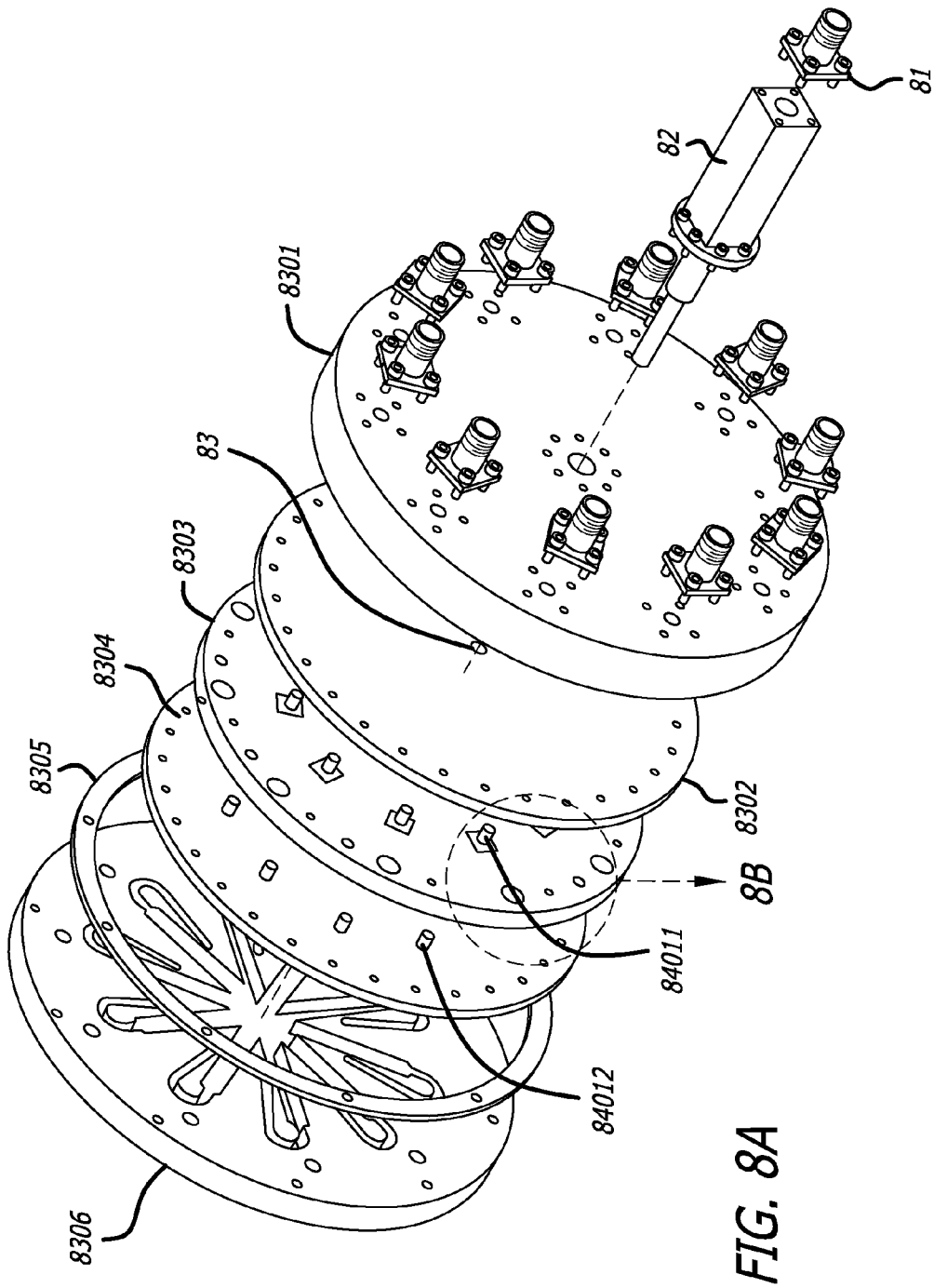
FIG. 8A is an exploded view of an example of a 10-way input power divider.
Figure 8B:
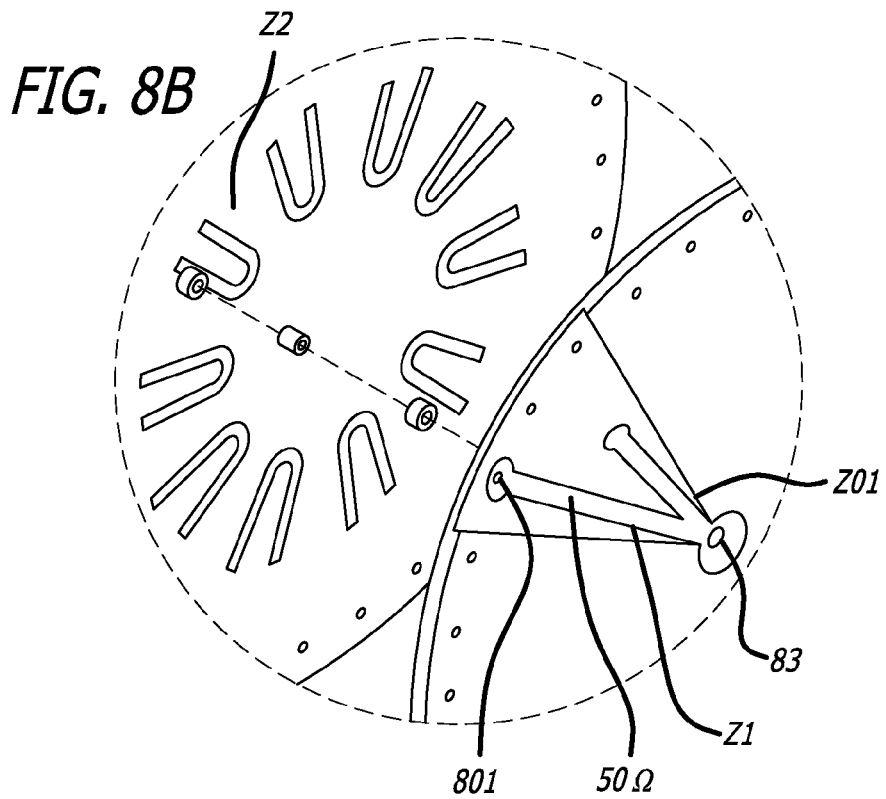
FIG. 8B illustrates an enlarged view of a portion of a PCB within the divider.
Figure 8C:
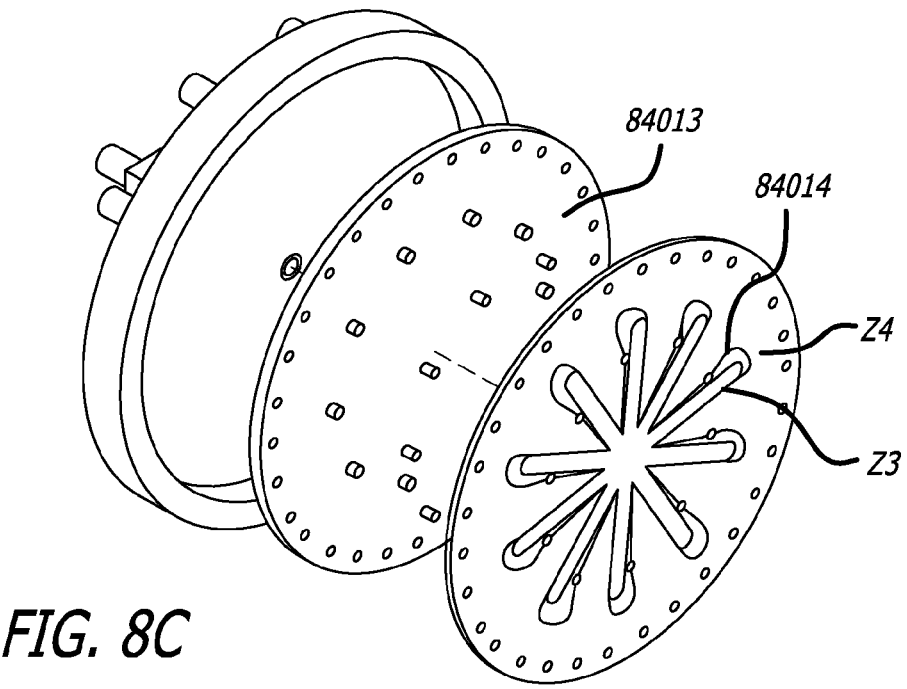
FIG. 8C illustrates a rear view of certain components of the divider.
Figure 8D:
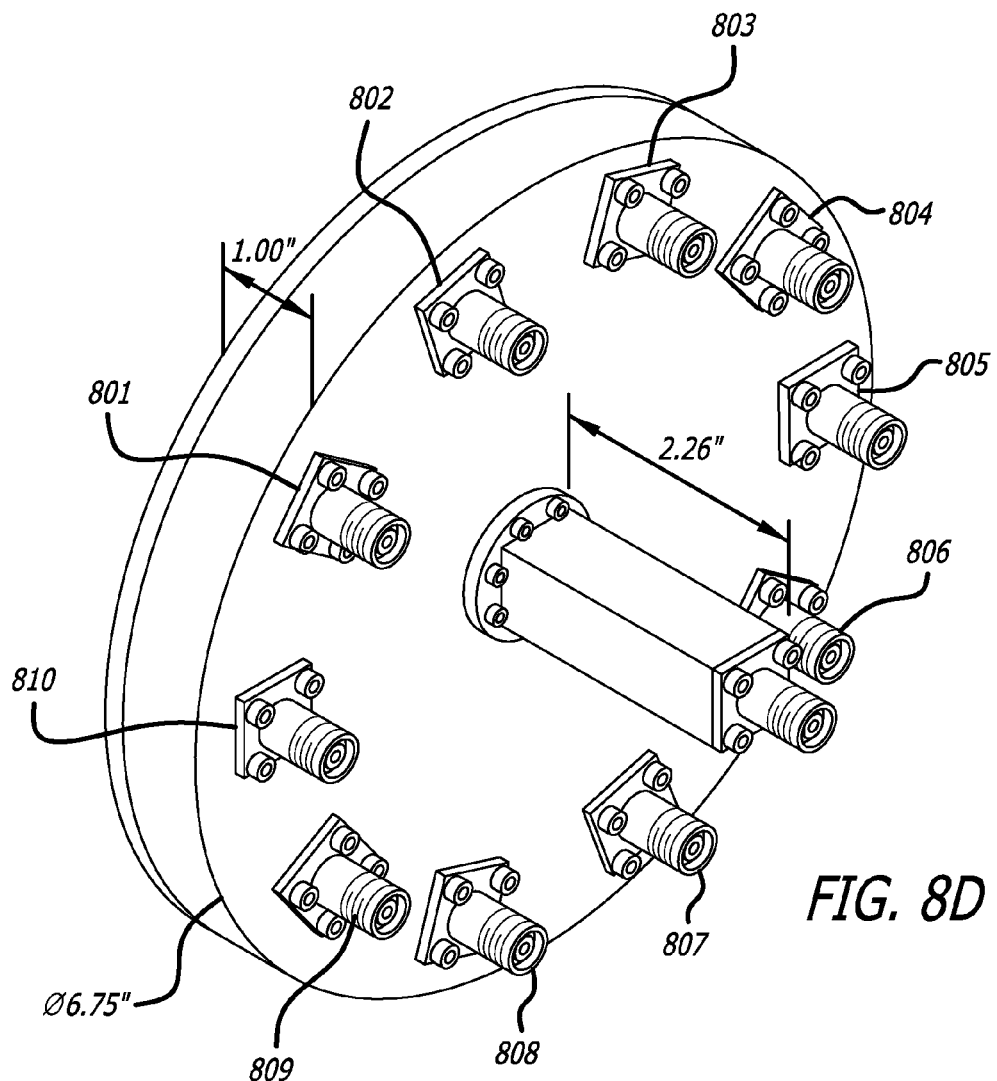
FIG. 8D illustrates the divider fully assembled.

FIG. 8A is an exploded view of an example of a 10-way input power divider; FIG. 8B illustrates an enlarged view of a portion of a PCB within the divider; FIG. 8C illustrates a rear view of certain components of the divider; and FIG. 8D illustrates the divider fully assembled. The figures illustrate various transmission lines and built-in terminators using two PCB assemblies interconnected via SMP RF connectors. This divider may be used as the divider 109 in FIG. 1 or the divider 230 in FIG. 2. This divider may contain the circuit illustrated in FIG. 7.

The divider may operate within a band from 800 MHz to 1000 MHz.

An input connector 81 and output connectors 801 to 810 may be TNC, which may be adequate to handle 100 W peak power. A $\lambda/4$ coaxial transmission line 82, like the transmission line 72 in FIG. 7, may transform 50Ω at the input connector 81 into a low impedance at a center hole 83, where all ten identical branches may merge. All of the transmission lines in FIG. 7 may be laid out on two multilayer PCBs 8302 and 8304, which may be enclosed by a housing 8301, a partition plate 8303, a gasket 8305, and a lid 8306. The two multi-layer PCBs 8302 and 8304 may have SMP connectors, such as SMP connectors 84012 and 84013, which may be interconnected via SMP barrels, such as SMP barrel 84011. Built-in terminators, such as built-in terminator 84014, may be mounted on the PCB 8304.

FIG. 8B illustrates an exploded view of one of what may be ten identical circuits from input connector 81 to output connector 801. It illustrates transmission line design details, specifically transmission lines Z1, Z01, Z2, Z3, and Z4, which may be the same as the corresponding ones in FIG. 7. The signal at the center hole 83 of the PCB 8302 may go through the transmission line Z1 and then through a 50Ω line to the output connector 801. The joint of Z1 line and 50Ω line may be interconnected through vias and SMP connectors and a barrow to the multi-layer PCB 8304.

The broadband $\lambda/4$ transmission lines Z01 may be laid out in the PCB 8302. However, a total of ten of transmission lines Z01 may be implemented so that each individual line can provide a higher impedance with a narrow trace width. The SMP connector 84012 on the PCB 8304 may go to the $\lambda/4$ transmission line Z2, and the vias may continue its circuitry to the far side of PCB 8304 illustrated in FIG. 8C. The Z3 $\lambda/4$ transmission line, connecting the end of Z2, may merge with the other nine identical lines at the center. In another path, the $\lambda/2$ transmission line Z4 may connect the end of Z2 and may go to the 50Ω terminator 84014.

The $\lambda/2$ transmission line Z4 broadband technique may be implemented in the example 10-way divider design. The example divider may provide greater than 28% bandwidth centered at 900 MHz.

In another embodiment, a high density SSHPA design (PAU) may reduce overall profile and increase overall power density. A T-Plate structure may be used with three significant planes—two opposite horizontal planes to mount power devices and one vertical plane to interface to a cooling plate. The structure may double power density as compared to a conventional layout architecture, minimizing the power amplifier profile. The power amplifier architecture may embed high thermal conductive material between the two horizontal surfaces. This may effectively transfer their heat onto the vertical plane to interface with the cooling plate. The approach addresses heat transfer issues that all power amplifiers face.

Figure 9:
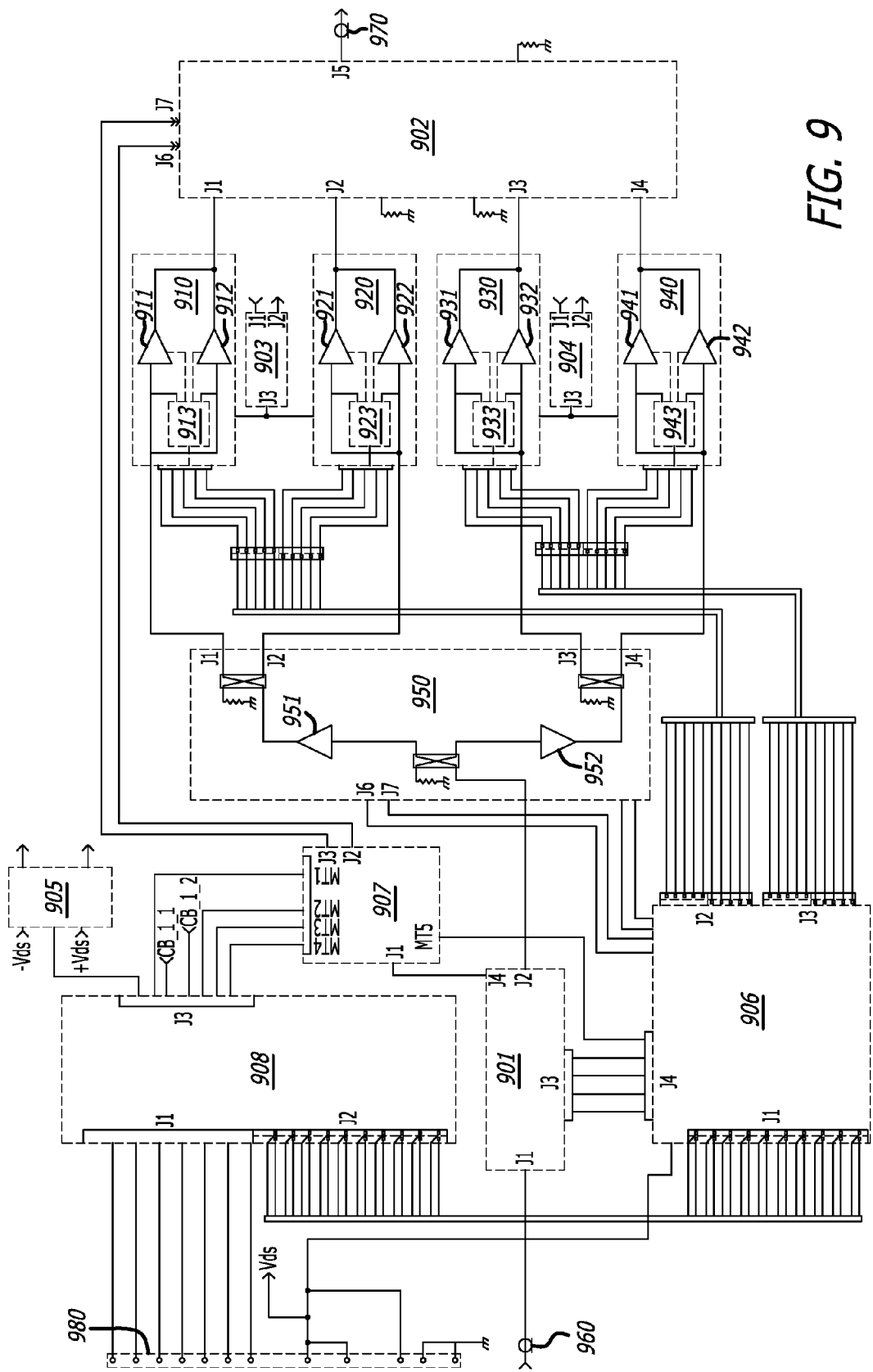
FIG. 9 is a block diagram of an example of a 5 kW compact pulse radar power amplifier with monitor, control, and protection features operating in low L-Band.

FIG. 9 is a block diagram of an example of a 5 kW compact pulse radar power amplifier with monitor, control, and protection features operating in low L-Band. An RF signal of around 5 W may be injected to an input module 901 via an RF input connector 960. The signal may be boosted by amplifiers 951 and 952 and equally divided through a driver/divider module 950 and delivered to four basic amplifier modules (BAM) 910, 920, 930, and 940.

Each BAM may include multiple power devices, such as amplifiers 911 and 912 in BAM 910, amplifiers 921 and 922 in BAM 920, amplifiers 931 and 932 in BAM 930, and amplifiers 941 and 942 in BAM 940 that may each deliver about 700 W peak power and generate significant heat with around 50% efficiency. Each BAM may also include a bias and control module that enables or disables the power device, such as bias and control modules 913, 923, 933, and 943. An output module 902 may sum the four BAM outputs, each delivering greater than 1.25 kW into 5 kW output power at an output 970.

There may also be capacitor banks 903 and 904 that store adequate energy to meet pulse operation needs. An interlock 905 may relay DC input Vds to the power devices after ensuring the power pin mate to avoid arching caused by the large inrush current. A DC power distribution module 906 may generate +5V, +3.3V, +20V, −4.1V from input +50V and distributes to the sub-assemblies. A detection module 907 may detect RF input/output and reflected RF at the output. And a controller 908 interfacing via a connector 980 may monitor parameters detected in various sub-assemblies and control the input module 901, interlock 905, and BAMs 910 to 940.

Due to relatively large dimensions of the power devices, such as 1.3"×0.4" each, and other bulky modules, a conventional single surface layout scheme may make it difficult to implement such a system in a small space to deliver hundreds of kW to replace a Klystron radar transmitter.

Figure 10:
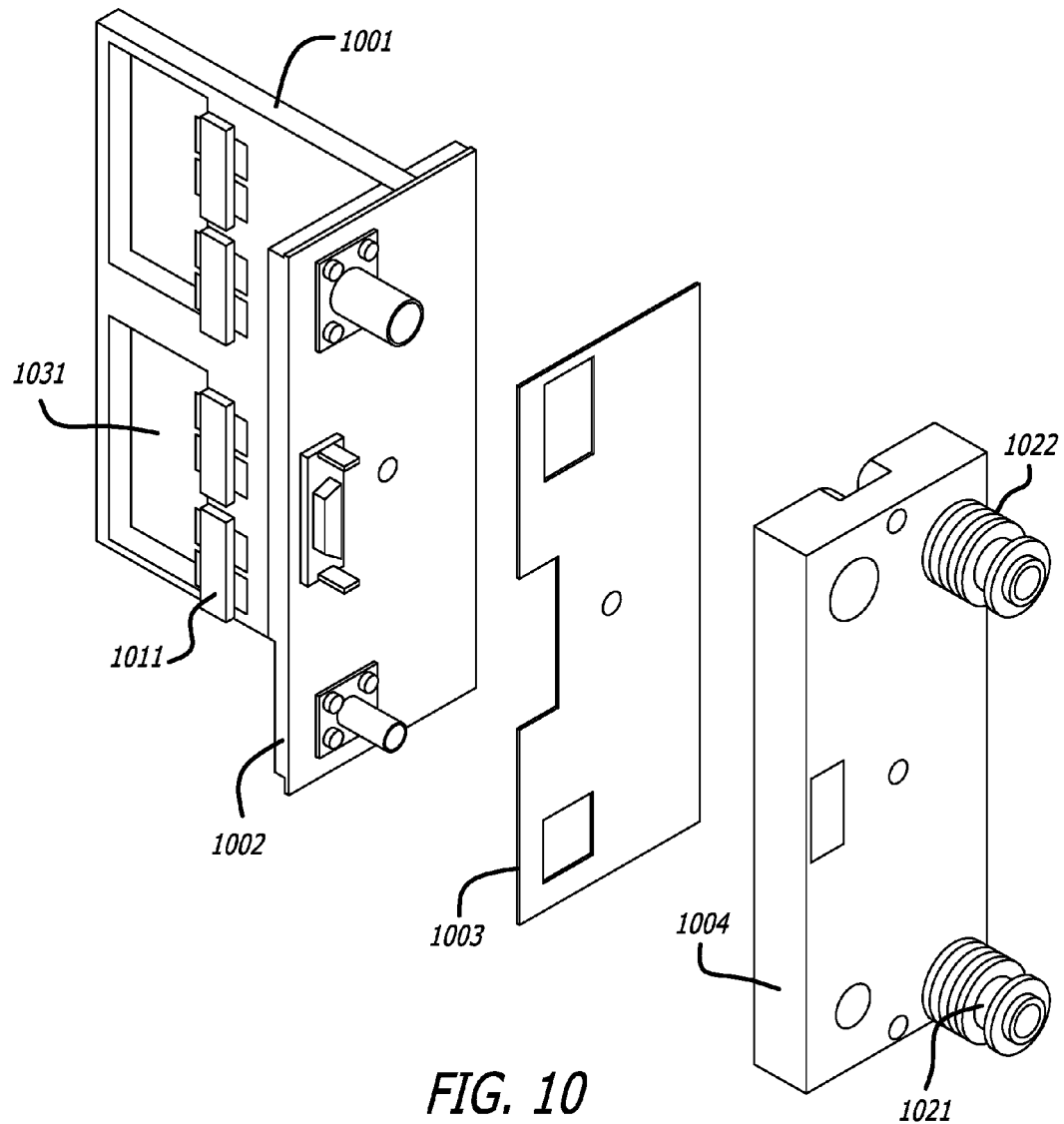
FIG. 10 illustrates an example of a T-plate structure that may be used to compactly contain and cool the components in the compact pulse radar power amplifier shown in FIG. 2.

FIG. 10 illustrates an example of a T-plate structure that may be used to compactly contain and cool the components in the compact pulse radar power amplifier shown in FIG. 2. The T-plate structure may include a horizontal plate 1001 and a vertical plate 1002. The horizontal plate may offer two significant planes on which to mount multiple power devices, such as four on each side, such as the four devices 1011 on the visible side in the drawing.

The vertical plate 1002 may provide thermal removal. The vertical plate 1002 may thermally interface with a water cooling plate 1004 via thermally-conductive interface material 1003. Cooling water or other fluids may be injected in water inlet 1021 and exit after removing heat from water outlet 1022. Cut-outs, such as cut-outs 1031, may be provided to embed bias control modules to minimize the high power interference and to effectively utilize available space that is not in the thermal path.

This T-plate structure may reduce the horizontal surface area by about 50% while, at the same time, doubling the amount of heat per unit area that can be managed. The plates of the T-plate structure may be of any thermally-conductive material, such as metals like Al or Cu. The plates may be part of a unified structure or may be separate pieces thermally connected, such as through brazing or soldering.

Power device junction temperature may determine whether a power amplifier based on a T-plate structure can meet a reliability requirement. The higher the device output power, the greater may be the challenge of removing heat from the devices to the vertical plate 1002.

Figure 11:
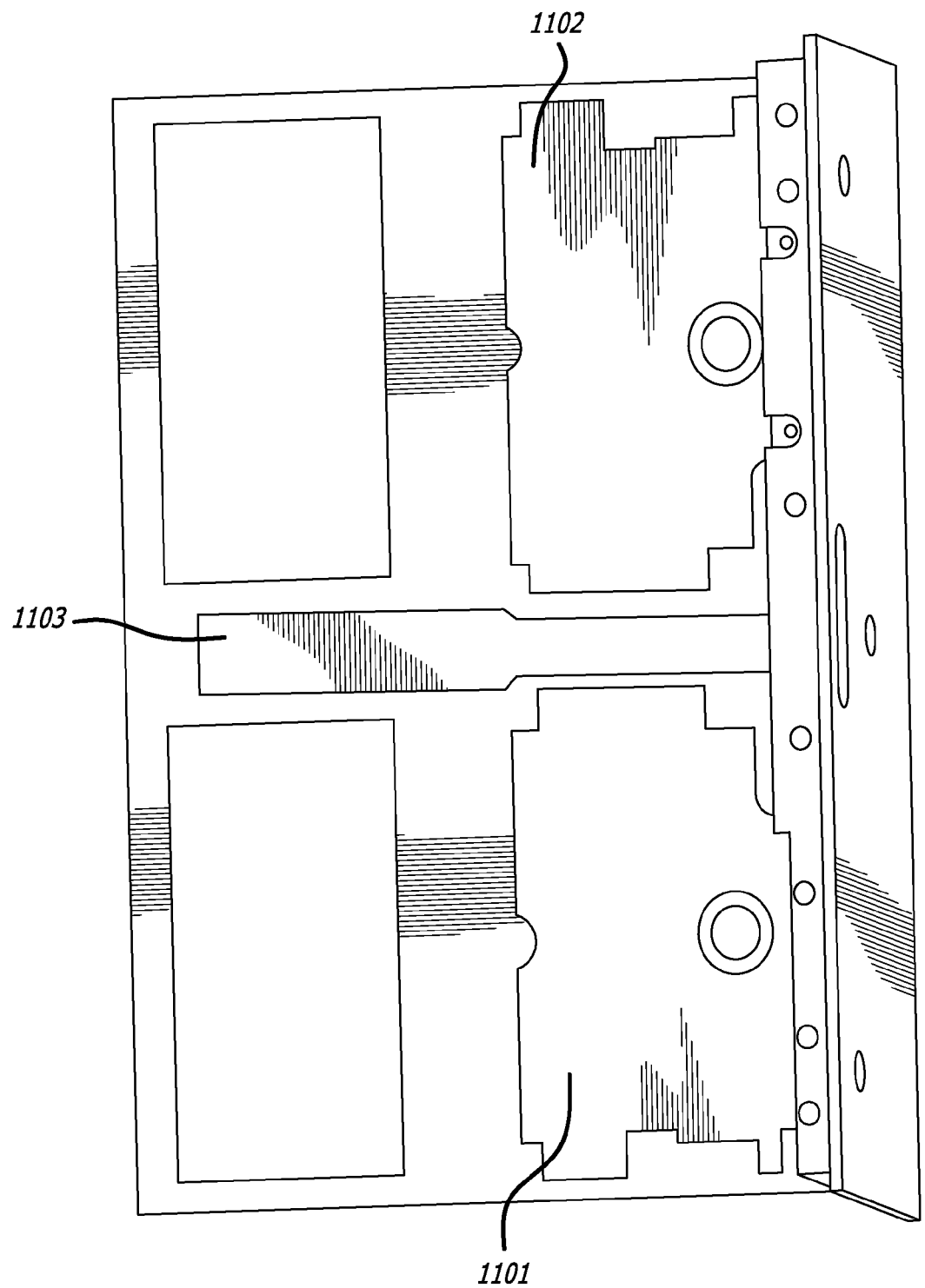
FIG. 11 illustrates an example of high thermally-conductive material that may be embedded in the thermal path of a T-plate structure to improve thermal conductivity.

FIG. 11 illustrates an example of high thermally-conductivity material 1101, 1102, and 1103 that may be embedded in the thermal path of a T-plate structure to improve thermal conductivity. The material may be brazed or welded. The material may be of any type, such as copper or a graphite-based material that offers significantly higher thermal conductivity, such as 398 W/k-m or 1500 W/k-m, without increasing the weight dramatically, as compared to conventional aluminum with 167 W/k-m.

Figure 12:
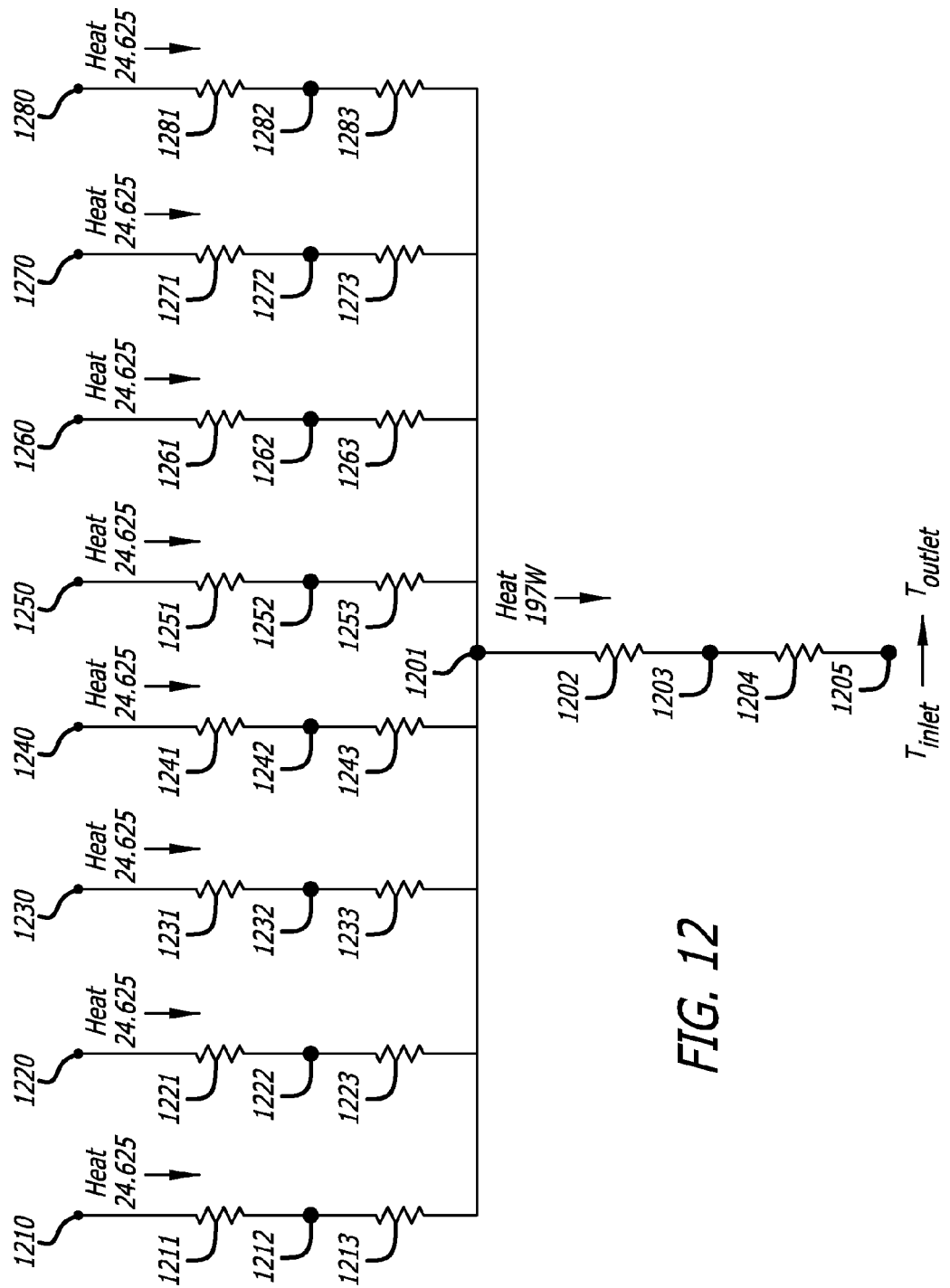
FIG. 12 illustrates an example of a thermal model for the T-plate structure illustrated in FIGS. 10 and 11.

FIG. 12 is an example of a thermal model for the T-plate structure illustrated in FIGS. 10 and 11. The model illustrates all thermal resistances from the bases of the heat-generating devices to the cooling water. The model includes temperatures at junctions 1210, 1220, 1230, 1240, 1250, 1260, 1270, 1280 of the power devices, each of which may nominally generate an average heat of about 25 W. The model also includes junction-to-case thermal resistances 1211, 1221, 1231, 1241, 1251, 1261, 1271, and 1281. The model also includes temperatures at the flanges of power devices, like those on the BAMs in FIG. 9, namely flanges 1212, 1222, 1232, 1242, 1252, 1262, 1272, and 1282. The model also include the case-to-horizontal surface thermal resistances 1213, 1223, 1233, 1243, 1253, 1263, 1273, and 1283.

The junction 1201 represents the temperature at the device center line between devices on two parallel horizontal surfaces. The thermal resistance 1202 represents thermal resistance from the center line of the devices to the T-plate joint, represented by junction 1203. This may be the most critical resistance due to a total thermal path (longest traveling distance) of about 1.9" in the example. The thermal resistor 1204 represents cooling plate resistance from the interface to the cooling liquid. For the 1202 thermal resistance, $$R = \frac{L}{KA} \quad (11)$$

where L is the travelling distance of the generated heat in (m), A is the cross area in (m$^2$) of the thermal media, and K is the thermal conductivity in (W/m–K). The embedded material's effective dimensions in the example are L=1.9" W=5.6", H=0.225", $$L=1.9"=0.04826(m) \quad (12)$$

$$A=5.6*0.225(in^2)=0.0008(m^2) \quad (13)$$

So, $$R = \frac{60.325}{K}(°C./W) \quad (14)$$

In the example amplifier, the embedded material may be a graphite-based material that has 1500 W/m–K thermal conductivity.

$$R_{Graphite} \le 0.04(°C./W) \quad (15)$$

The temperature increase through 1.9" distance with total of 197 W heat $$\Delta T_{Graphite}=7.88(°C.) \quad (16)$$

The following table sets forth characteristics of various materials, including Al and Cu, with 167 (W/m–K) and 398 (W/m–K) conductivity, respectively:

| Parameter | K (W/m-K) | R (° C./W) | ΔT (° C.) @ 197 W Heat | D (g/cc) |
|---|---|---|---|---|
| Graphite Based Material | 1500 | 0.04 | 7.88 | 2.26 |
| Cu-110 Alloy | 398 | 0.15 | 29.86 | 8.32 |
| 6061-T6 | 167 | 0.36 | 70.92 | 2.79 |

The thermal removal capacity of graphite-based material may be superior to Cu and Al, such as 3.8 times better than Cu and 9 times that of Al. Its weight may be lighter than Al and may be significantly lighter than Cu (3.7 times lighter). The detailed material selection may be dominated by specific amplifier requirements, including reliability. In the example amplifier with 197 W average heat, the 22° C. junction temperature improvement from graphite-based material to Cu alloy may double the reliability of the power devices.

When using a T-plate structure, all power devices may be laid onto two horizontal planes symmetrically to achieve uniform thermal characteristics among them. The divider/driver module 950 and the output module 902 in FIG. 9 may be configured to interface horizontally with the basic amplifier modules 910, 920, 930, and 940 with minimum space occupied and interconnection power losses. Details are shown in FIGS. 13, 14, 15, and 16.

Figure 13:
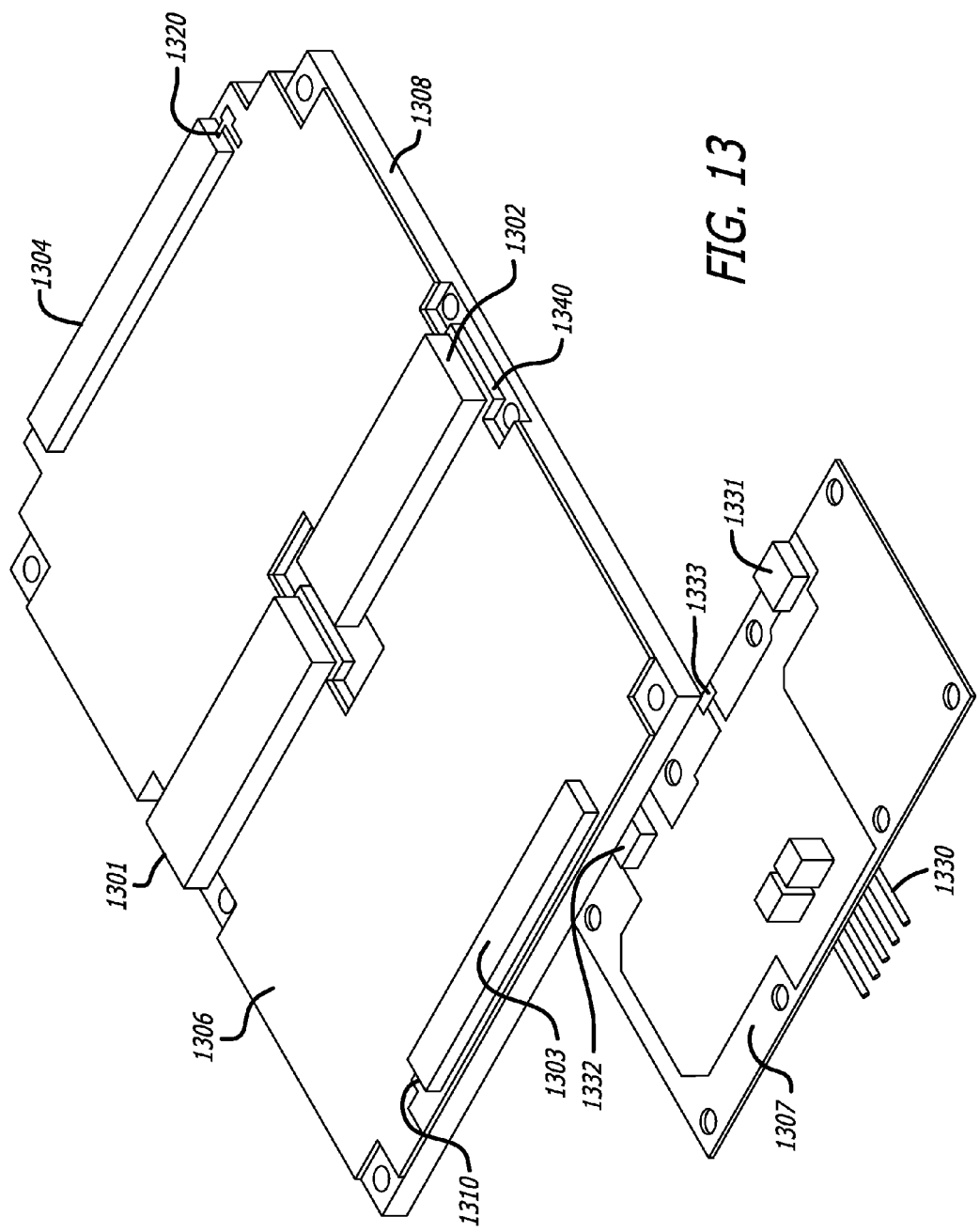
FIG. 13 illustrates an example of a layout that may be used for each basic amplifier module (BAM) that may provide an output of at least 1.25 kW.

FIG. 13 illustrates an example of a layout 1306 that may be use for each basic amplifier module (BAM). The layout is for two power devices 1301 and 1302. The layout 1306 may be constructed with minimum thermal resistances and with a horizontal input port 1310 and an output port 1320. To minimize thermal resistance, the power devices 1301 and 1302 may be soldered to a carrier 1308. Space saving baluns 1303 using 0.047" OD coax and 1304 using 0.086" OD coax may be in a combining scheme to shorten the thermal path. The bias and control modules 913, 923, 933, and 943, shown in FIG. 9 as module 1307, may be embedded underneath the input matching layout to further minimize size and to shield out high power interference, with connector 1330 interfacing with the DC power distribution module 906. Temperature sensors 1331, 1332, and 1333, may be mounted under the power devices 1301 and 1302 and the carrier 1308, and may report device and base plate temperatures.

Figure 14:
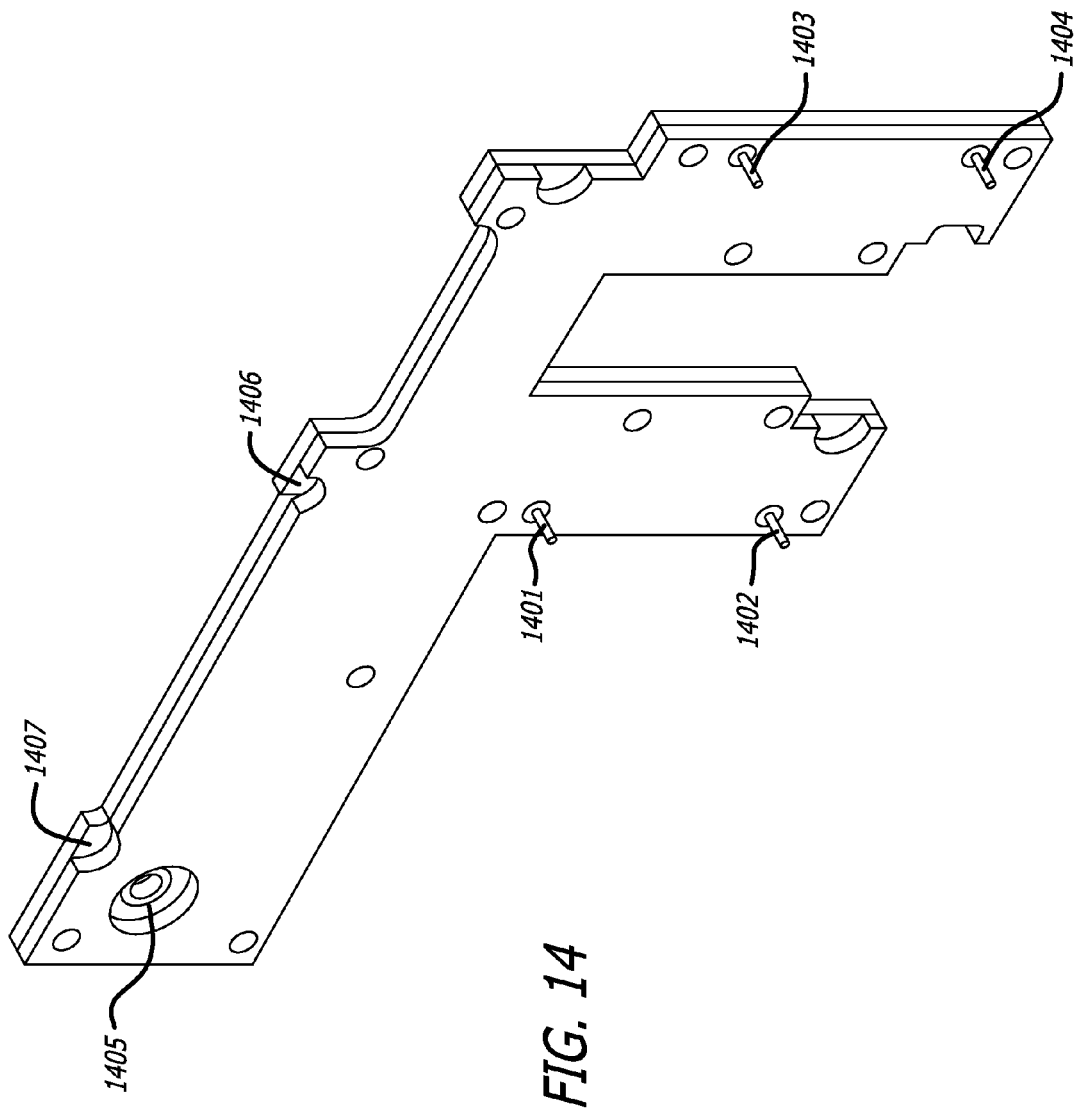
FIG. 14 illustrates an example of a compact high power combiner module with RF interfaces perpendicular to the layout plane and may also provide forward/reflected power coupling functions.

FIG. 14 is an example of a compact high power combiner module with RF interfaces perpendicular to the layout plane and which may also provide forward/reflected power coupling functions. The output module 902 in FIG. 9 may include a 4-way combiner and directional coupler, configured as shown in FIG. 14. Input ports 1401, 1402, 1403, and 1404 may be perpendicular to the circuit layout plane so that they can directly interface with 4 BAMs, without cabling to minimize power loss and space, as shown in FIGS. 16A and 16B.

Figure 15:
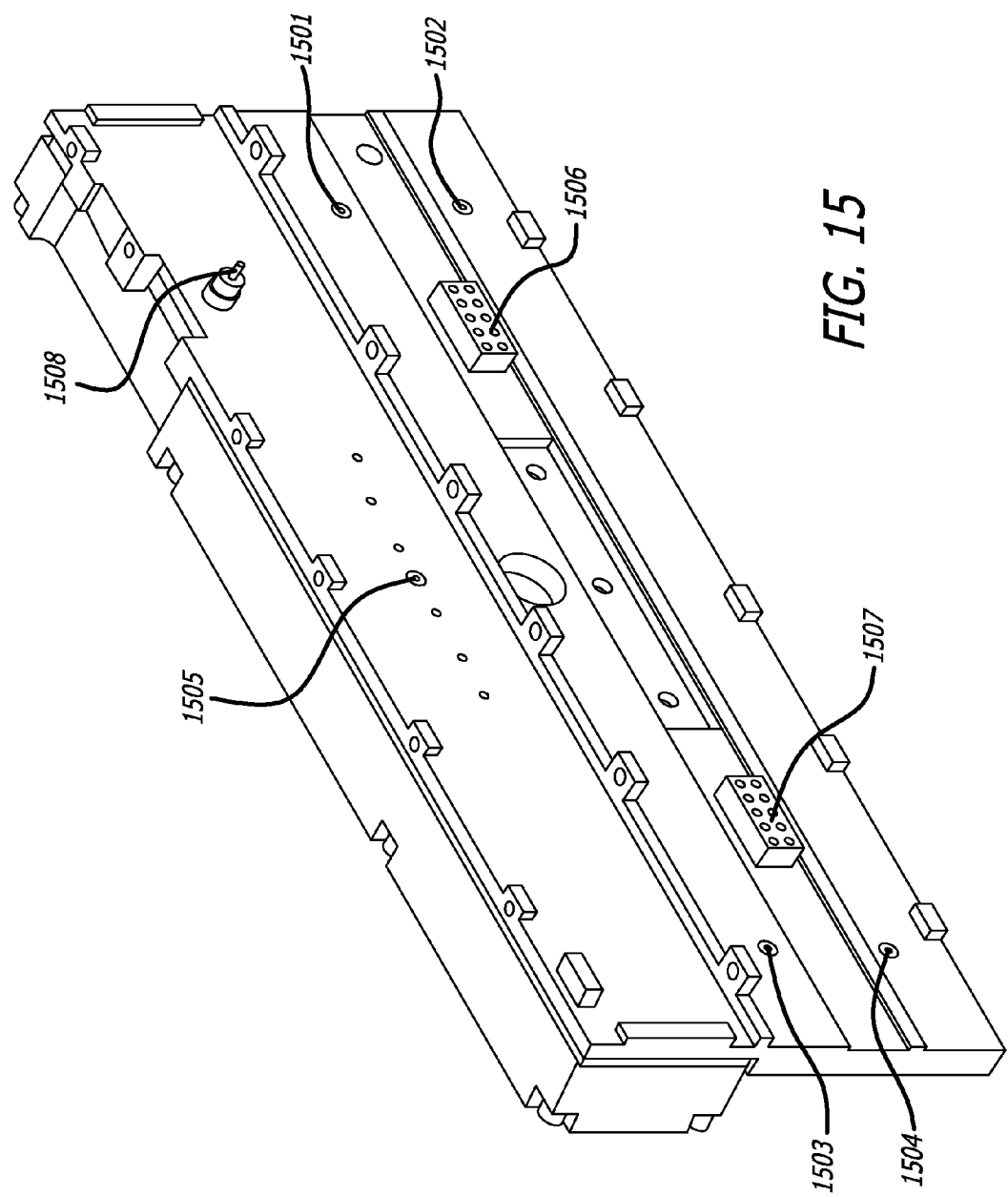
FIG. 15 illustrates an example of a compact driver/divider with RF interfaces perpendicular to a layout plane, and includes DC distribution, controls, driver amplification, and divider circuitry.

FIG. 15 is an example of a compact driver/divider with RF interfaces perpendicular to layout plane, and includes DC distribution, controls, driver amplification, and divider circuitry. It may use the same design approach as used in the driver/divider module 950 and the DC power distribution module 906 in FIG. 9. RF ports 1501, 1502, 1503, and 1504 may directly interface with BAM input ports. The connectors 1506 and 1507 may directly interface with bias and control modules providing bias and enable to the BAMs and receive temperature monitor signals from BAMs. The divider may also include RF input 1505 and DC input 1508.

Figure 16A:
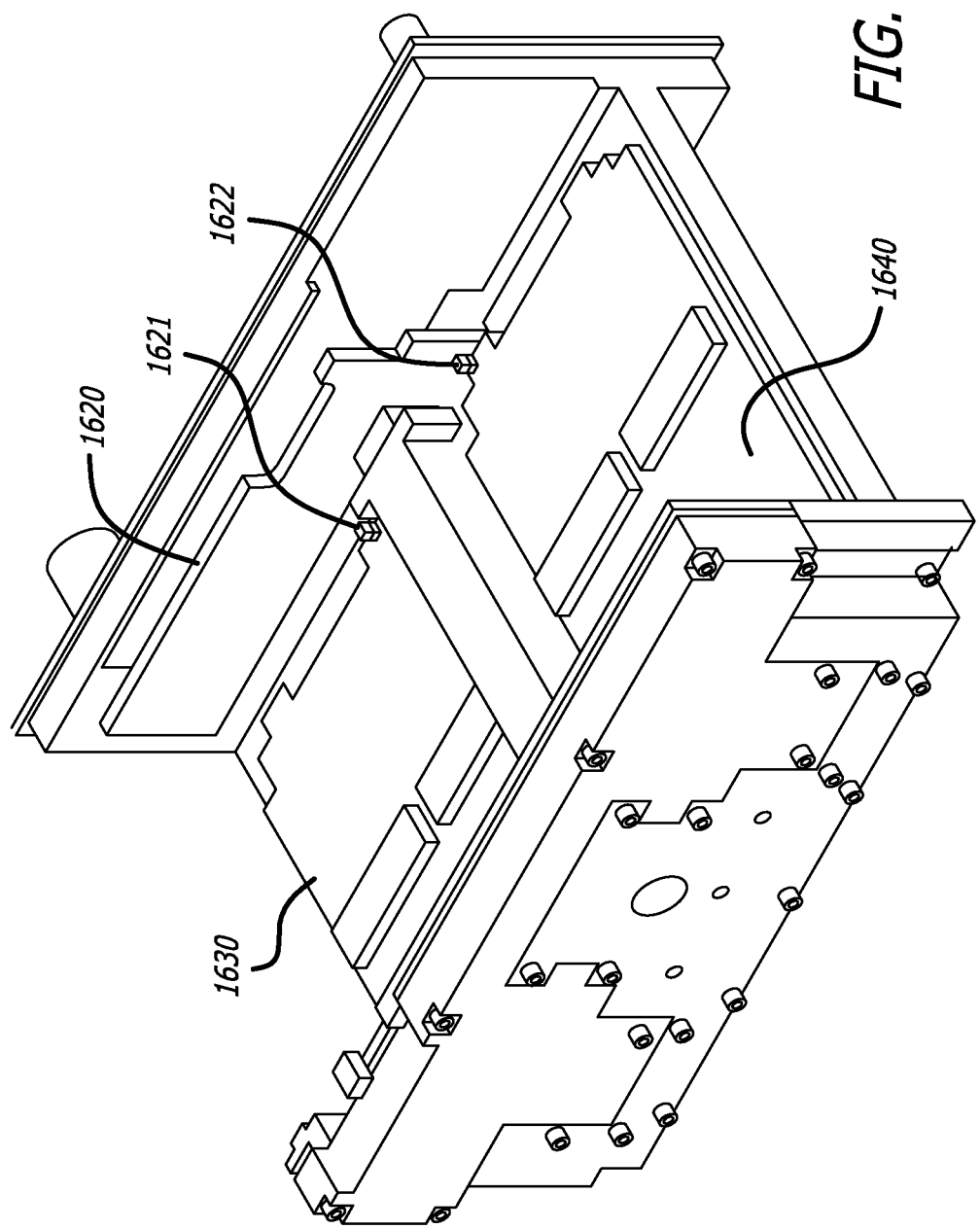
FIGS. 16A and 16B are an example of different views of direct interfaces between a driver/divider module and BAMs, as well as direct interfaces between an output module and BAMs. The BAMs may amplify their respective inputs and each delivers 1.25 kW.
Figure 16B:
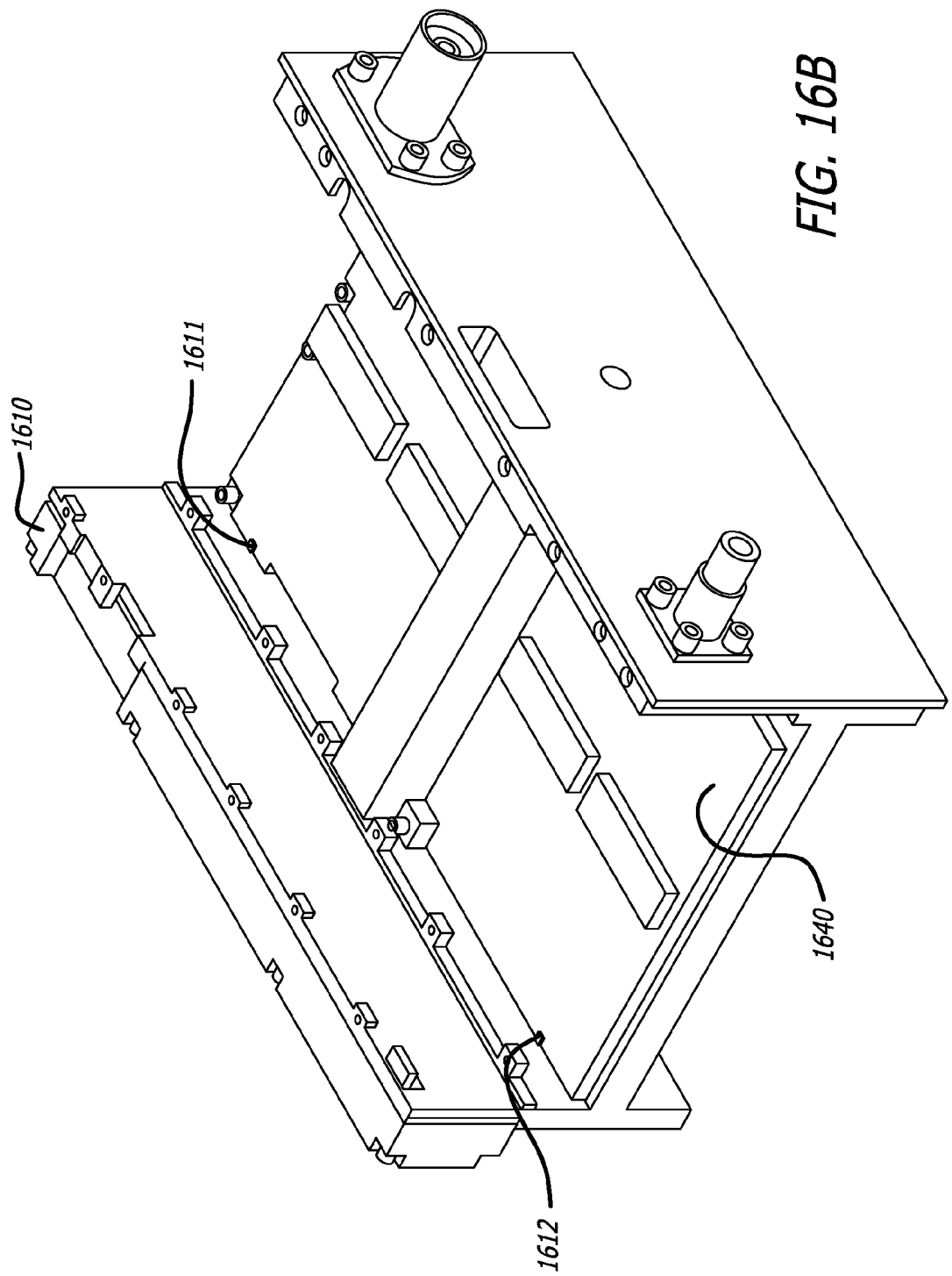

FIGS. 16A and 16B are an example of different views of direct interfaces 1611 and 1612 between a driver divider module 1610 and BAMs 1630 and 1640, as well as direct interfaces 1621 and 1622 between output module 1620 and BAMs 1630 and 1640. Each BAM, like BAM 1630 or 1640, may amplify its input and delivers 1.25 kW to the combiner 1620.

Figure 17:
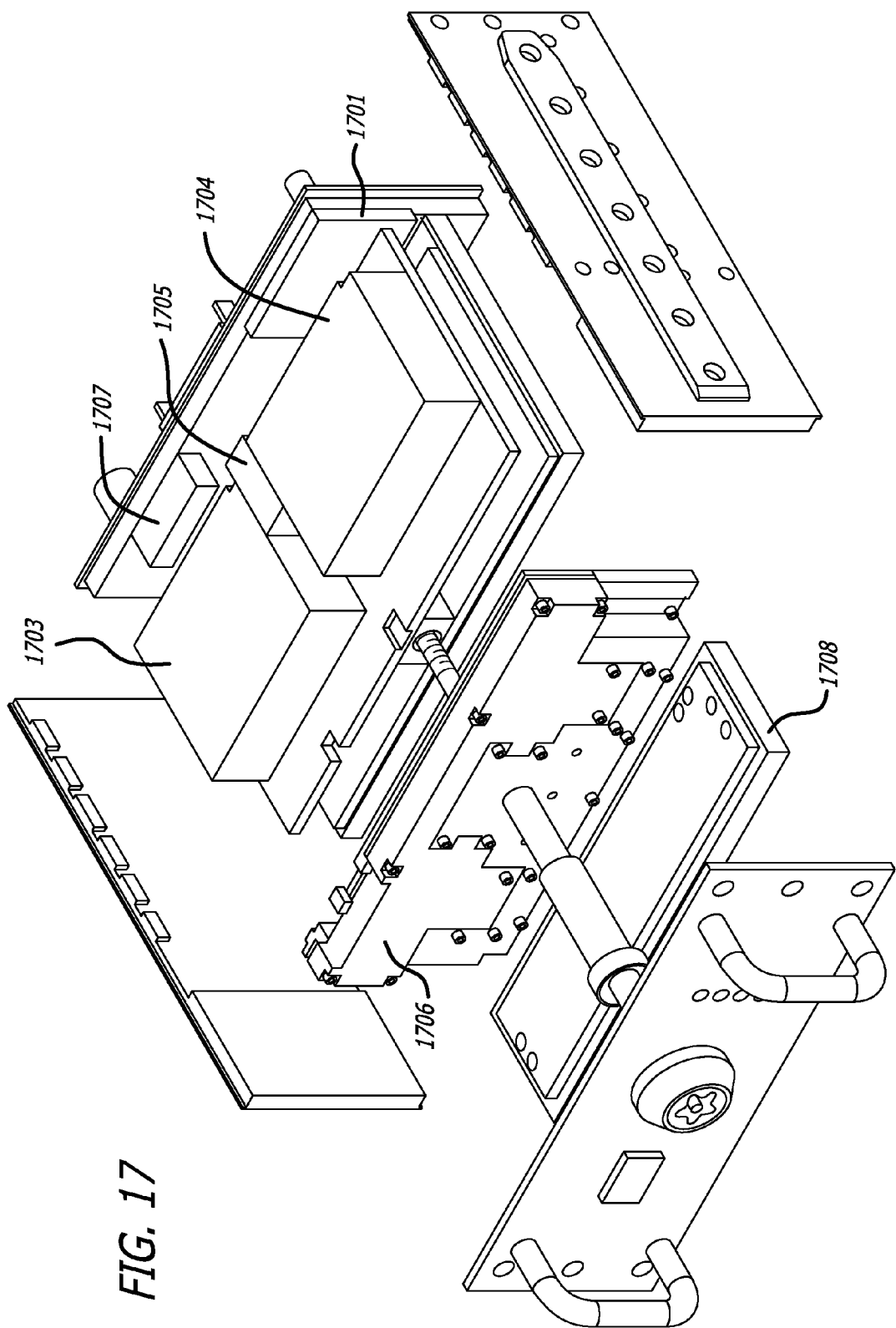
FIG. 17 is an exploded view of an example of a 5 kW compact high power amplifier that uses a T-plate structure in a compact design.

FIG. 17 is an exploded view of an example of a 5 kW compact high power amplifier that uses a T-plate structure in a compact design. This design may provide great space-saving advantages. An input module 1701 may be attached to a vertical plate. Capacitor banks 1703 and 1704 may directly interface with BAMs, an interlock module 1705, a DC distribution module 1706, a detector module 1707, and a controller module 1708 utilizing a T-plate structure.

Figure 18:
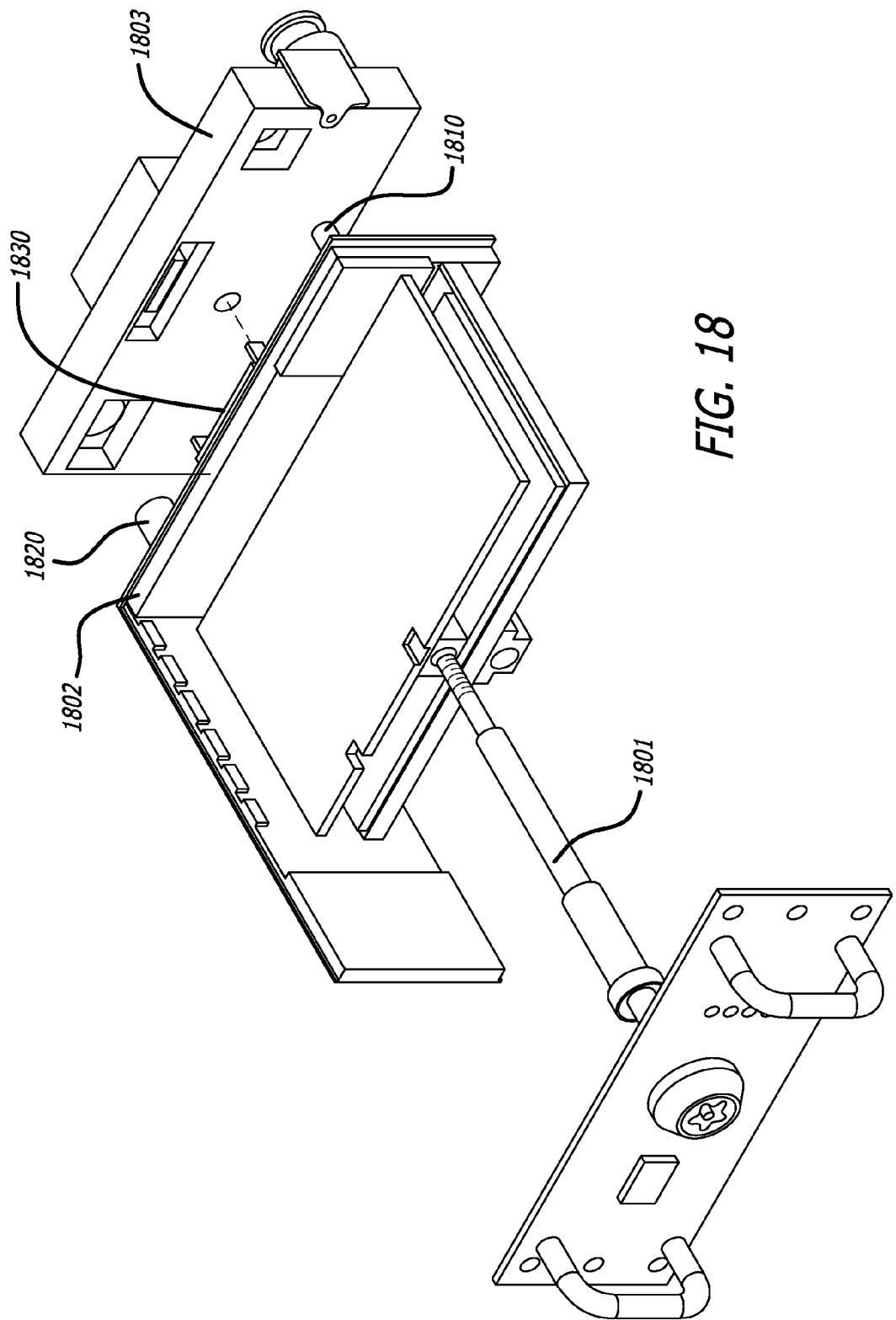
FIG. 18 illustrates an example of a solid state amplifier, a cooling plate, and a single bolt that may be used to easily attach and detach them from one another.

FIG. 18 illustrates an example of a solid state amplifier, a cooling plate 1803, and a single bolt 1801 that may be used to easily attached and detach them from one another. In addition to utilizing space effectively, the T-plate structure may minimize the vertical plane surface area, thereby allowing the single bolt 1801 to attach the solid state amplifier to the cooling plate. The single bolt 1801 may be ¼"-20 and may provide significantly more than 700 lbs clamping force to seamlessly attach a vertical plate 1802 of the amplifier to the cooling plate 1803 to ensure minimal thermal resistance. Blind mate connectors may be used for RF input 1810, RF output 1820, and DC/interface 1830, thus allowing the amplifier to be hot swappable.

Figure 19:
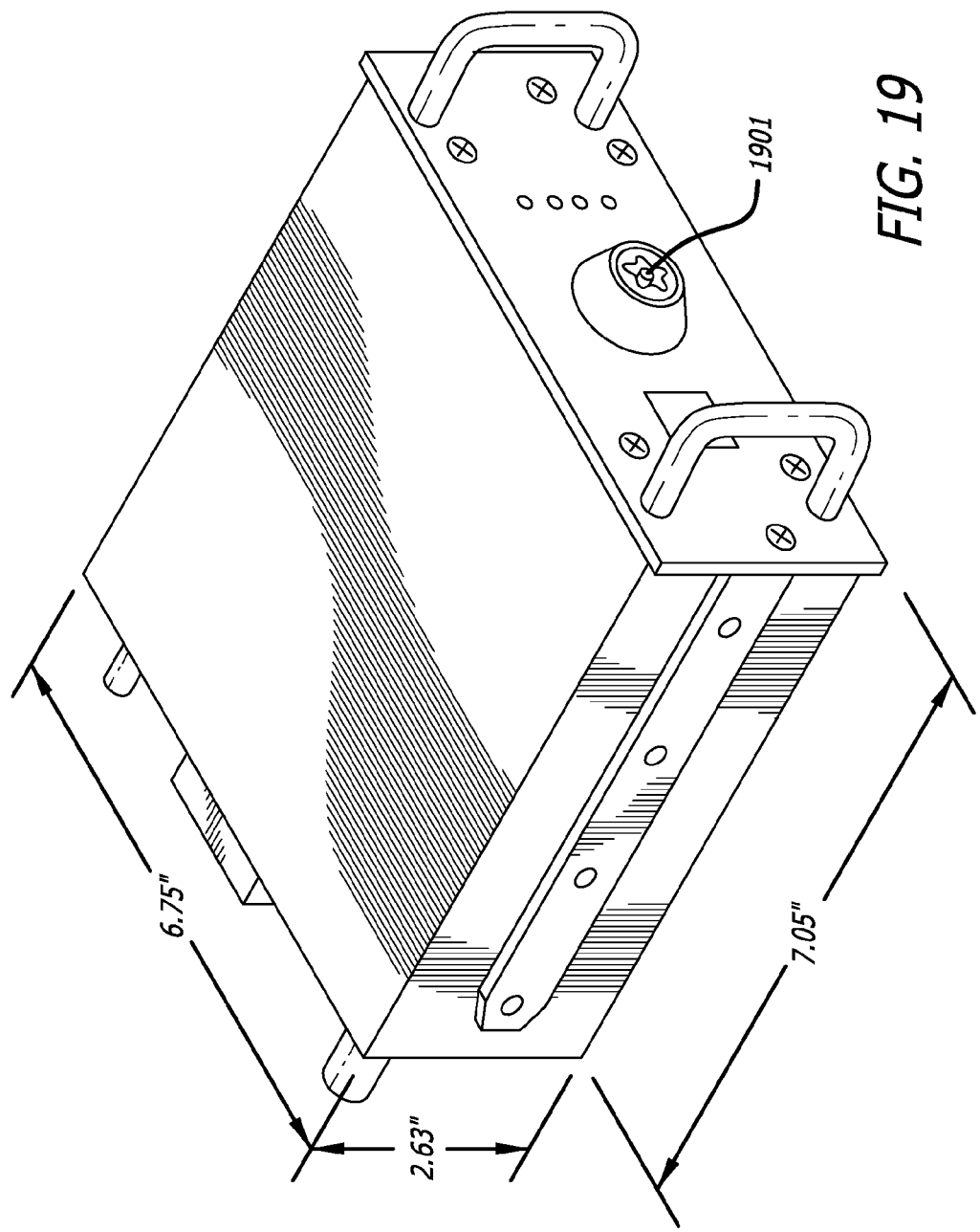
FIG. 19 illustrates an example of a fully assembled 5 kW compact high power amplifier utilizing a T-plate structure.

FIG. 19 illustrates an example of a fully assembled 5 kW compact high power amplifier utilizing a T-plate structure. The amplifier may operate with a nominal duty cycle of 3.8% and up to 6% under pulsed conditions for radar applications. The amplifier may include parametric monitors, including RF in, RF out, VSWRs, temperatures, voltages, and currents. The amplifier may provide adjustments, such as for gain and phase, and include online and standby controls, and protections that may include over-voltage, over-current, over-temperature, and high VSWR. The amplifier architecture may enable a high power HPA with near 40 W/in$^3$ power density and hot swapping using a ratchet 1901 accessible from its front face.

Features of the T-plate structure may include:

A solid state amplifier (SSA) may utilize a T-plate structure that includes three significant planes, with two opposite horizontal planes each having power devices mounted on them, and one vertical plane to interface with a cooling plate for the removal of heat with the heat traveling from the power-generating devices to the vertical plate.

Material with high thermal conductivity may be embedded between the horizontal planes in the thermal propagation path to minimize the thermal resistance.

A solid state amplifier may utilize multiple power transistors to achieve high power with high power density and may include multiple basic amplifier modules (BAM). Each BAM may provide mounting for more than one power transistor.

A solid state amplifier may combine multiple BAMs and utilize an output combiner module with input ports perpendicular to the combiner layout to save space and to minimize the loss.

A solid state amplifier may combine multiple BAMs and utilize an input divider module with output ports perpendicular to the divider layout to save space and to minimize the loss.

A solid state amplifier may provide various functional blocks that can be integrated surrounding the T-plate structure using a space-saving layout to minimize the SSA profile.

The vertical plate may have a small profile so that a single bolt may be used to attach the SSA to the cooling plate.

Blind mate RF and DC interface connectors may be used to provide a hot-swappable function.

In yet another embodiment, the liquid cooling system may further reduce the profile of the (m+n)CHPA and thus increase its power density.

Figure 20:
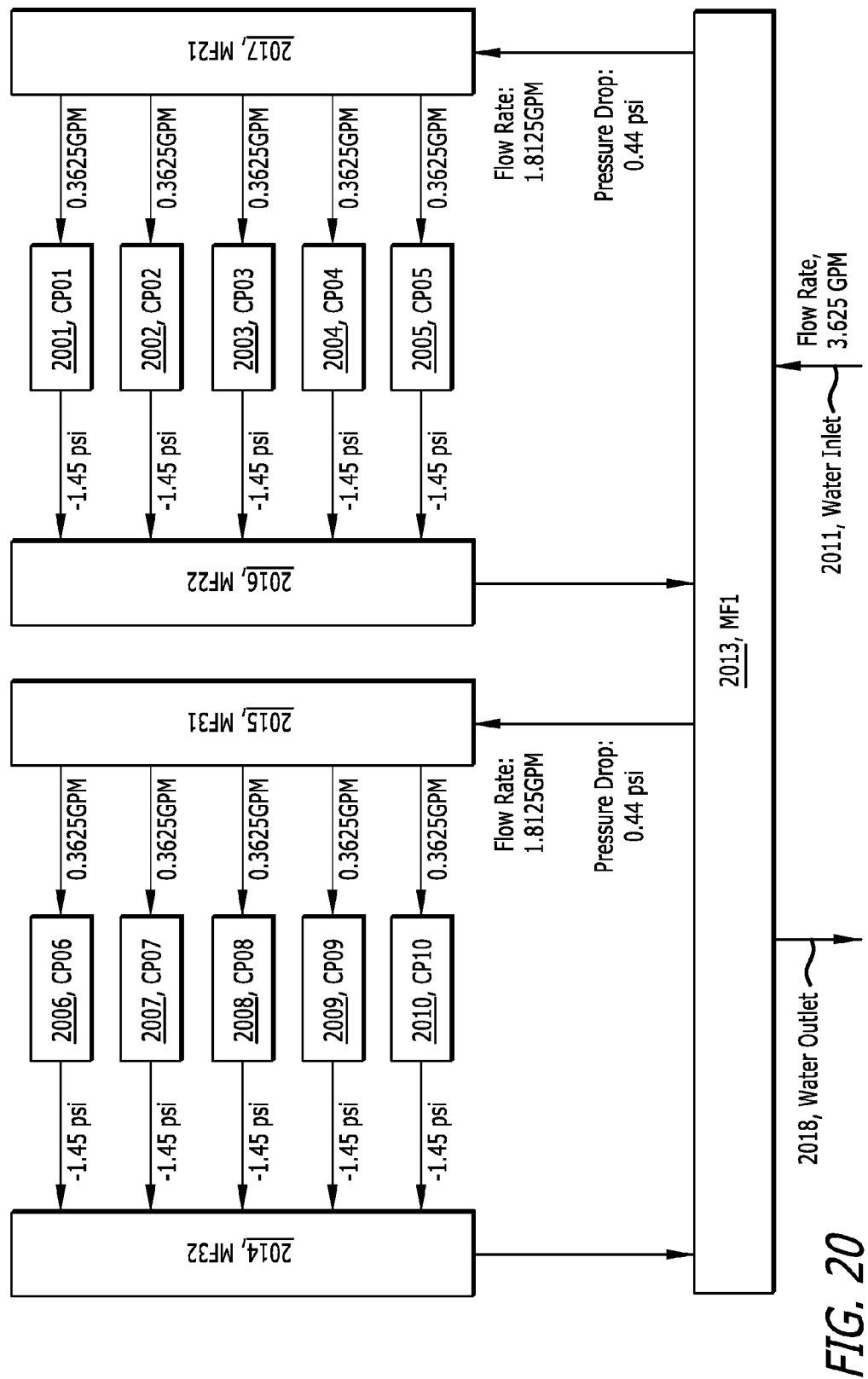
FIG. 20 illustrates an example of a water cooling system for an example (9+1)CHPA, showing liquid cooling distribution from an inlet to ten parallel cooling plates for ten PAUs.

FIG. 20 is an example of a water cooling system for an example (9+1)CHPA, showing liquid cooling distribution from an inlet to ten parallel cooling plates for ten PAUs. Each cooling plate may remove heat from its corresponding PAU independently. The water may flow with a nominal 3.625 GPM rate and 30 psi pressure through a water manifold 2013 via a water inlet 2011. The water manifold 2013 may split the water flow equally between input manifolds 2017 and 2015 and cause very little pressure drop, such as only 0.44 psi. The input manifolds 2017 and 2015 may be identical and each structured so that a 1.8125 GPM flow is uniformly split into five 0.3625 GPM outputs with negligible pressure drop. All ten cooling plates 2001 to 2010 may be parallel to one another so that a specific PAU's thermal behavior will not be affected by others. The cooling plates may be vacuum-brazed with machined fins on base technology with a 6"×1.25" effective thermal removal area. This may ensure 0.3625 GPM to adequately remove the heat from a 5 kW PAU with ~40% power efficiency at a maximum duty cycle, as shown in FIG. 19. Manifolds 2016 and 2014 may be symmetrical to input manifolds 2017 and 2015, respectively, to regulate the return water to the water manifold 2013 and then exiting a water outlet 2018.

Figure 21A:
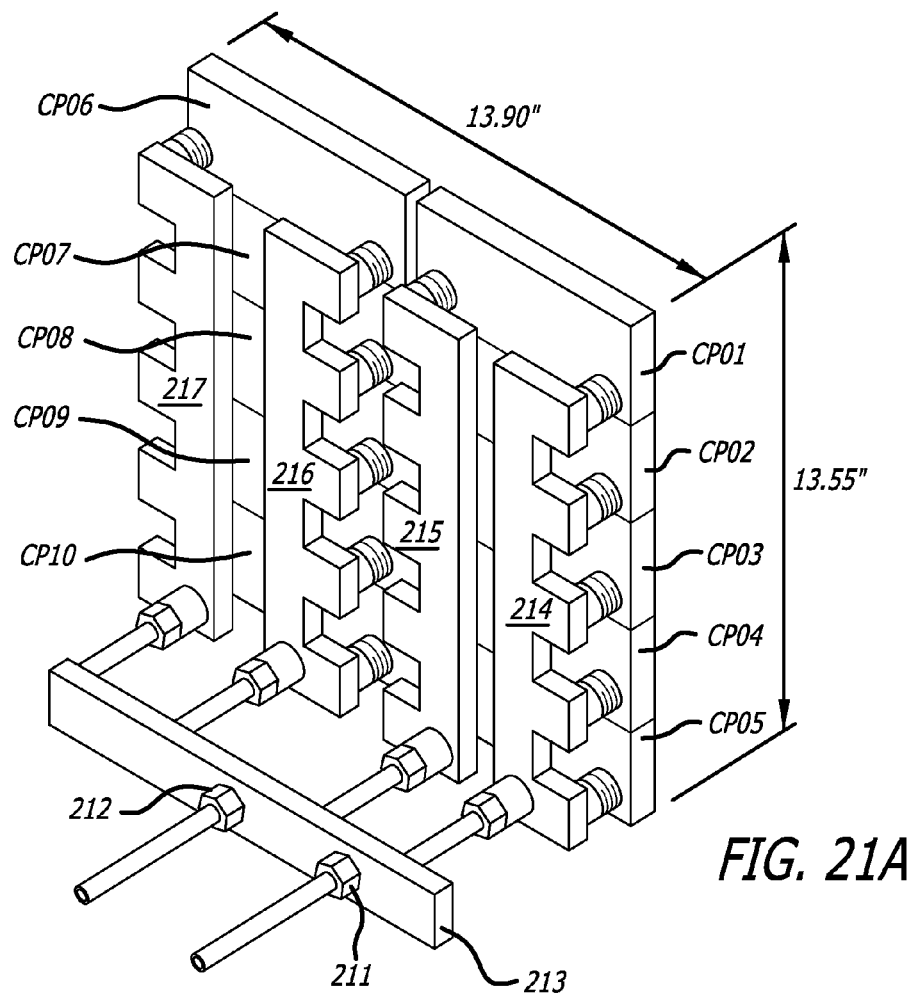
FIG. 21A illustrates an example of a water cooling system for a (9+1)CHPA, that includes manifolds and cooling plates.

FIG. 21A illustrates an example of a water cooling system for a (9+1)CHPA that includes manifolds 2114-2117 and cooling plates CP01-CP10. Manifolds 2114-2117 may distribute cooling water equally to the ten cooling plates CP01 to CP10. The cross surface dimensions of CP01 may be the same as those in the PAU shown in FIG. 19

Figure 21B:
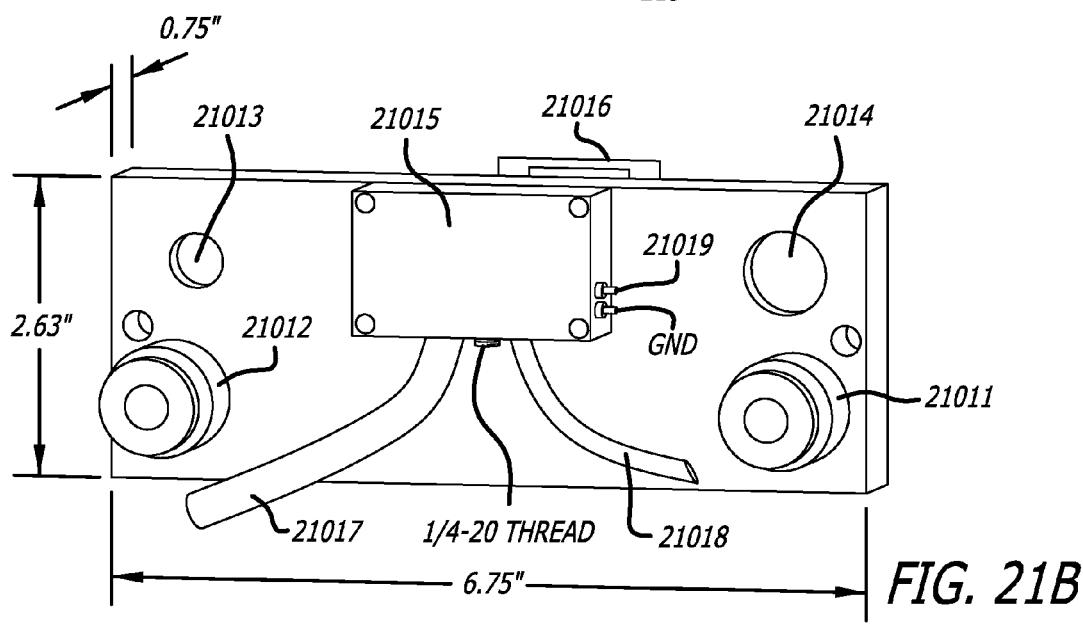
FIG. 21B illustrates an example of the cooling plate CP01 illustrated in FIG. 21A and shows how PAUs may electrically interface with a DIV/COM assembly, power supply bank (PSB), and interface control unit (ICU).

FIG. 21B illustrates an example of the cooling plates CP01 illustrated in FIG. 21A and shows how PAUs may electrically interface with a DIV/COM assembly, power supply bank (PSB), and interface control unit (ICU). The others may be the same. Bellows 21011 and 21012 may connect the manifold and the cooling plate, while providing various tolerances in the PAUs and the CHPA card cage assembly. Through holes 21013 and 21014 may be for barrels (like RF barrels 3012 and 3022 in FIG. 3) on the DIV/SCU assembly to penetrate and mate with PAU's RF input and output ports. A micro-D connector 21016 on the far side may mate with the one on a PAU to supply +50V from a PSB via a cable 21017, and to communicate with an ICU via a cable 21018. When the shaft of a PAU attaches the PAU to the cooling plate with >30 in/lb torque, the position switch in a compartment 21015 may send its control signal to its RF switch, such as to RF switch 2601 in FIG. 2, via a pin 21019.

Figure 22A:
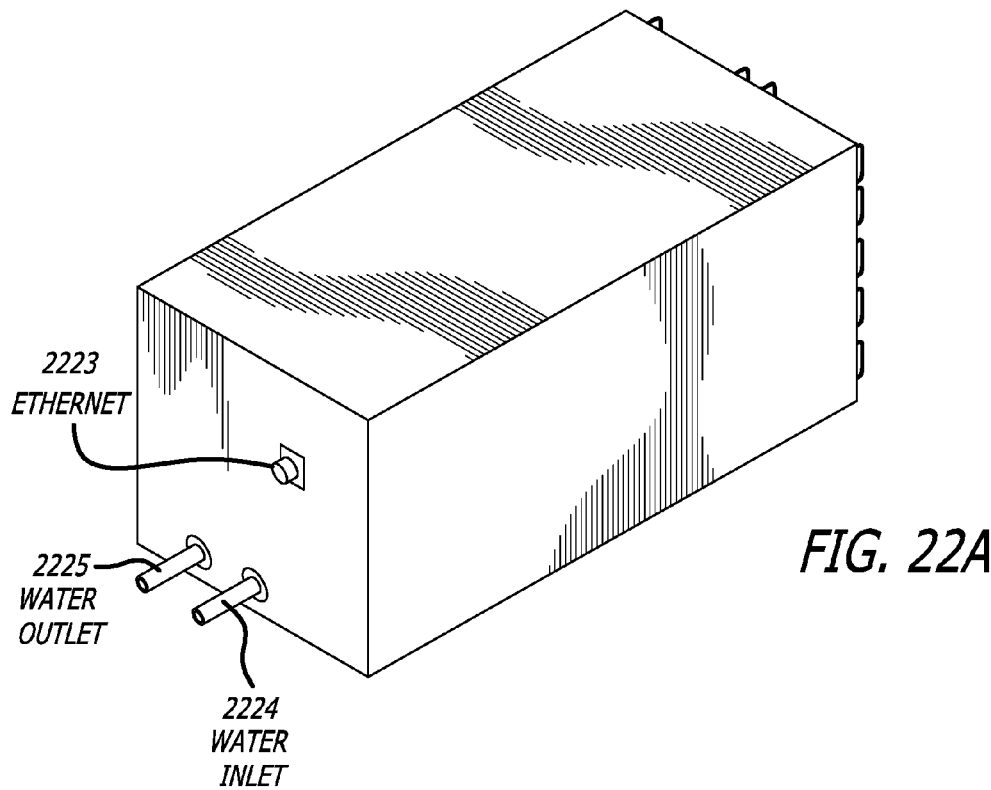
FIGS. 22A and 22B illustrate different views of an example of a compact, modular 40 kW (9+1)CHPA with electrical and thermal interfaces.
Figure 22B:
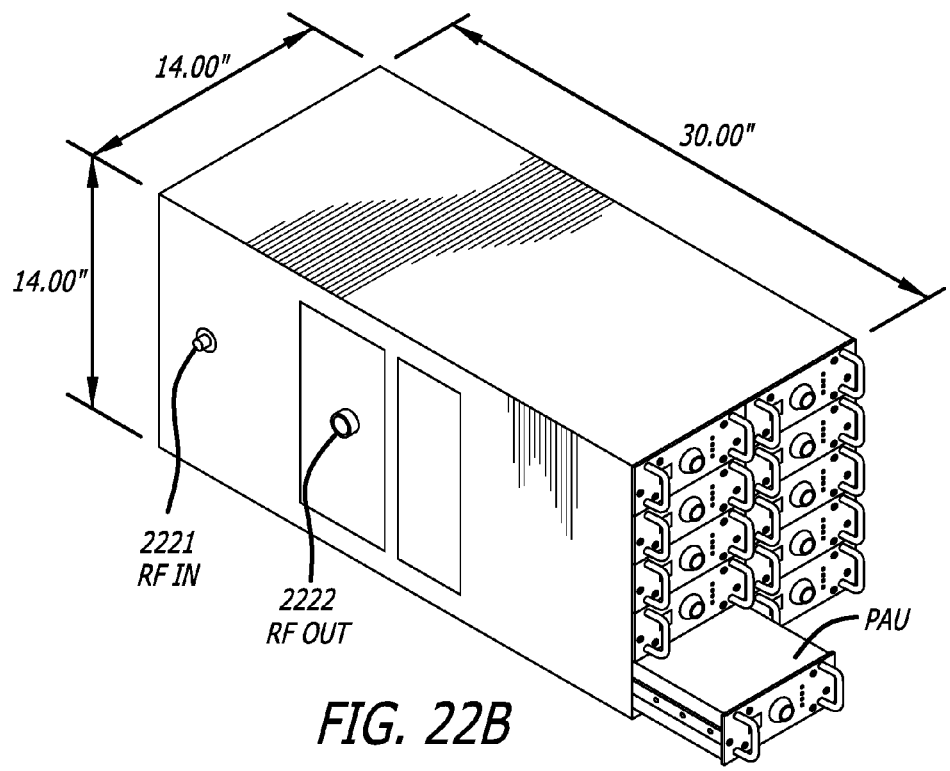

FIGS. 22A and 22B illustrate different views of an example of a compact, modular 40 kW (9+1)CHPA with electrical and thermal interfaces. Electrical and thermal interfaces are identified in FIGS. 22A and 22B. They may include a TNC RF input 2221, a 7/16 DIN RF output 2222 specially designed to handle 40 kW peak power, an RJ-45 Ethernet interface 2223, a water inlet 2224, and a water outlet 2225.

Figure 23:
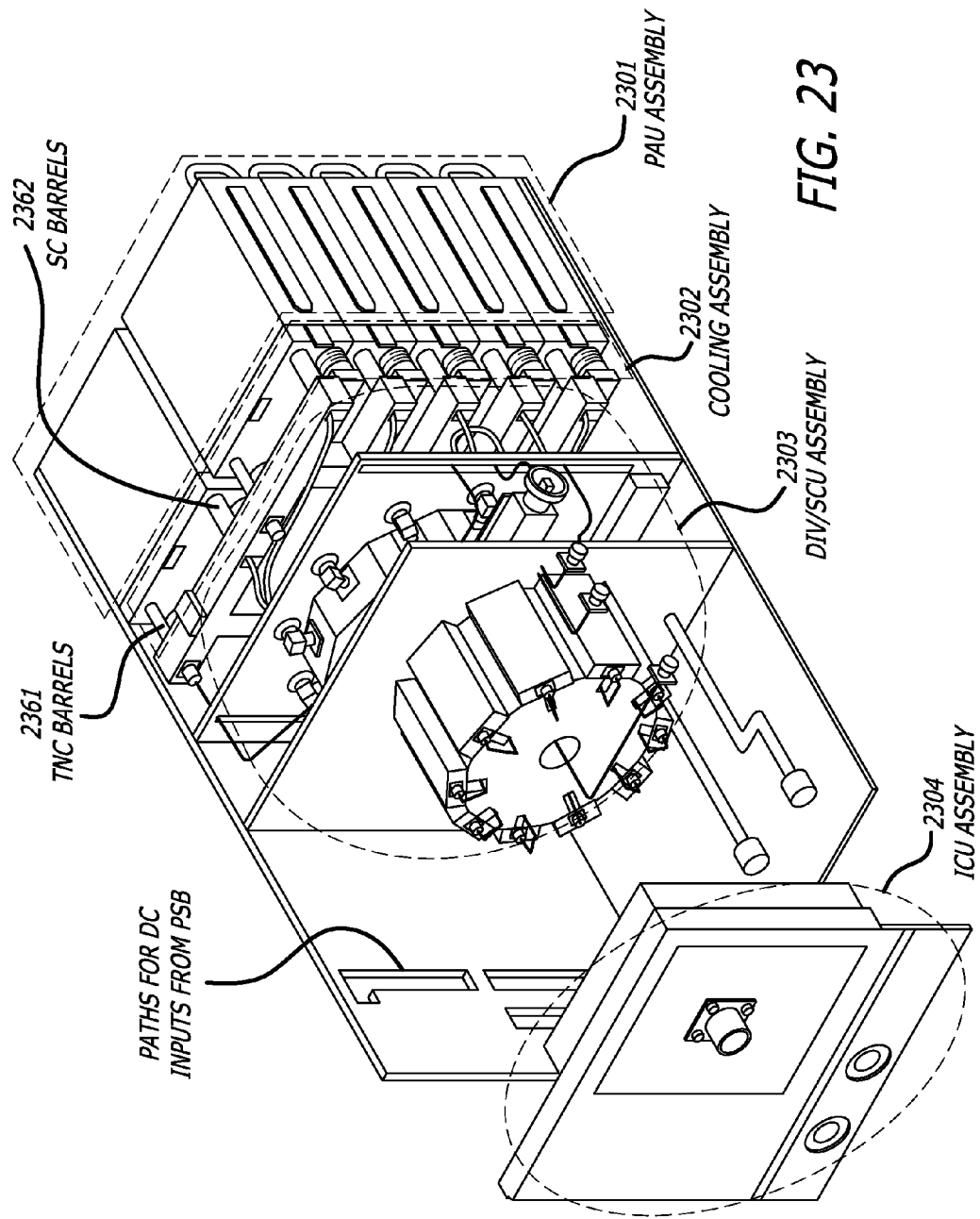
FIG. 23 illustrates a cut away and partially exploded view of the CHPA illustrated in FIGS. 21A and 21B and illustrates the integration of multiple assemblies, like PAUs, a cooling assembly, a DIV/SCU assembly, and an ICU assembly.

FIG. 23 illustrates a cut-away and partially exploded view of the CHPA illustrated in FIGS. 21A and 21B and illustrates the integration of multiple assemblies, like PAUs, a cooling assembly, a DIV/SCU assembly, and an ICU assembly.

This (9+1)CHPA may reliably deliver 40 kW peak power. Multiple (m+n)CHPAs can be conventionally combined to provide a >100 s kW peak power scalable solid state coherent radar transmitter, while still providing outstanding SSTx reliability and life cycle.

DC supplies to the CHPA assembly (not shown in these figures) may be provided. The CHPA card cage assembly may enclose PAU assembly 2301 with 10 PAUs in the front, a water cooling assembly 2302 to which the PAUs may be attached, a divider/switching combiner unit assembly (DIV/SCU) 2303 which may be interconnected with the PAUs via 10 pairs of TNC barrels and SC barrels, each like 2361 and 2362, respectively, and an ICU 2304 in the back.

The following Table 3 illustrates possible major performances of the example (9+1)CHPA utilizing the configuration that has been discussed.

TABLE 3

Specifications for the (9 + 1)CHPA that may be achieved

| Parameter | | Value | Comments |
|---|---|---|---|
| 1. | Electrical Performance | | |
| .1 | Operating Frequency | 850-942 MHZ | Minimum, Upper and Lower −1dB Point |
| .2 | RF Output Power, peak | 75.64 dBm/ 76.64 dBm | Min/Max, 36.6 kW/ 46.1 kW; 1 dB Variation |
| .3 | RF Input Power, peak | 49.0 dBm (80 W) | Nominal, +/−0.5 dB |
| .4 | Spurious Output | 60 dBc | Minimum, from 962-1212 MHz |
| .5 | Harmonic Output | 30 dBc 2nd, 40 dBc 3rd-5th | Minimum |
| .6 | Input/output VSWR | 1.5:1 | Maximum |
| .7 | Output VSWR Survival | 2:1 | Minimum, all phase |
| .8 | Pulse Width | 2-64 μsec | AV1: 32 uS max; AV2: 50 uS max |
| .9 | Pulse Duty Factor | 6% | Max, AV1: 3.87% max; AV2: 4.5% max |
| .10 | Rise/Fall Time | 0.08-0.8 μsec | 10% to 90% Power Point; 90% to 10% Point |
| .11 | Pulse Droop | 0.25 dB | Maximum, 10% to 90% time of 32 μsec Pulse |
| .12 | Pulse Phase Variation | 6 degrees | Maximum, from 5 μsec after leading edge to 5 μsec prior falling edge with 32 μsec Pulse |
| .13 | Pulse Phase Stability | 0.03 degrees RMS | Maximum |

TABLE 3-continued

Specifications for the (9 + 1)CHPA that may be achieved

| Parameter | | Value | Comments |
|---|---|---|---|
| .14 | Pulse Amplitude Stability | 0.01 dB RMS | Maximum |
| .15 | Power Efficiency | 40% | Minimum |
| .16 | Primary Power | 4.8 kW at 50 VDC | Maximum in AV2 Operation |
| 2. | Physical Parameter | | |
| .1 | Outline Dimensions | 30" (L) × 14" (W) × 14" (H) | Nominal |
| .2 | Weight | 100 lb | Nominal |
| .3 | Connectors | TNC In, 7/16 Out, Ethernet | |
| 3. | Thermal Parameter | | |
| .1 | Water Inlet/Outlet Connectors | ¾" ID | |
| .2 | Flow Rates | 3.625 GPM | Nominal |
| .3 | Inlet Temp/ Pressure | 43.3° C./50 psi | Maximum |

The (9+1)CHPA may be used as an SPS-49 Radar Transmitter. The demonstrated pulse quality may include pulse droop, pulse variation, and pulse-to-pulse stability superior to legacy Klystron technology. This outstanding pulse quality inherent in solid state technology and circuit designs may be essential to achieve high Radar resolution.

In legacy radar transmitters utilizing Klystron and TWT technologies, the power supply may be designed to provide about a kV of DC with tube technology to the amplifiers achieving ultra-high RF power. Like Klystron and TWT, legacy power supply technologies may face significant and increasing challenges of diminishing manufacturing sources, unstable output, and inherent low MTBF. The high voltage operation may also impose safety issues for operators.

The introduction of solid state RF power device technology into HPA operating typically with only tens of volts may be safer. In recent years, switching solid state power technology has advanced rapidly up to 5 kW with a small profile. The new switching technology, operating with tens of volts output, may provide a more stable DC output and a low ripple voltage of only tens of mV, which may be essential for obtaining outstanding pulse-to-pulse stability for coherent pulse radar transmitter.

High voltage GaN technology has been introduced to switching power supply design. This may significantly extend the reliability of the power supply. In connection with an SPS-49 radar platform, the power supply unit (PSU) may be designed around a 2.75 kW power supply with 440VAC 3φ input and 50 VDC output. Its calculated MTBF may be greater than 100 kHrs in naval under deck environments.

However, in order to support hundreds of kW RF peak power, nearly 100 power supplies may be needed. These may collectively provide a reliability of less than 1 kHr MTBCF for the power supply system. Power supply redundancy may be used to address this concern.

Figure 24:
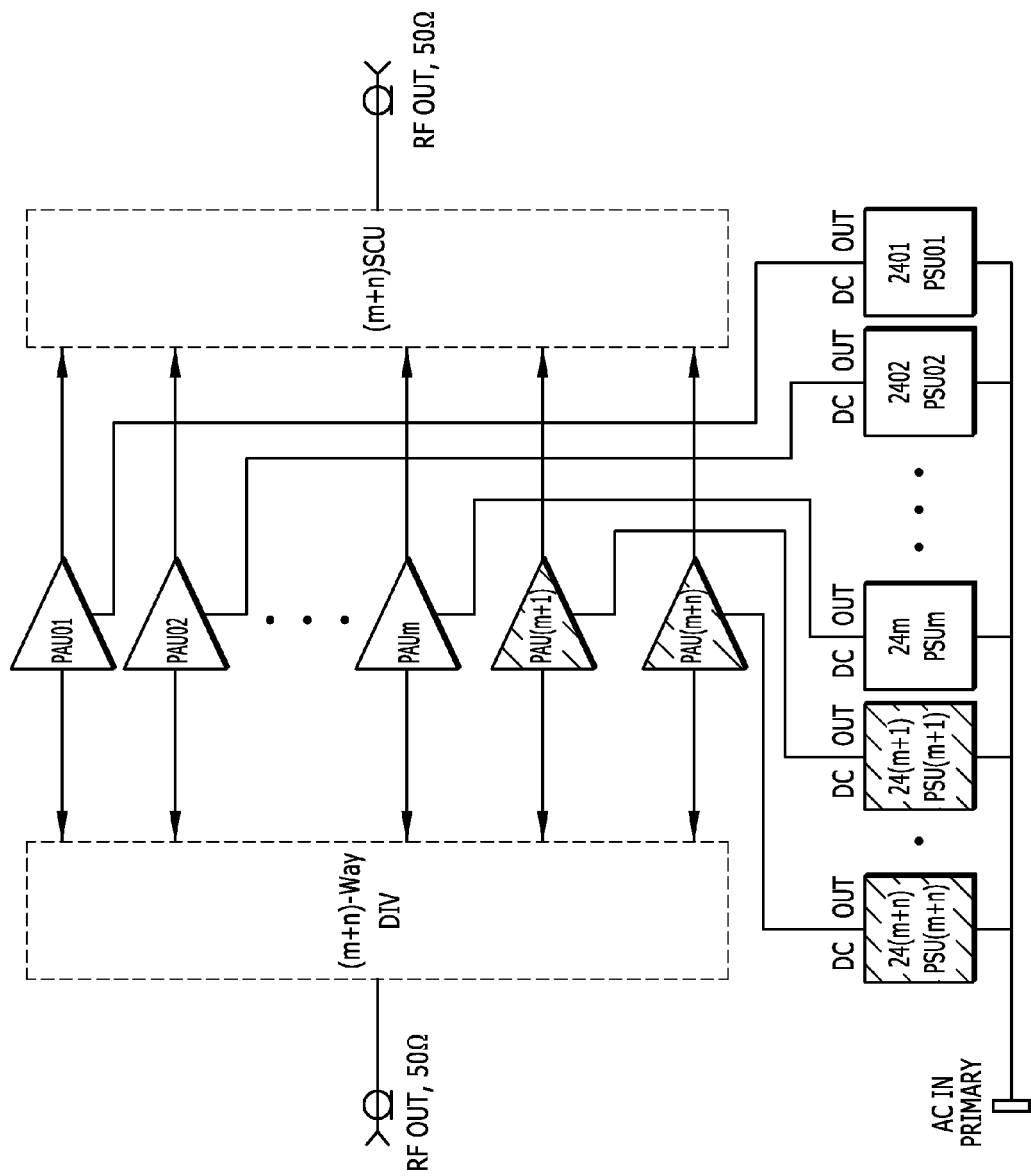
FIG. 24 illustrates a redundant (m+n) power supply bank ((m+n)PSB), along with an (m+n)CHPA.

FIG. 24 illustrates a redundant (m+n) power supply bank ((m+n)PSB), along with an (m+n)CHPA of any of the types discussed above. The architecture may have the same amount of power supply units (PSUs) as the PAUs, with a one PSU-to-one-PAU scheme. All PSUs may be "on" with their DC outputs DC OUT present. "M" PSUs may be "online" due to "m" "online" PAUs drawing current. "n" PSUs may be in "standby" due to "n" "standby" PAUs not drawing current. When one of the "online" PSUs fails, its controller may send fault signals to the ICU (not shown in FIG. 24) and the ICU may place the corresponding PAU offline. Thus, the failed PSU may not supply the current to the offline PAU, so that the failed PSU may be offline instantly. Then, one of the "standby" PSUs may automatically fail over due to its corresponding PAU automatically being placed "online" by the ICU.

Therefore, automatic fail-over and uninterrupted operation of an (m+n)PSB may be achieved via its (m+n)CHPA. Then, the MTBF of the PSUs may be excluded from the MTBCF calculation of the SSTx system consisting of one pair of an (m+n)CHPA and an (m+n)PSB. Thus, the introduction of an (m+n)PSB architecture may not result in the SSTx MTBCF and availability (Ao) degradations as shown in Equations 17 and 18.

$$MTBCF_{SSTX} = \frac{MTBF_{DIV} MTBF_{SCU}}{MTBF_{DIV} + MTBF_{SCU}} \quad (17)$$

$$A_{OSSTX} = \left\{\frac{MTBF_{DIV} - MTR_{DIV}}{MTBF_{DIV}}\right\}\left\{\frac{MTBF_{SCU} - MTR_{SCU}}{MTBF_{SCU}}\right\} \quad (18)$$

In addition, the graceful degradation feature with more than "n" PSU failures and "hot-swap" feature may also be achieved as described above in connection with an (m+n) CHPA.

In FIG. 24, PSUs 2401 to 24(m+n) are added to the basic (m+n)CHPA block diagram. The hatched PSU(m+1) to PSU (m+n) may be "on" supplying DC voltages, but may be in "standby" due to the "standby" PAUs not drawing currents. When either a PSU or PAU failure occurs, the instant fail-over can be achieved due to adequate DC energy being charged within the PAU.

Figure 25:
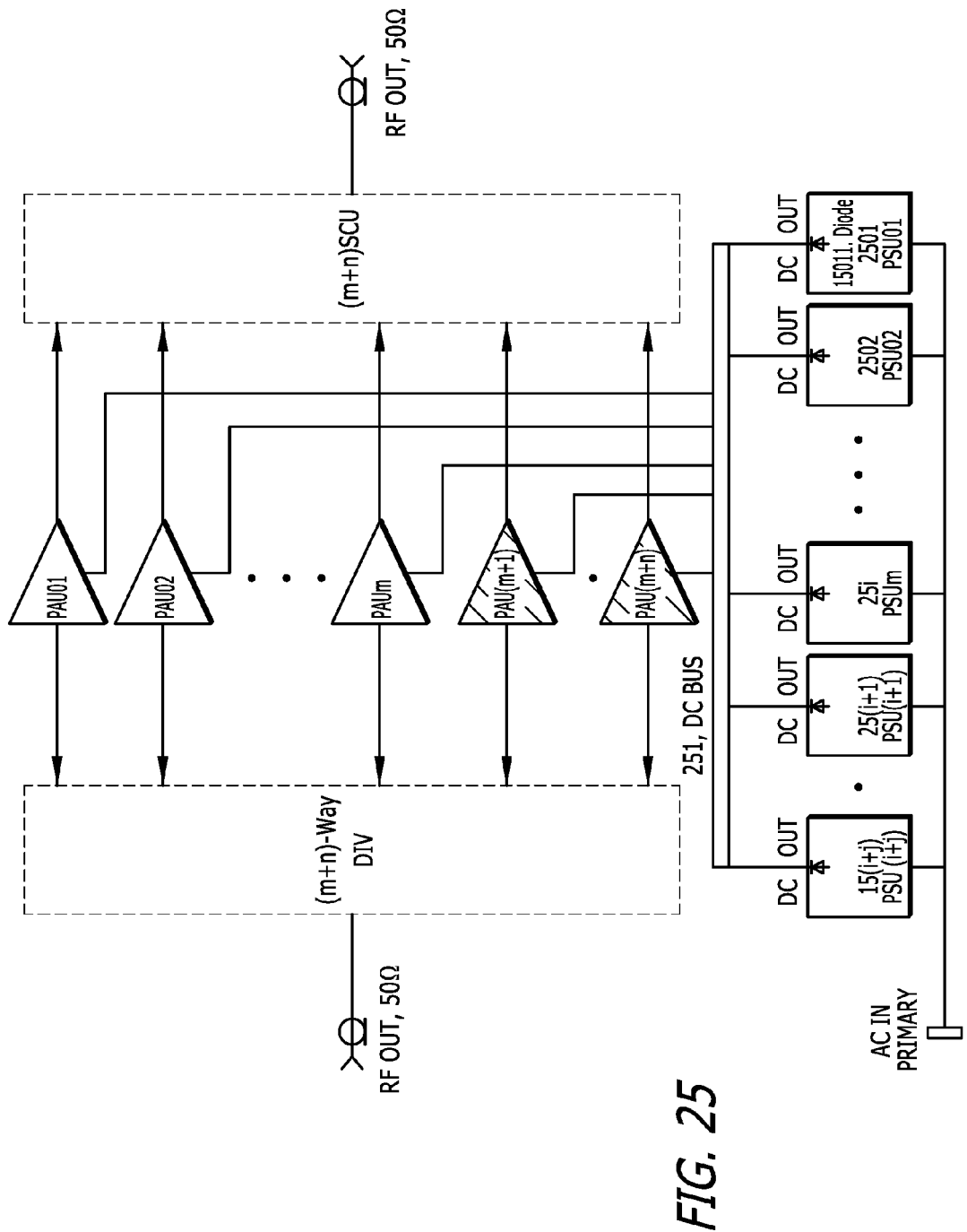
FIG. 25 illustrates an alternate redundancy design for a power supply bank (PSB) that has (i+j) PSUs that form paralleling (i+j) redundancy

FIG. 25 illustrates an alternate redundancy design for a power supply bank (PSB) that has (i+j) PSUs that form paralleling (i+j) redundancy. FIG. 25 shows the (i+j)PSB addition to the basic (m+n)CHPA. All the outputs from power supplies 2501 to 25(i+j) may be summed at a DC bus 251. Built-in series diodes, such as a diode 1501 in PSU 2501, may be used for the paralleling scheme. In a (i+j)PSB scheme, all PSUs may be "on" and supply equal currents to a common DC output to the CHPA. When one of the PSUs fails, the system may operate normally with the (i+j−1) PSUs supplying the needed current for CHPA, and may be shut down when the PSU failures exceed j. Therefore, the architecture may not provide graceful degradation due to PSU failures; but it may support graceful degradation operation due to PAU failures.

This configuration may allow the transmitter system to have a small number of PSUs, thus providing a smaller profile and potentially lower cost. However, the configuration may introduce a common DC bus failure which may be in the critical path, and thus compromise MTBCF and Ao performances. Additionally, a single DC "short" failure in any one of PAUs may bring down system operation. However, when power, power density, and reliability are equally important, the disclosed configuration may provide an optimal trade-off.

Therefore, to support the example 40 kW (9+1)CHPA, a (i+j)PSB, with i=2 and j=1, may be used with 2.75 kW power supplies.

Figure 26A:
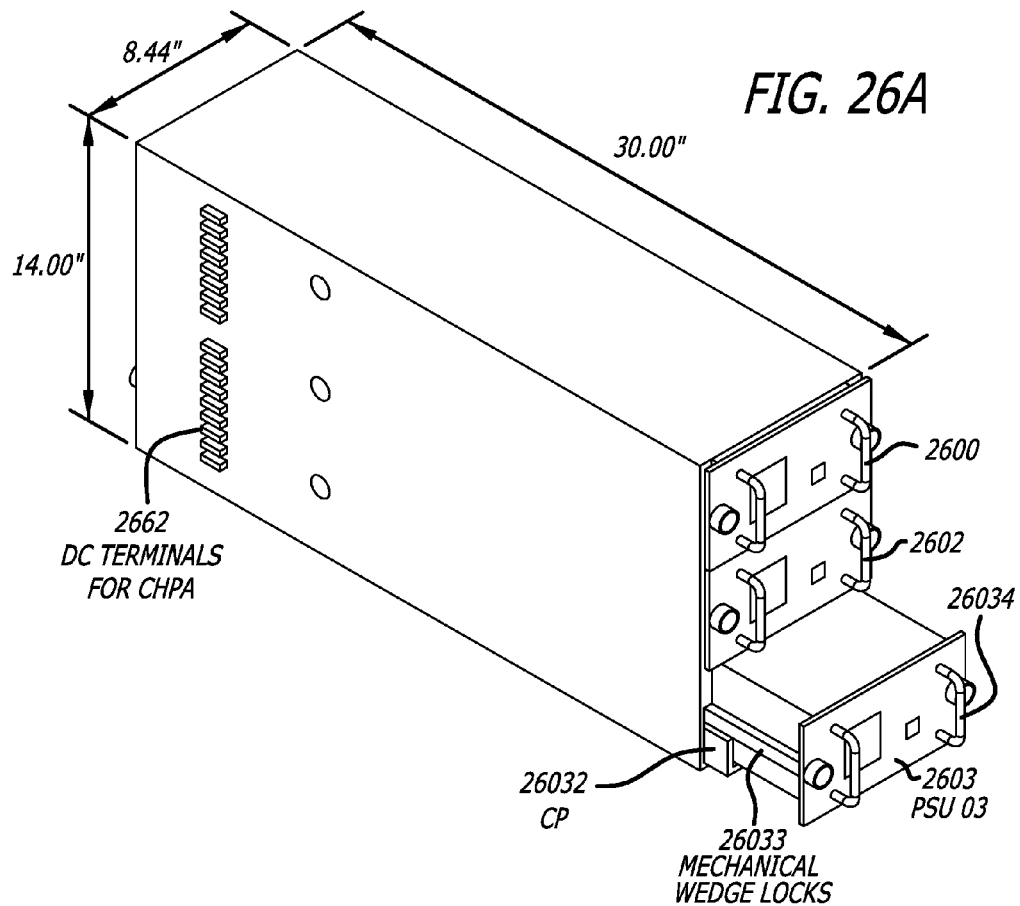
FIGS. 26A and 26B illustrate two views of a (2+1)PSB configuration with the same height and depth dimensions as in a (9+1)CHPA, so that a pair of (9+1)CHPA/(2+1)PSB can be readily integrated as one entity.
Figure 26B:
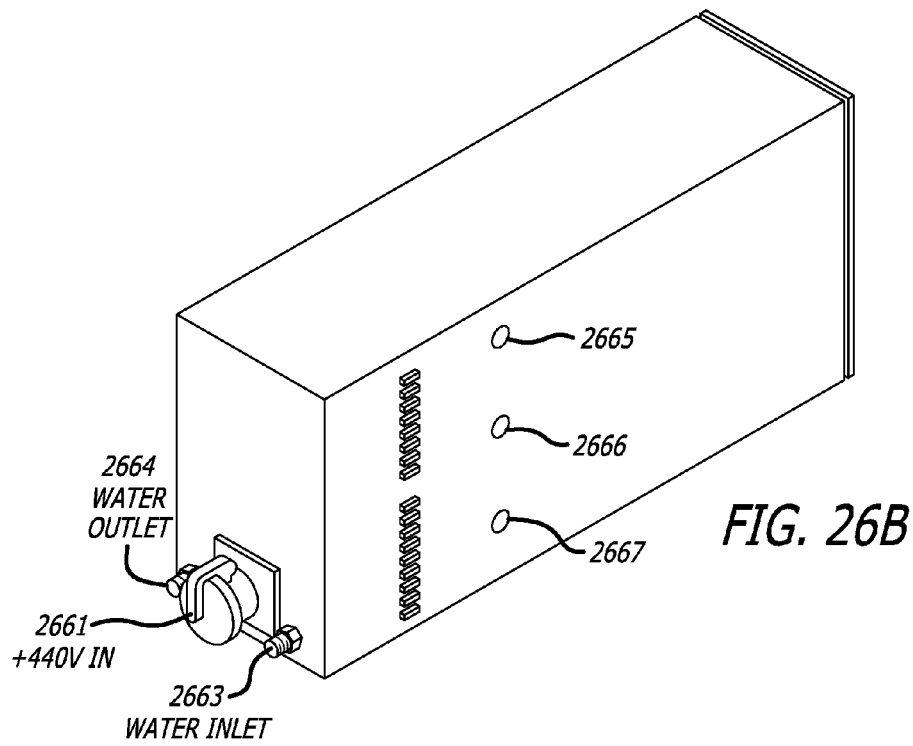

FIGS. 26A and 26B illustrate two views of a (2+1)PSB configuration with the same height and depth dimensions as in a (9+1)CHPA, so that a (9+1)CHPA and a (2+1)PSB can be readily integrated as one entity. The PSB may include three 2.75 kW PSUs 2600, 2602, and 2603. Two of the three PSUs may adequately support a 4.8 kW maximum DC consumption of the (9+1)CHPA as specified in Table 3.

Mechanical wedge locks, like mechanical wedge locks 26033 and 26034, may be designed to cause their associated PSU to be placed against or to be removed from a power supply water cooling plate 26032. This may enable a failed PSU to be removed using "hot-swapping." The PSB may have a +440VAC three phase input 2661, DC terminals 2662 for CHPA DC interfaces, a water inlet 2663, a water outlet 2664, and Ethernet interfaces 2665-2667 from the PSUs to the ICU in the (9+1)CHPA.

Figure 27A:
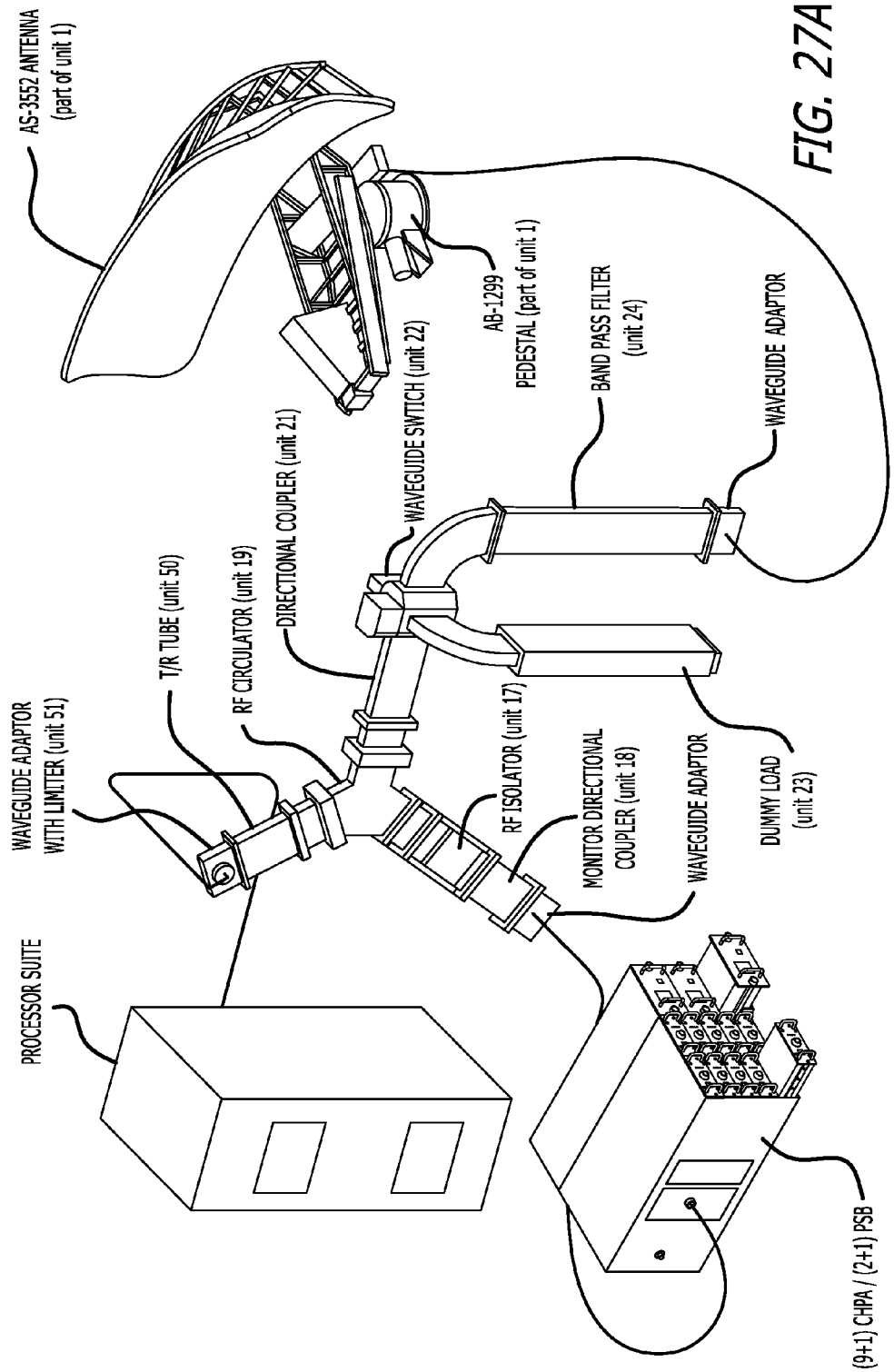
FIGS. 27A-27C illustrate various components in an example of a (9+1)CHPA and (2+1)PSB set up for an SPS-49 platform.
Figure 27C:
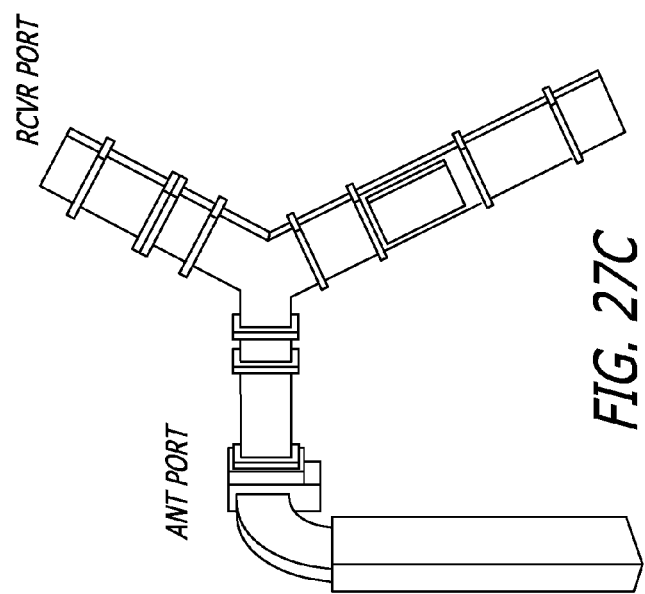
Figure 27B:
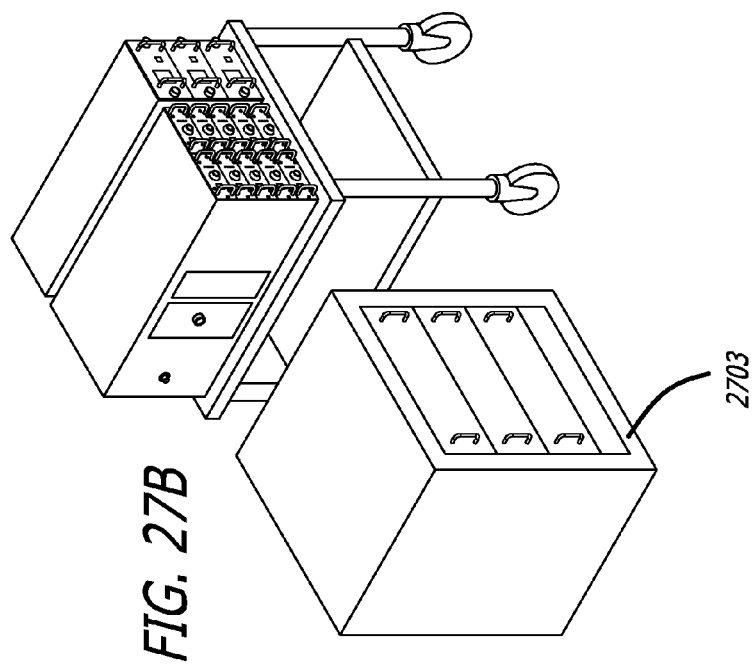

FIGS. 27A-27C illustrate various components in an example of a (9+1)CHPA and (2+1)PSB set up for an SPS-49 platform. The setup may include a GFE, including an antenna and waveguide assembly, a transmitter including a (9+1)CHPA and a (2+1)PSB, and a radar signal processor suite. A peripheral rack 2703 may be included.

An ultra-high power, such as hundreds of kWs, SSTx may be achieved by combining several of the disclosed CHPAs and PSBs utilizing reliable and proven passive combining technology. Such an SSTx scheme may provide unprecedented solid state power and reliability due to the high reliability of its major sub-assemblies, such as the CHPAs and PSBs.

Figure 28:
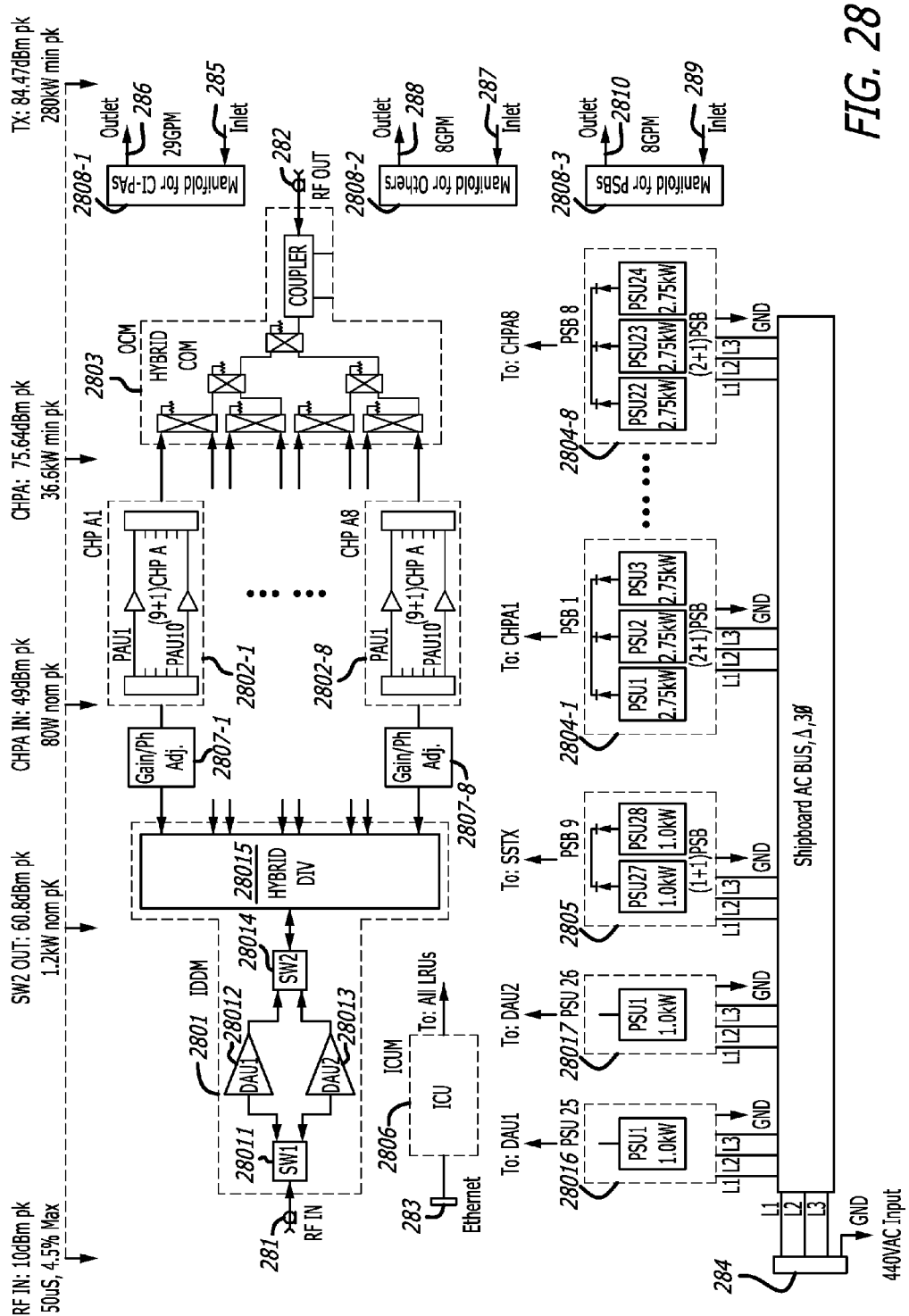
FIG. 28 illustrates an example of a more than 280 kW SSTx that combines eight modular redundant (9+1)CHPAs utilizing hybrid combiners to replace a legacy Klystron transmitter for an SPS-49.

FIG. 28 illustrates an example of a more than a 280 kW SSTx that combines eight modular redundant (9+1)CHPAs utilizing hybrid combiners to replace a legacy Klystron transmitter for an SPS-49. For the RF path, a small signal may be input at an input port 281 and boosted and divided by an input driver and divider module (IDDM) 2801 into 8 outputs, one to each of eight (9+1)CHPAs 2802-1 to 2802-8 through gain/phase adjustors 2807-1 to 2807-8 providing 80 W nominal inputs to the CHPAs 2802-1-8. Each CHPA 2802-1-8 may reliably deliver 36.6 kW minimal power. An output combiner module (OCM) 2803 may sum the input powers to greater than 280 kW and deliver this to an RF output 282. The OCM may include reliable passive hybrid couplers with more than 1 million hours MTBF and thus may not degrade the MTBCF of the SSTx.

Redundancy in the IDDM may ensure that all sub-assemblies in the critical path having greater than 100 kW MTBCF. Thus, the RF path may offer outstanding MTBCF.

Regarding the power supply scheme, there may be 8 redundancy (2+1)PSBs 2804-1 to 2804-8 to support the CHPAs. In addition, PSUs 28016 and 28017 may supply power to driver amplifier units (DAUs) 28012 and 28013 utilizing the previously disclosed "one power-to-one PAU" scheme.

A PSB 2805 may be a (1+1) and provide parallel redundancy reliably to all system control needs. Therefore, the power supply path from a primary input 284 to the DC outputs may be reliable.

The disclosed SSTx may also provide cooling water, such as the existing 29 GPM to a manifold 2808-1 to remove heat from the CHPAs, the existing 8 GPM to a manifold 2808-3 to cool the PSUs, and another existing 8 GPM to a manifold 2808-2 for other system application heat removal. An ICU 2806 may monitor and control all sub-assemblies through an Ethernet port 283. This approach may outperform a legacy Klystron radar transmitter.

Example specifications for the disclosed SSTx are summarized in the following Table 4:

TABLE 4

Specifications for 280 kW SSTx for SPS-49 Radar Utilizing Multiple CHPAs

| Parameter | | Value | Comments |
|---|---|---|---|
| 1. | Electrical Performance | | |
| 1.1 | Operating Frequency | 850-942 MHZ | Minimum, Upper and Lower −1dB Point |
| 1.2 | RF Output Power, peak | 84.47 dBm/85.47 dBm | Min/Max,; 280 kW/352 kW; 1 dB Variation |
| 1.3 | RF Input Power, peak | 11.0 dBm (80 W) | Nominal, +/−1.0 dB |
| 1.4 | Spurious Output | 60 dBc | Minimum, from 962-1212 MHz |
| 1.5 | Harmonic Output | 30 dBc 2nd, 40 dBc 3rd-5th | Minimum |
| 1.6 | Input/output VSWR | 1.5:1 | Maximum |
| 1.7 | Output VSWR Survival | 2:1 | Minimum, all phase |
| 1.8 | Pulse Width | 2-64 μsec | AV1: 32 uS max; AV2: 50 uS max |
| 1.9 | Pulse Duty Factor | 6% | Max, AV1: 3.87% max; AV2: 4.5% max |
| 1.10 | Rise/Fall Time | 0.08-0.8 μsec | 10% to 90% Power Point; 90% to 10% Point |
| 1.11 | Pulse Droop | 0.25 dB | Maximum, 10% to 90% time of 32 μsec Pulse |
| 1.12 | Pulse Phase Variation | 6 degrees | Maximum, from 5 μsec after leading edge to 5 μsec prior falling edge with 32 μsec Pulse |
| 1.13 | Pulse Phase Stability | 0.03 degrees RMS | Maximum |
| 1.14 | Pulse Amplitude Stability | 0.01 dB RMS | Maximum |
| 1.15 | Power Efficiency | 37.2% | Minimum |
| 1.16 | Primary Power | 42.6 kW at 440 VAC 3φ | AV2: 42.6 kW max; (4.5% DF) |
| 2. | Physical Parameter | | |
| 2.1 | Outline Dimensions | Rack: 36" (L) × 32" (W) × 68" (H) | Two 901D Rack; Also Retro-fit Feasible |
| 2.2 | Weight | 4,000 lb | ROM, Including Racks |
| 2.3 | Connectors | TNC In, WR975, Ethernet | Option: Original 3⅛" RF Output Interface |
| 3. | Thermal Parameter | | |
| 3.1 | Water Inlet/Outlet Connectors | TBD | Compatible to Existing Cooling Interfaces |
| 3.2 | Flow Rates | 45 GPM | Nom, Existing 29 GPM, 8 GPM, 8 GPM Sources |
| 3.3 | Inlet Temp/Pressure | 43.3° C./50 psi | Maximum |

Driver amplifier units (DAU) 28012 and 28013 may provide automatic redundancy for the SSTx and thus may reduce system down time in the RF chain to minimal. The driver redundancy may include two RF switches 28011 and 28014 to form a (1+1) redundancy scheme. The RF switches may ensure uninterrupted operation with driver amplifier failures.

The DAU 28012 may nominally be "online" and the DAU 28013 may nominally be in "standby." When DAU 28012 fails, a built-in controller of the DAUs may send a fault signal to the ICU 2806, then the identical automatic fail-over scheme as in (m+n)CHPA can be achieved in IDDM. Therefore, the DAUs may also not be in the critical path and may not degrade the MTBCF of IDDM.

Switches 28011 and 28014 and a passive hybrid divider 28015 may be high reliable components. Thus, the MTBCF of the IDDM may be high. In addition, DAU "hot-swap" may be implemented in the same way as the corresponding PAU scheme.

Figure 29A:
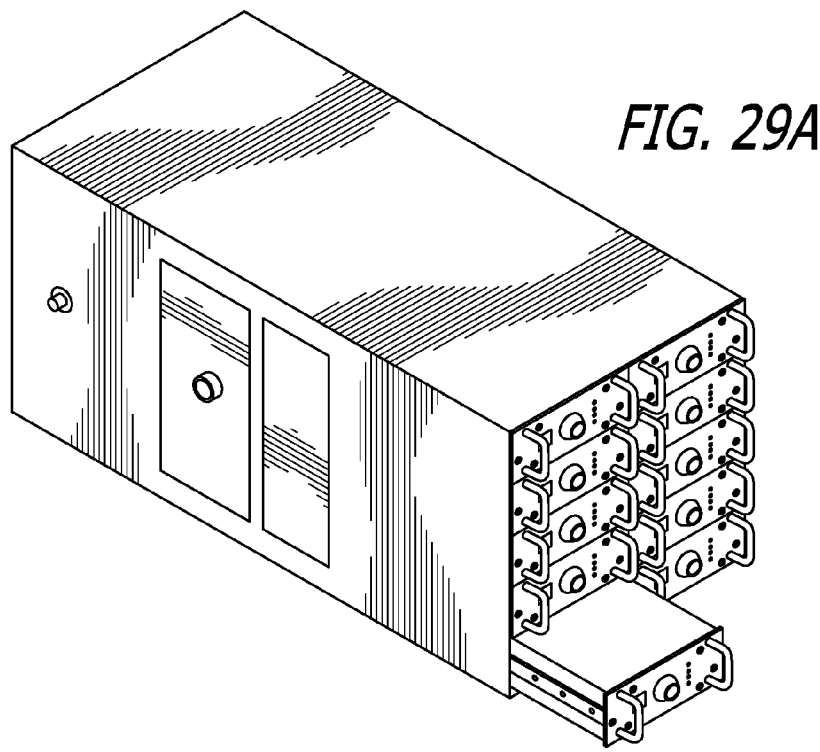
FIGS. 29A-29E illustrate examples of various components that may be part of an ultra-high power SSTx.
Figure 29B:
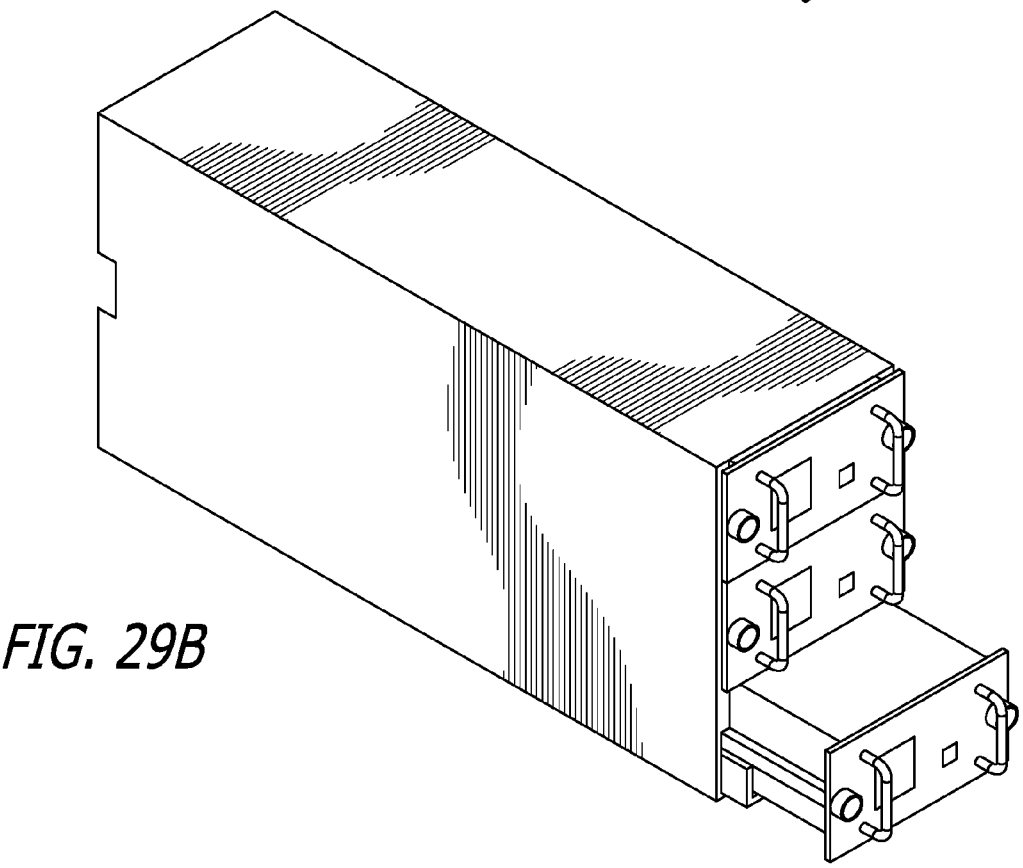
Figure 29C:
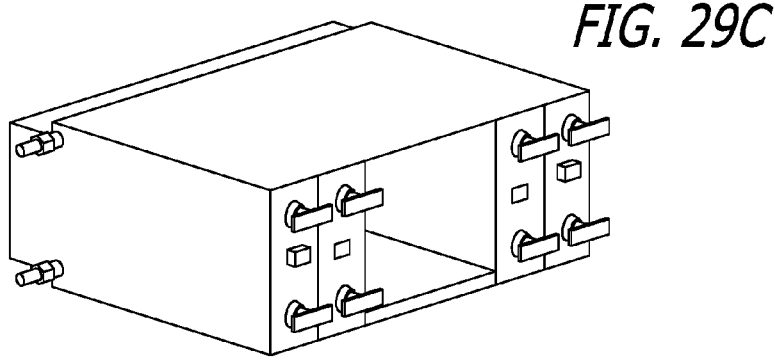
Figure 29D:
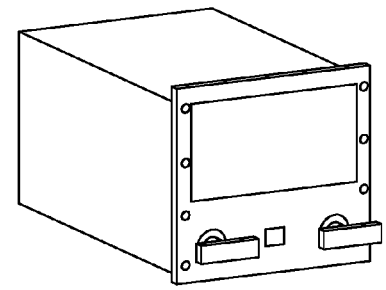
Figure 29E:
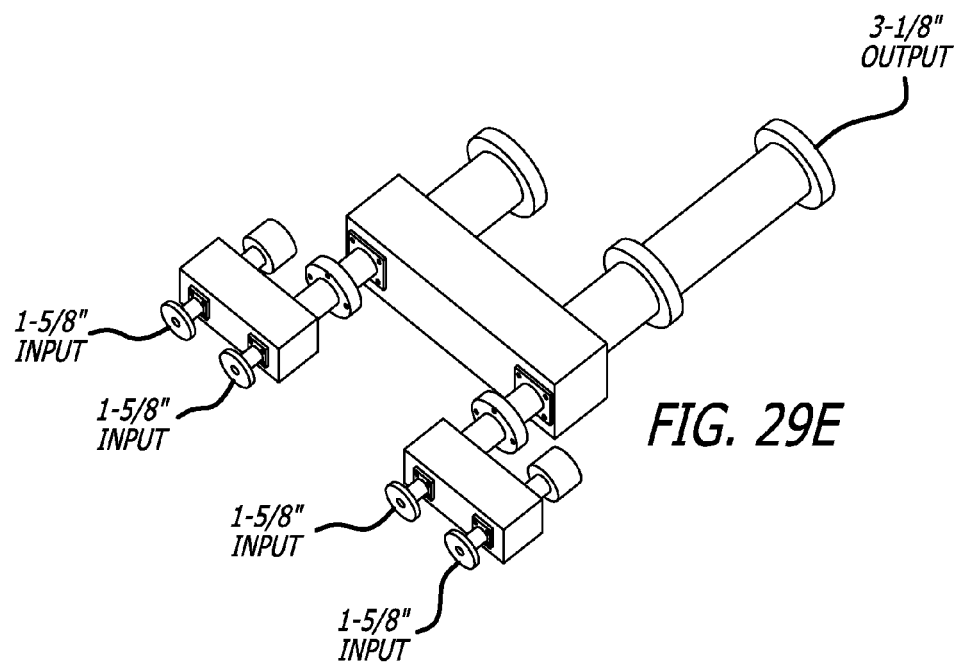

FIGS. 29A-29E illustrate examples of various components that may be part of an ultra-high power SSTx. FIG. 29A illustrates a CHPA module; FIG. 29B illustrates a PSB module; FIG. 29C illustrates an IDD module with PSUs; FIG. 29D illustrates an ICU module located in an IDDM; and FIG. 29E illustrates a 4-way OCM with an output coupler (the proposed 280 kW SSTx may include two 4-way OCMs).

The disclosed modular design offers a hatchable solution for installation and maintenance requirements of replacing the existing transmitter. The design may include a modular CHPA and power supply bank (PSB), IDDM, OCM, and an interface control module (ICM). Each module, with manageable dimensions and weight, can be integrated and tested independently, then transported through the "hatch" of a ship and integrated into an SSTx rack. The modular approach may make transmitter upgrades practical, may ease maintenance complications, and may increase system availability by reducing MTR.

In the IDDM design, a card cage assembly may be designed to house the DAUs and their corresponding PSUs and to support DAU and PSU "hot-swapping." The interface control module (ICM) may fit inside the IDDM car cage. The OCM design may be a 4-way combiner with the output directional coupler, and two 4-way OCM may be included for the proposed 280 kW SSTx. The 4 input 1⅝" EIA ports in FIG. 29E may interface with the CHPA directly via 7/16 DIN to 1⅝" EIA Adaptors. A 3⅛" EIA RF connector at the output of the OCM may match the original system interface to an LPF (Low Pass Filter, GFE Unit #17)

The disclosed CHPA and PSB designs may provide significantly higher standards for operational availability (Ao), reliability, and maintainability, while reducing total cost of ownership by adapting to a shipboard environment, scalable (m+n) transmitter architecture, for coherent transmitters. The (m+n) main building blocks may be part of the combining high power amplifier design and a redundant power supply bank may support true hot-swapping, automatic fail-over, and graceful power degradation.

Figure 30:
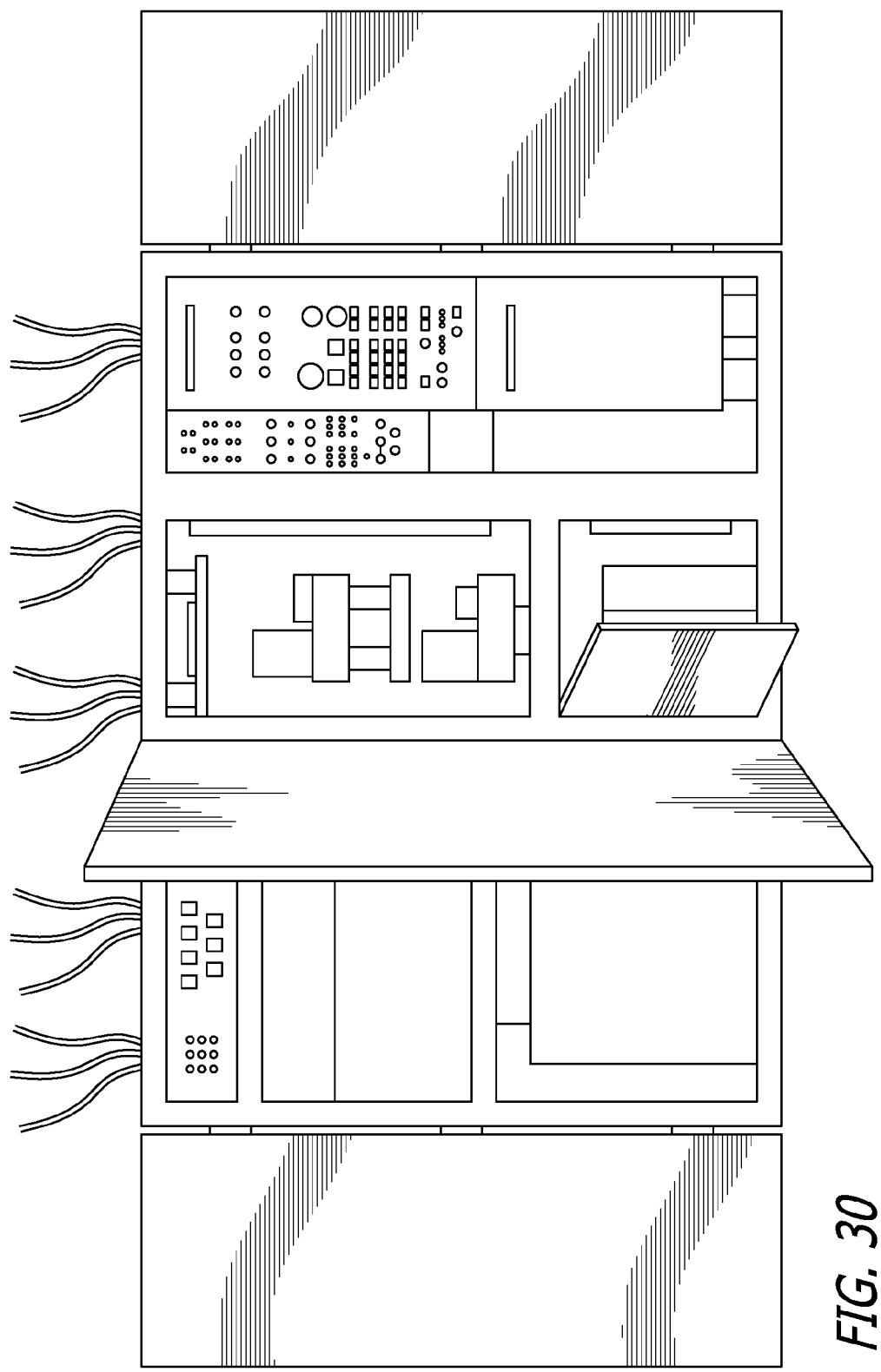
FIG. 30 illustrates an example of a legacy SPS-49 transmitter.
Figure 31:
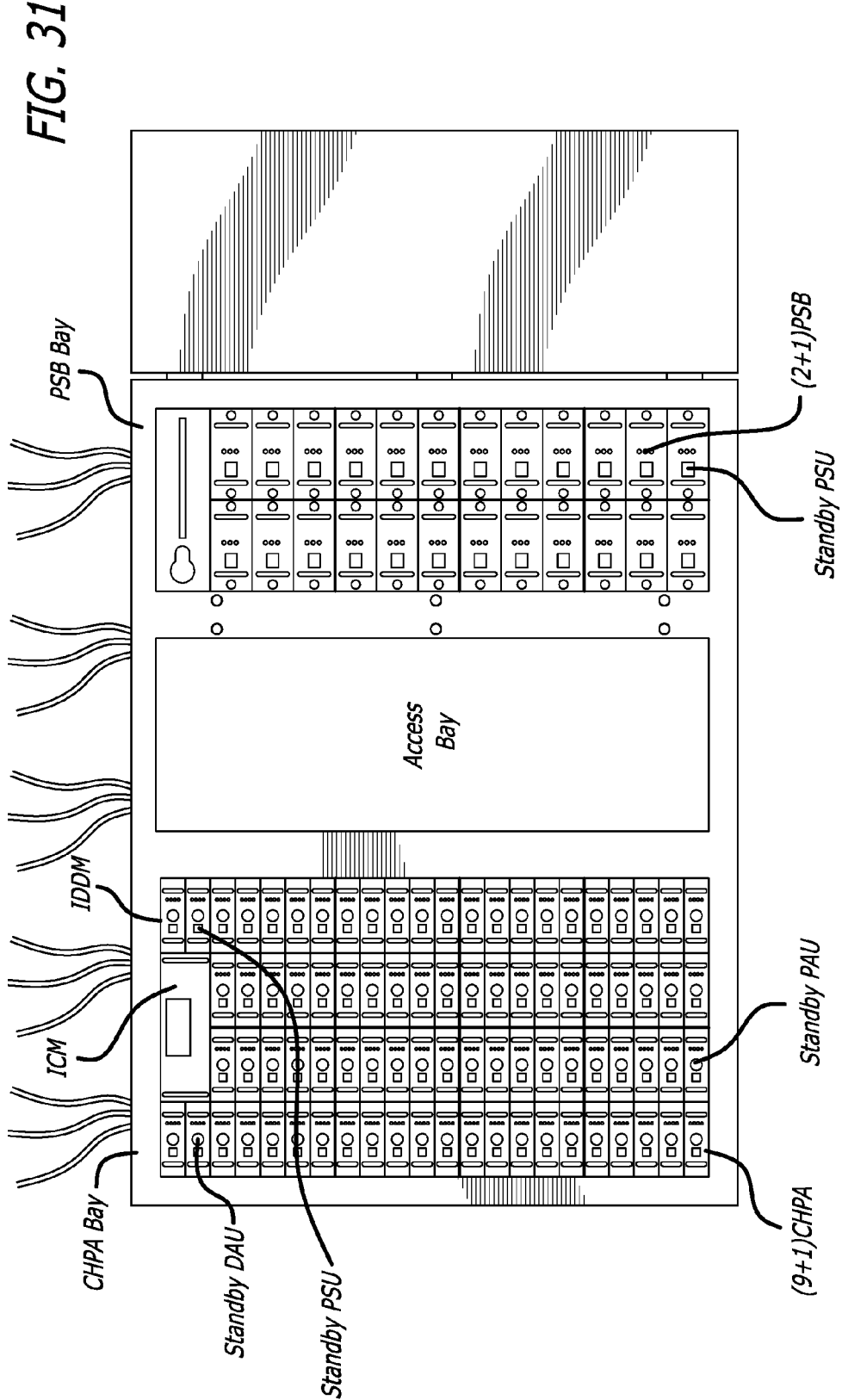
FIG. 31 illustrates an example of a solid state upgrade following the teaching herein that uses only two existing bays, leaving the middle bay for maintenance access.

FIG. 30 illustrates an example of a legacy SPS-49 transmitter. FIG. 31 illustrates an example of a solid state upgrade to this legacy transmitter following the teaching herein that used only two existing bays, leaving the middle bay for maintenance access. The CHPA bay may enclose 8×(9+1)CHPAs, the IDDM, and the ICM. The PSB bay may be occupied by 8×(2+1)PSBs. The hatched LRUs may be in "standby".

Figure 32:
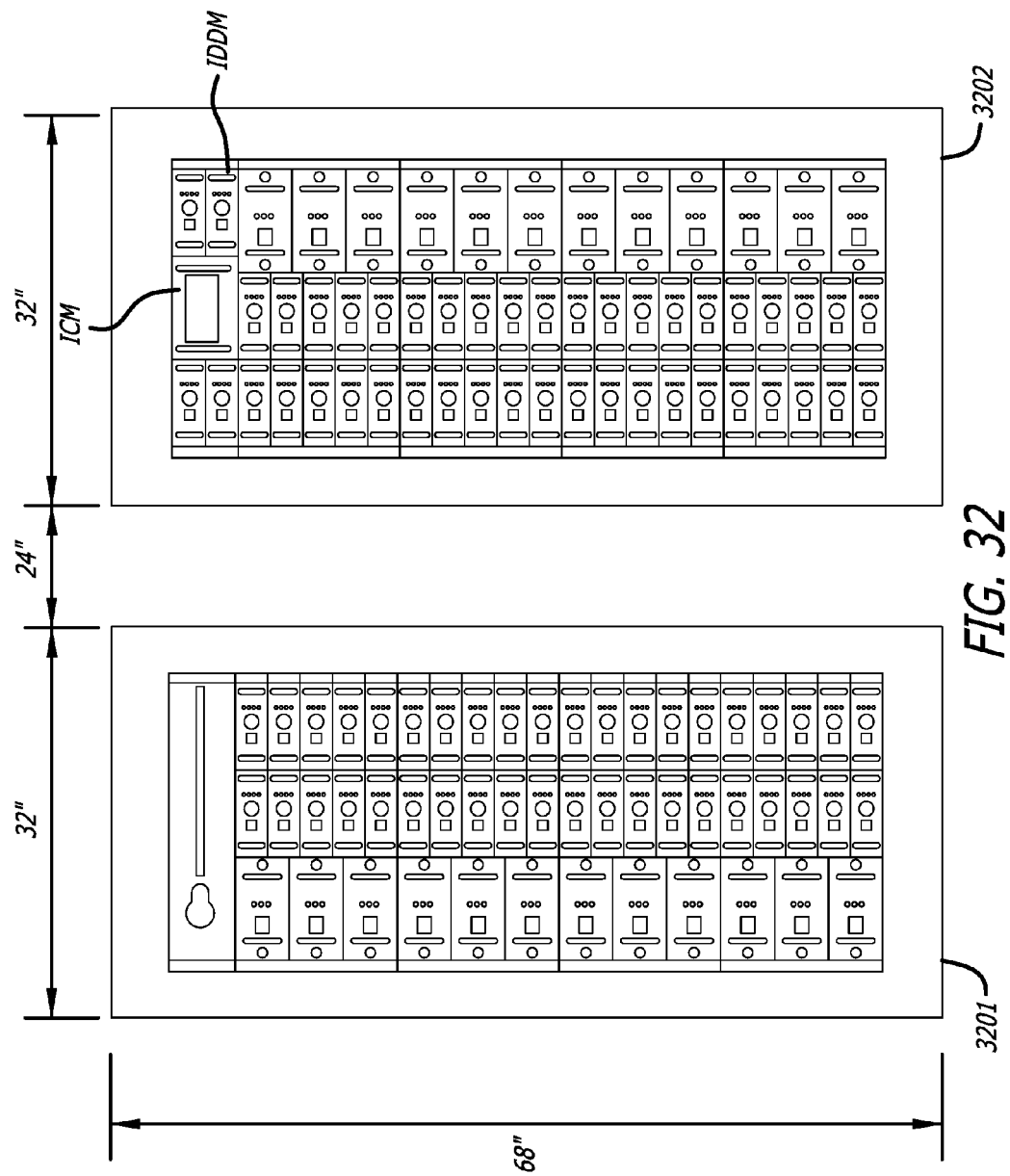
FIG. 32 illustrates an alternative forward fit upgrade proposal for the SPS-49 radar transmitter using two 901D racks.

A feasible solid state upgrade may include a thorough analysis of the SPS-49 radar specifications and site surveys. The disclosed SSTx configurations may outperform the existing transmitter, and may include sound mechanical and thermal management properties. The dimensions of the building blocks may be developed to meet retrofit requirements, FIG. 32 illustrates an alternative forward fit upgrade proposal for the SPS-49 radar transmitter using two 901D racks 3201 and 3202. Each may house 4 CHPA/PSB assemblies. In addition, an IDDM and ICM may be enclosed in the rack 3202. Separation of the two racks may support installation and maintenance access which may eventually increase system availability by decreasing the MTRs of LRUs. The disclosed forward-fit SPS-49 Tx upgrade may simplify the design, system integration, and rigid environmental qualification procedures.

A cable-less version of the CHPA may provide even greater advantages to the SPS-49 upgrade activity from mechanical packages and cost perspectives. A cable-less CHPA may integrate the SCU, the power divider, and the RF input switches into a divider/switching combiner unit (DSCU). Although the advancement may introduce another level of complexity, it may significantly reduce the implementation costs of an (m+n) SSTx, without compromising availability, reliability, or maintainability.

FIG. 33 illustrates an example of a 10-way input power divider (DIV) and switching combiner unit (SCU) combined into a single unit (DIV/SCU combo). As illustrated in FIG. 33, ten pairs of input/output, phase-matched cable assemblies may connect 10 PAUs with a 10-way divider and a (9+1)SCU. The high power, low-loss, phase-matched cables may have a very large inner bending radius. This may introduce significant physical volumetric growth into the CHPA modular assembly. As a result, 6.8 W/in$^3$ power density may be achieved in a 40 kW (9+1)CHPA design, as illustrated in FIGS. 21A and 21B.

The matched cables may mechanically increase the challenge of integrating a 280 kW SSTx into an existing transmitter cabinet. In addition, cable assemblies may also affect the stability and the consistency of the daily transmitter operation, especially in a shipboard environment. The removal of ten, high-power, phase-matched cables may dramatically increase overall transmitter reliability due to the elimination of high tension bends, joints, and a reduced number of connections.

Cost reduction considerations in a 280 kW SSTx utilizing (m+n)SSTx architecture may dictate an advanced DSCU development. A cost analysis based on cable assemblies used in a CHPA/PSB demonstration program suggests that removing phase-matched cables may save more than $300,000 in materials and also may dramatically reduce assembly time. The total cost reduction for a 280 kW SSTx may therefore exceed $1 million due to the introduction of a DSCU. Furthermore, the disclosed DSCU approach may dramatically improve system maintainability.

As an example, a (7+1)DSCU design is used to explain the disclosed design approach, which may include an 8-way input power divider, 8 RF input switches, and a (7+1)SCU. Based on possible dimensions of RF interfaces in the PAU, various design approaches may be achieved through geometric or trigonometric analysis.

Figure 34A:
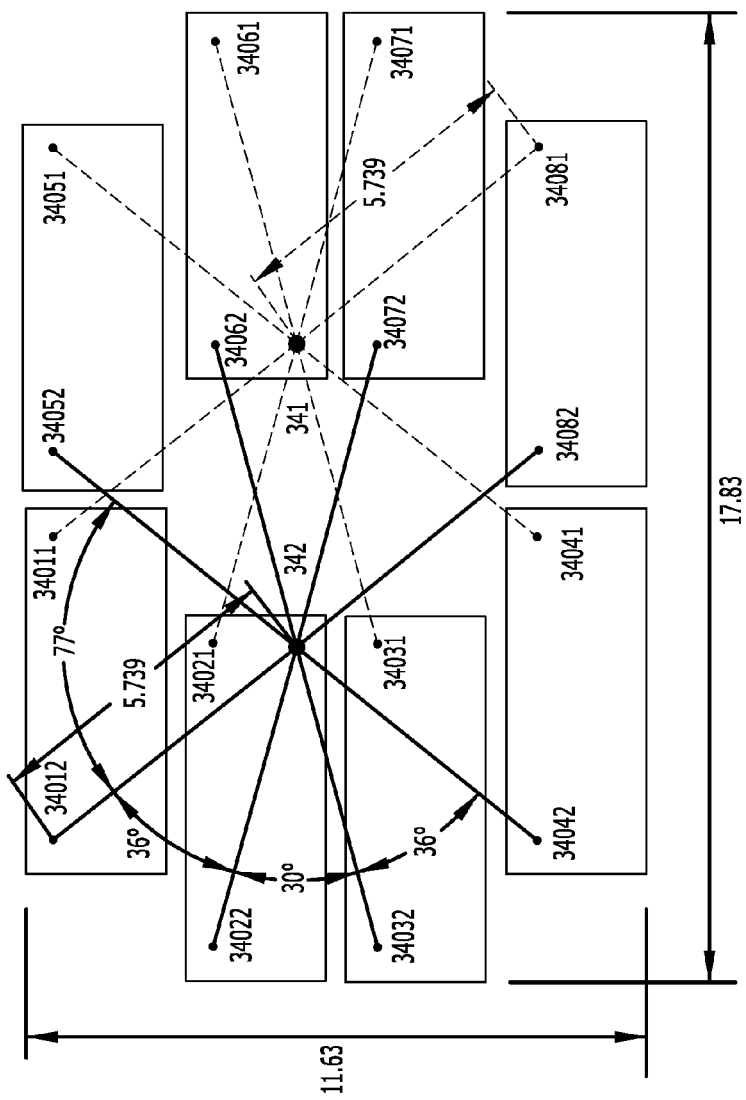
FIG. 34A illustrates an example of an input/output constellation arrangement of connectors in a (7+1)DSCU design that may connect to multiple PAUs.
Figure 34B:
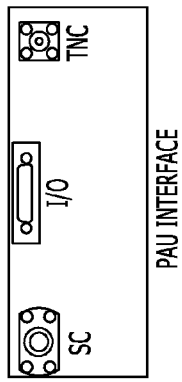
FIG. 34B illustrates an example of a back side of a PAU configured to slidably engage connectors on the DSCU illustrated in FIG. 34A.

FIG. 34A illustrates an example of an input/output constellation arrangement of connectors in a DSCU design that may connect to multiple PAUs. FIG. 34B illustrates an example of a back side of a PAU configured to slidably engage connectors on the DSCU illustrated in FIG. 34A. The branches may be equal in electrical length, and there may be minimal penetration interference between the DIV and the SCU assemblies. All inputs and outputs of the PAUs may fall on two separate circles, one for the inputs and one for the outputs. For example, all TNC RF inputs may be landed on one circle, while all SC RF outputs may be landed on the second circle, each with a 5.739" radius. This may cause the electrical lengths from the center of the SCU to each PAU output port to be the same, and the electrical lengths from the center of the DIV to each PAU input port to be the same.

In the path from the SCU to each PAU output, there may be a λ/4 line, followed by a high power RF switch and then a transmission line to the SCU input. In the path from the center of the DIV to each PAU input, there may be a dividing branch, followed by the RF switch and then a transmission line to each DIV output.

FIG. 34A also illustrates an overlay between the DIV and the SCU, with four RF interfaces on one assembly penetrating into the other one. The SCU may be in front of the DIV or the other way around. When in front, long TNC barrels on TNC connectors 34011, 34021, 34031, and 34041 may penetrate through the SCU, with the TNC connectors 34021 and 34031 at the center line of the SCU and an SCU output 342 at the mid of the TNC connectors 34021 and 34031 of the DIV. This may keep the penetration interferences to the RF paths at a minimum. The other TNC connectors 34051, 34061, 34071, and 34081 on the DIV may not penetrate through the SCU due to the offset between DIV and SCU.

Figure 35A:
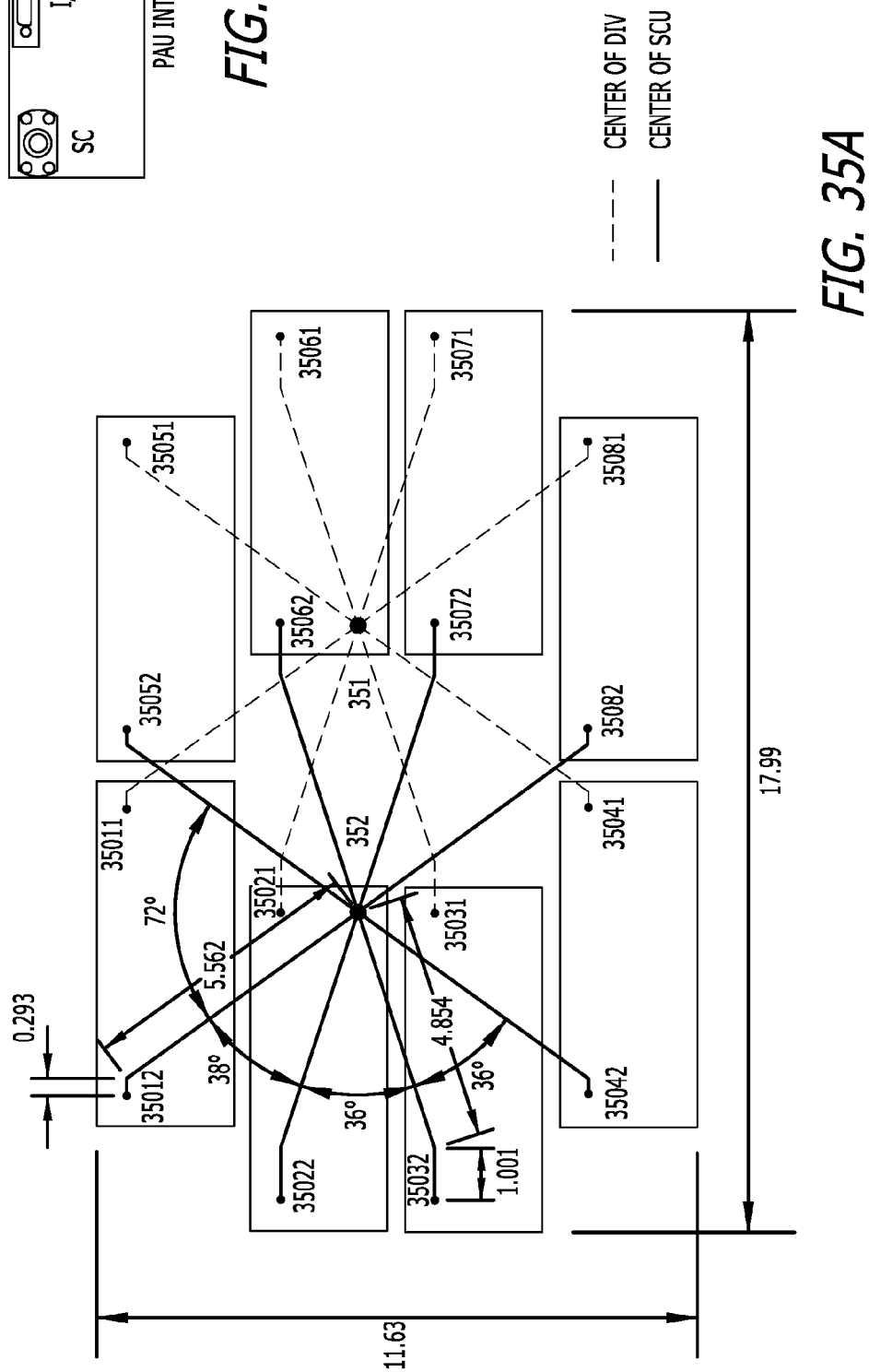
FIG. 35A illustrates another example of an input/output constellation arrangement of connectors in a (7+1)DSCU design that may connect to multiple PAUs with uniform angle separation between adjacent branches.
Figure 35B:
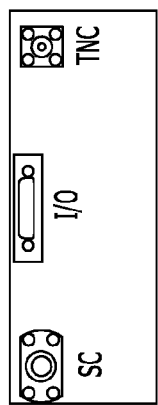
FIG. 35B illustrates an example of a PAU configured to slidably engage connectors on the DSCU illustrated in FIG. 35A.

FIG. 35A illustrates another example of an input/output constellation arrangement of connectors in a DSCU design that may connect to multiple PAUs with uniform angle separation between adjacent branches. FIG. 35B illustrates an example of a PAU configured to slidably engage connectors on the DSCU illustrated in FIG. 35A. In this arrangement, adjacent RF paths may be uniformly separated with 36° to achieve uniform RF performance. The total electrical lengths may equal 5.855" (the sum of 5.562" and 0.293", or the sum of 4.854" and 1.00"), and there may be minimal overlay interferences. In addition, a minor input connector location adjustment of the PAU may be necessary to achieve the desired arrangement. In the case of placing the SCU in front of the DIV, TNC connectors 35011, 35021, 35031, and 35041 may similarly penetrate through the SCU, while 35051, 35061, 35071, and 35081 may not penetrate the SCU.

Figure 36A:
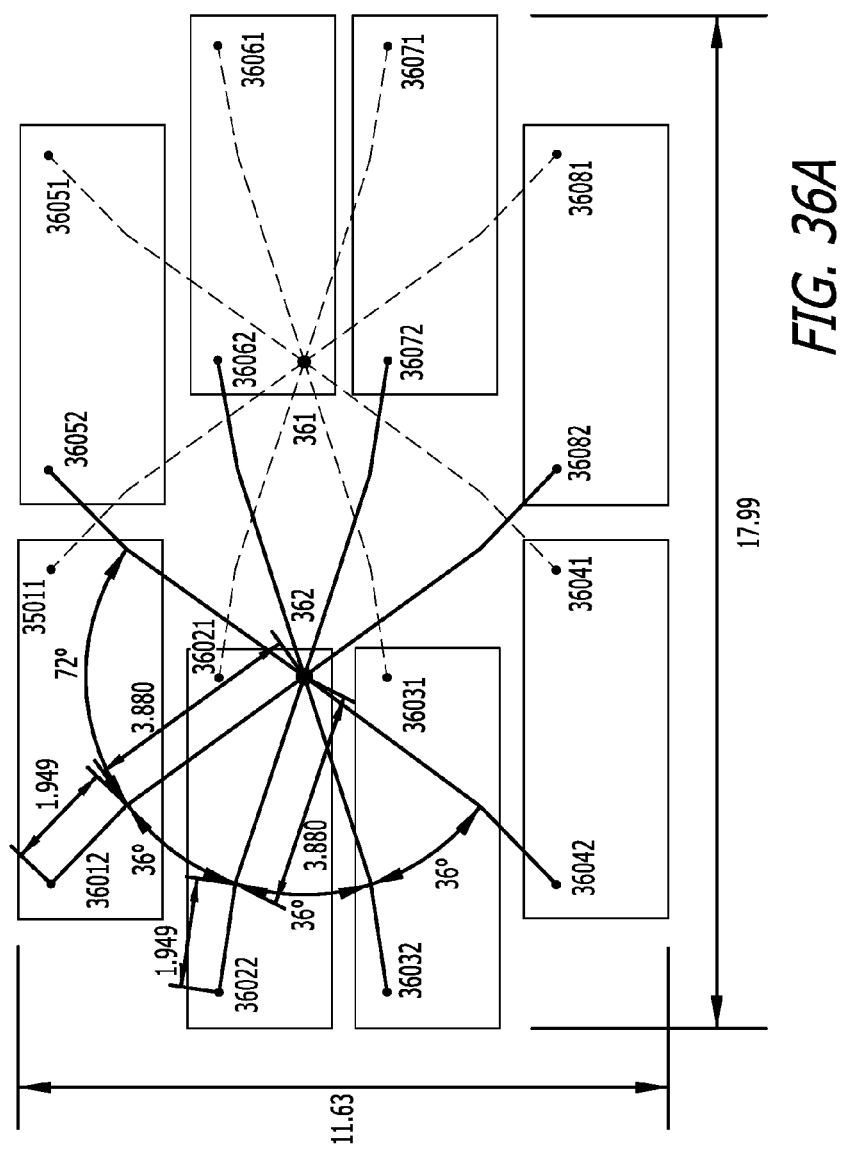
FIG. 36A illustrates another example of an input/output constellation arrangement of connectors in a (7+1)DSCU design that may connect to multiple PAUs with uniform angle separation between adjacent branches.
Figure 36B:
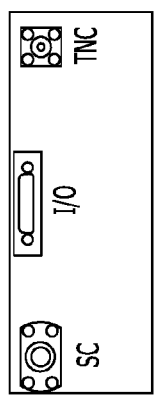
FIG. 36B illustrates an example of a PAU configured to slidably engage connectors on the DSCU illustrated in FIG. 36A.
Figure 36C:
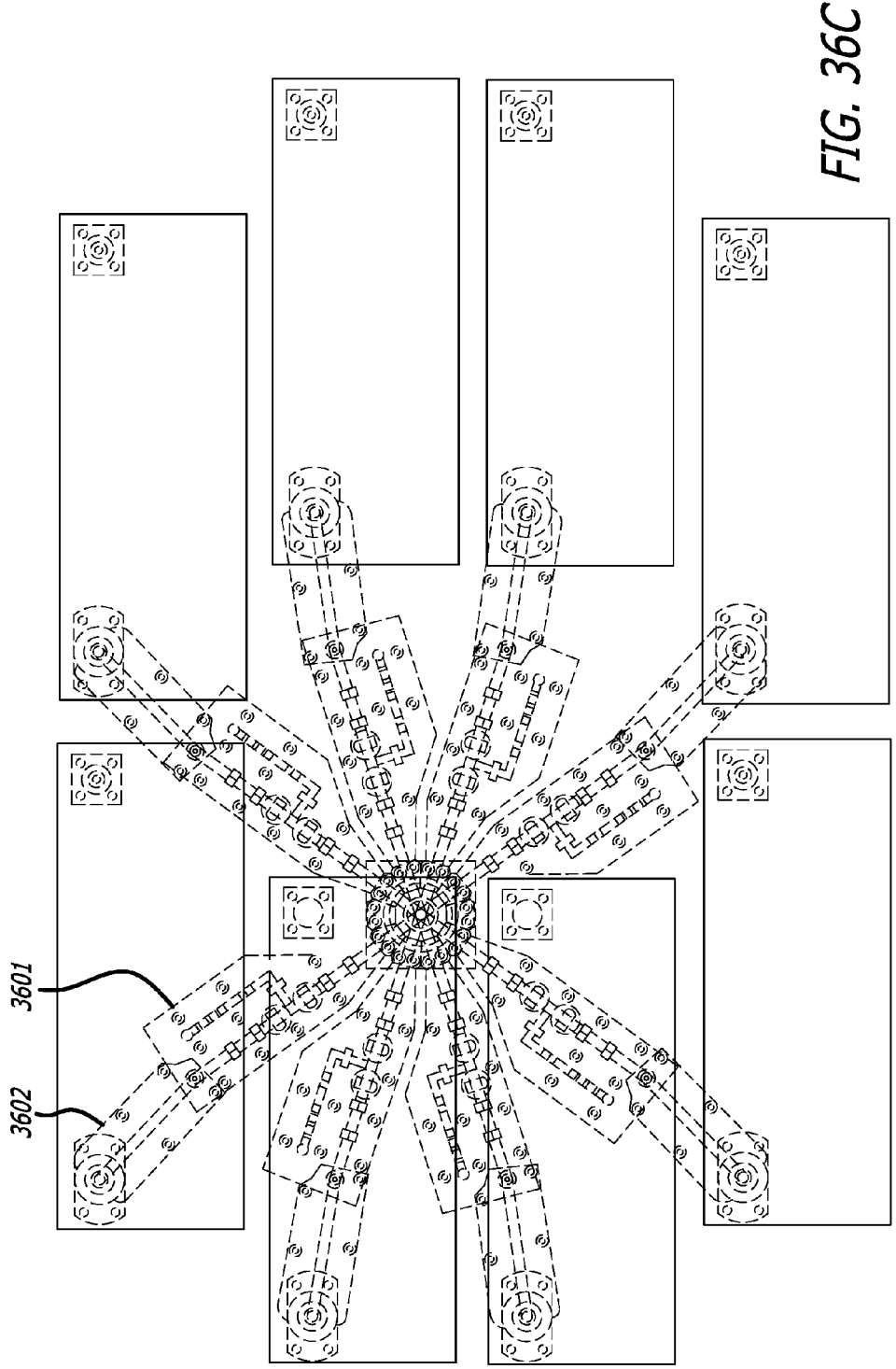
FIG. 36C illustrates an example of optimal layouts for the SCU portion of the DSCU illustrated in FIG. 36A utilizing the same assemblies for all branches.

FIG. 36A illustrates another example of an input/output constellation arrangement of connectors in a DSCU design that may connect to multiple PAUs with uniform angle separation between adjacent branches. FIG. 36B illustrates an example of a PAU configured to slidably engage connectors on the DSCU illustrated in FIG. 36A. In this optimal constellation arrangement, each branch in the SCU may travel the identical electrical paths, including a 3.88" line and a 1.949" line. The penetration approach follows the one in FIGS. 34 and 35. FIG. 36C illustrates the detailed circuit layout, including 8 identical switch assemblies and 8 transmission line assemblies for SCU.

As illustrated in FIG. 36A, there may be uniform RF sub-assembly arrangements with 36° separation between the adjacent branches using the same sub-assemblies as the ones for the SCU shown in FIG. 36C. The switch assemblies, such as a switch assembly 3601, may each have a 3.88" electrical length in the SCU and the switching PIN diodes may be located λ/4 away from the center of the SCU. The transmission line assemblies, such as a transmission line assembly 3602 may each have a 1.949" electrical length and may be laid-out using micro-strip line replacing cable in the DIV/SCU combo assembly.

Figure 37A:
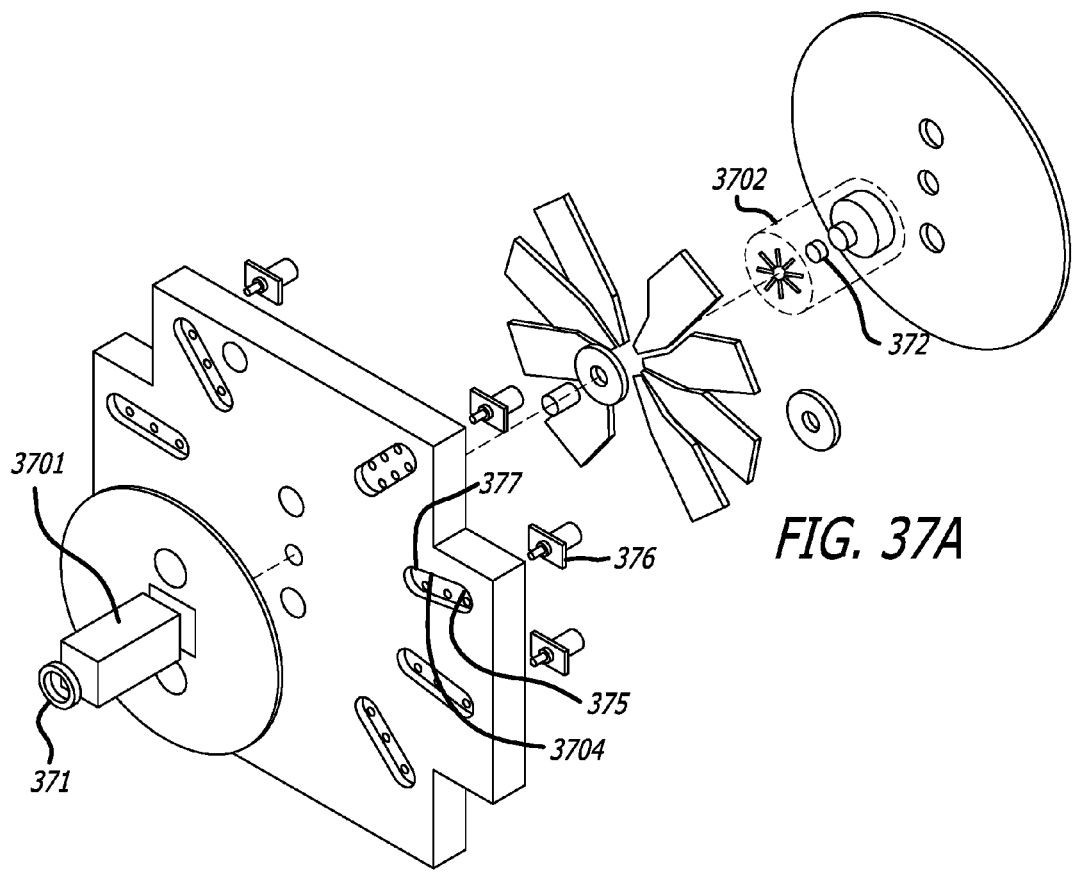
FIGS. 37A and 37B illustrate different views of an example of interface connections between a switching assembly and a transmission line assembly, and then to an interface of a PAU in an example of (7+1)DSCU.
Figure 37B:
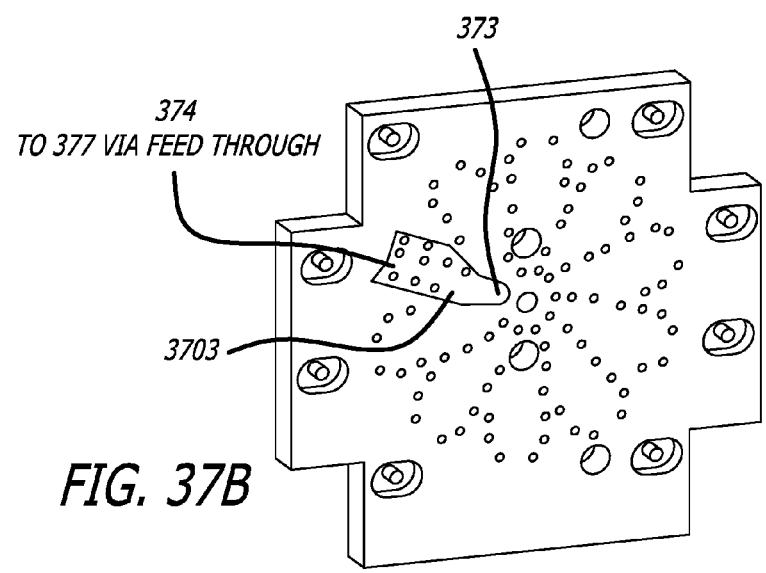

FIGS. 37A and 37B illustrate different views of an example of interface connections between a switching assembly and a transmission line assembly, and then to an interface of a PAU. These may be used in the cable-less DSCU illustrated in FIGS. 36A and 36C.

Figure 38A:
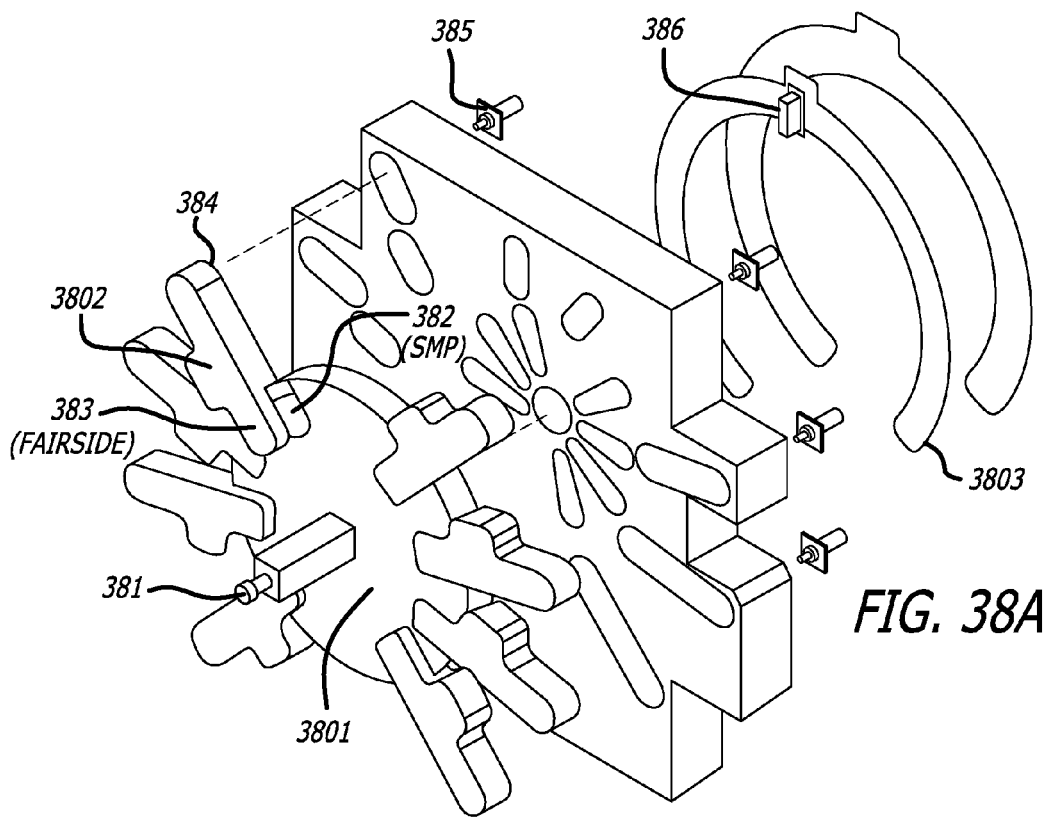
FIGS. 38A and 38B illustrate different views of an example of interface connections between a divider assembly and a switch assembly, and then to an interface of a PAU input in an example of (7+1)DSCU.
Figure 38B:
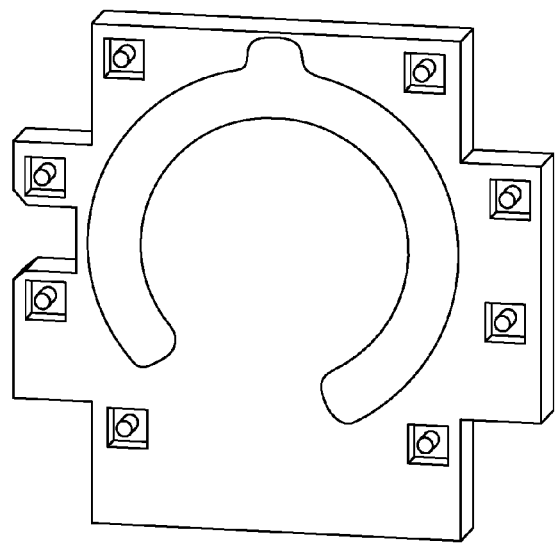

FIGS. 38A and 38B illustrate different views of an example of interface connections between a divider assembly and a switch assembly, and then to an interface of a PAU input.

FIGS. 39A and 39B illustrate different views of an example of a (7+1)DSCU design and a significant proportional profile reduction in comparison to the DIV/SCU combo assembly shown in FIG. 33. Both the DIV and SCU may be used in the cable-less DSCU illustrated in FIGS. 36A and 36C and may be based on the previous (9+1)SCU and 10-way DIV designs with two opposite branches being removed for the connector penetrations. TNC connector 391 is the input to DIV and 7/16 DIN connector 392 is the output of SCU. Pairs of 39011 and 39012, 39021 and 39022, 39031 and 39032, 39041 and 39042, 39051 and 39052, 39061 and 39062, 39071 and 39072, and 39081 and 39082 are to the 8 PAUs TNC inputs and SC output.

The drawings do not illustrate details of how to achieve a (7+1)SCU and 8-way DIV. They are similar to (9+1)SCU and 10-way DIV detailed previously with two opposite branches removed for penetrations, but rather illustrate how to channel the individual port to the surface of PAUs.

In FIG. 37, an output port 371 may be connected to a center point 372 of a spider pin assembly 3702 through a transformer assembly 3701. The spider pin assembly 3702 may include 8 output pins. One pin may connect a switch assembly 3703 at a port 373, while another port 374 may connect a transmission line assembly 3704 located on the other side via an RF feed through to a via hole 377. Then, an SC RF input connector 376 (from a PAU) may directly interface with the transmission line assembly 3704 at a junction 375. All other seven branches may be identically laid out following the same approach.

In FIG. 38, an 8-way divider 3801 may be produced by removing two opposite branches from the previous 10-way DIV. An RF signal input 381 may be divided between 8 output ports, such as an output port 382. An input 383 of the RF switch, such as an RF switch 3802, may be mated with the output port 382 via an SMP connection. Then, an output 384 of the switch can directly interface a TNC connector 385 on the far side.

Control signals may be input at a D-sub connector 386 and then routed to individual switches through an interface board 3803. FIGS. 38A and 38B also show an opening on the DIV/SW assembly for penetration of an SCU output port.

The (7+1)DSCU design shown in FIGS. 39A and 39B may be used to consolidate the device in FIGS. 37A and 37B with the device in FIGS. 38A and 38B. Compared to the DIV/SCU combo assembly design shown in FIG. 33, the DSCU design in FIG. 39 may have a dramatically decreased proportional volume. A common RF input at the TNC connector 391, RF output at the 7/16 DIN connector 392, SW control 393 on DIV, and SCU control ports 394 may be located on one side. Eight pairs of TNC/SC connectors (or barrels) may be located on the other side to directly interface with 8 PAUs.

Figure 40A:
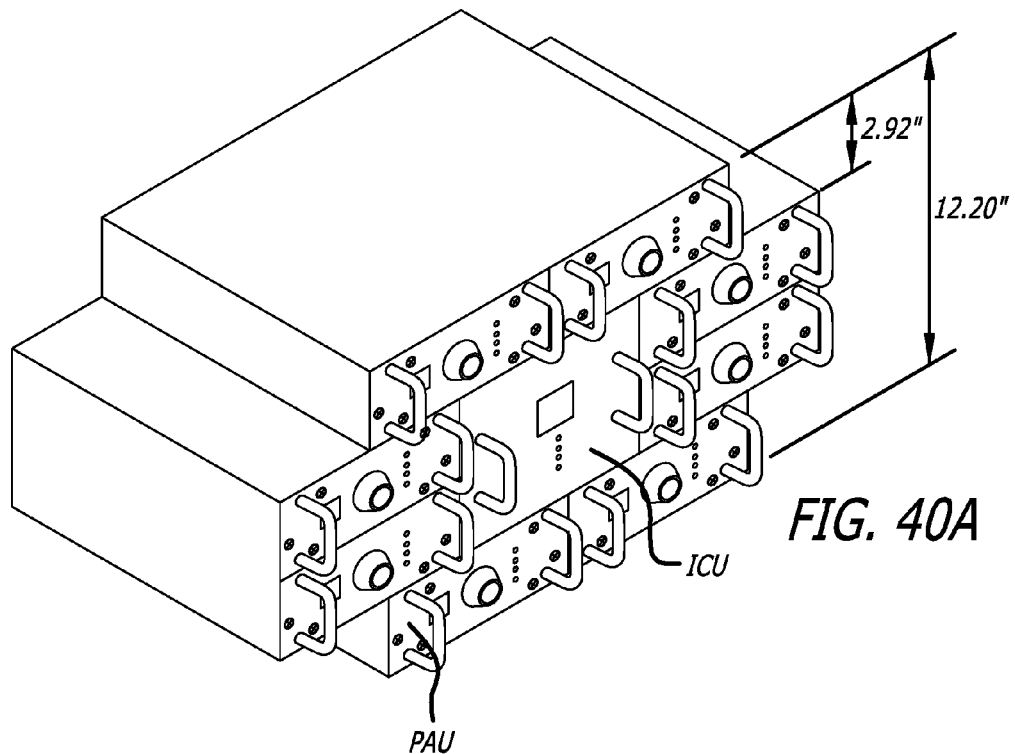
FIGS. 40A and 40B illustrate different views of an example of a 30 kW (7+1)CHPA utilizing a (7+1)DSCU for ultra-high power RF with a high power density.
Figure 40B:
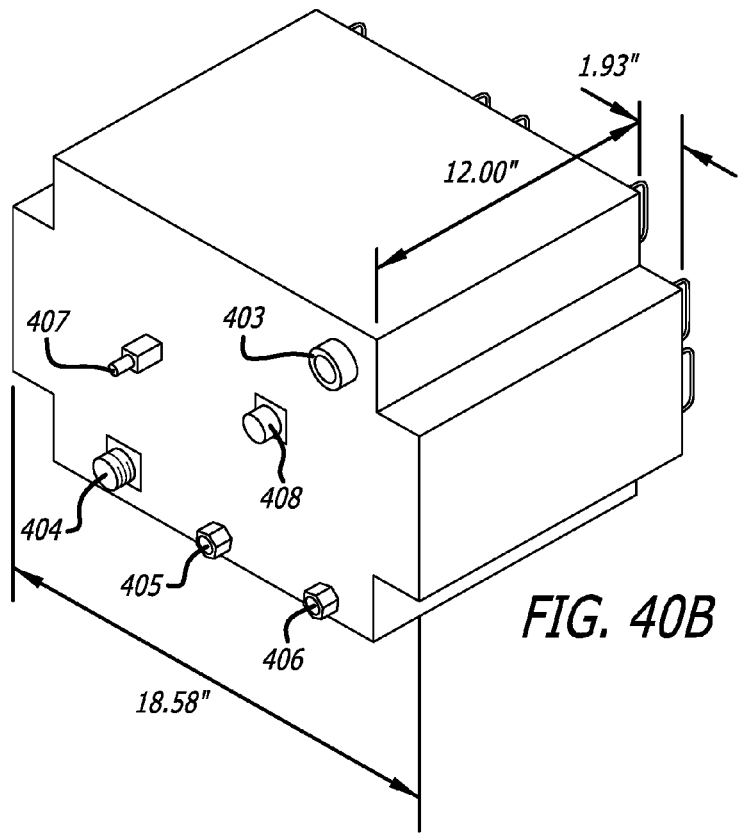

FIGS. 40A and 40B illustrate different views of an example of a 30 kW (7+1)CHPA utilizing a (7+1)DSCU for ultra-high power RF with a high power density. The self contained, ultra-high power amplifier module may receive an RF input signal at an input port 407 and deliver about 30 kW peak power at an output port 408. It may be powered by single 50 VDC from a connector 404 and monitored and controlled via signals at an Ethernet port 403. About 3.2 GPM of water may flow into an inlet 405, remove heat from the various LRUs, and then exit an outlet 406.

The disclosed (7+1)CHPA architecture may use a DSCU that places the ICU in the center surrounded by 8 PAUs. All of the LRUs may then be easily accessed for installation and maintenance. Reliable components may be located in the back of a card cage.

Compared to the previously-discussed 40 kW (9+1)CHPA design, the volume of 30 kW (7+1)CHPA may be significantly reduced proportionally. The power density may also be improved from 6.8 W/in$^3$ to 12 W/in$^3$, which represents a 76% power density improvement.

One or more of the various designs that have been discussed may provide one or more of the following features:

An (m+n) redundant CHPA architecture that includes an (m+n)SCU, (m+n) PAUs, and an (m+n)-way DIV. The (m+n) DIV may divide an input signal equally to (m+n) ports. "M" online PAUs may amplify their input signals into high power outputs with uniform amplitude and phase characteristics, while "n" offline PAUs may isolate their input signals from further propagating to the (m+n)SCU. "M" on ports of the SCU may coherently sum up "m" amplified signals, while "n" off ports may isolate any reflected signal back to "n" PAUs. When one of the "m" PAUs fails, one of the "n" PAUs in standby may fail over to replace the failed unit, the corresponding off port of SCU may be switched on, and the port interfacing the failed PAU may be shut off. The architecture may not allow a PAU failure to interrupt operation of CHPA. Only the DIV and the SCU may be in the RF critical path. These DIV and SCU designs may ensure a CHPA redundant architecture with high operation availability (e.g., about 99.99%) with an output reaching from 10 s to 100 s of kW.

The disclosed CHPA architecture may use an interface control unit (ICU) that communicates with a control module in the PAUs and controls the SCU accordingly. A PAU controller in each PAU may report the health conditions of the PAU, including DC, temperature, and RF parameters. When a key parameter of a PAU falls out of normal range, such as output power, the controller may quickly report the fault to the ICU. The ICU may automatically place the failed PAU offline and put one of the standby PAU's, if available, online, while turning on the correspondent input port of the SCU. Therefore, automatic fail over and uninterrupted operation may be achieved.

An RF switch may be placed before the RF input of a PAU and may be controlled by a positional switch. The DIV, PAUs, and SCU may interconnect with blind mate RF connectors and RF barrels may be inserted between PAUs and the DIV/SCU output/input ports (FIGS. 2 and 3). The blind mate connectors may facilitate easy removal and replacement of failed PAUs. This configuration may allow system maintenance without operational interruption. The RF switches and barrels may ensure good mechanical engagement of the RF interfaces when a PAU is "hot-swapped." At the same time, the architecture may prevent large harmful radiation, both when a PAU is present and removed, thereby facilitating safe operation.

The SCU design may provide both efficiency and graceful degradation. It may include high power RF switches to all input ports, among which "m" ports may be initially switched on and "n" ports may initially be switched off (FIG. 5). Thus, the SCU may provide redundancy in the combining scheme. When one of "m" PAU connected to the SCU ports fails, one of "n" ports, if available, can be placed into the 'on' position, so that the output impedance and power output of the SCU is unchanged. Even with (n+1) failed PAUs, the SCU may present m/(m−1) *50Ω, instead of 50Ω nominally with less than "n" failed PAUs. The larger the value of "m," the closer the SCU output impedance may be to 50Ω. For example, for m=9, the VSWR of SCU may be 1.125:1 when 8 ports are on. Therefore, the graceful degradation may be achieved with outstanding combining efficiency.

A high isolation passive DIV design with built-in terminations may divide the input signal uniformly and constantly no matter how output ports are matched (FIG. 7). Built-in terminators to each output port may independently absorb reflected signal from its corresponding port. Thus, the absorbed signal may not be superimposed onto other output ports.

The high-density SSHPA design (PAU) may reduce overall profile and increase overall power density. A T-plate structure may have three significant planes—two opposing horizontal on each of which are mounted power devices and one vertical plane that may interface to a cooling plate. The structure may double power density when compared to conventional layout architectures, minimizing power amplifier profile. High thermally conductive material may be embedded between the two horizontal surfaces which may effectively transfer heat onto the vertical surface to interface with the cooling plate. The approach may be used with any power amplifier (e.g., FIG. 9).

The liquid cooling system can further reduce the profile of the (m+n)CHPA and thus increase its power density. (FIG. 10).

A modular redundant (9+1)CHPA architecture (FIGS. 22 and 23) may deliver 40 kW peak power. Multiple (m+n) CHPAs may be conventionally combined to achieve 100 s of kW peak power in a scalable, solid state, coherent radar transmitter, while providing outstanding SSTx reliability and life cycle.

An (m+n) redundant power supply bank may be used with an (m+n)CHPA (FIG. 24). There may be the same number of PSUs as PAUs. All PSUs may initially be "on" with their DC outputs present at the PAUs. "M" PSUs may be initially "online" due to "m" "online" PAUs drawing currents; and "n" PSUs may be in standby due to "n" standby PSUs not drawing currents. When one of "online" PSUs fails, its controller may shut down the DC output to its corresponding PAU. One of "standby" PSU may then automatically fail-over due to its corresponding PAU being automatically placed "online." Therefore, automatic fail-over and uninterrupted operation of (m+n)PSB may be achieved via its (m+n)CHPA. Then, the MTBF of the PSU can be excluded from a MTBCF calculation of the system which may consist of one pair of (m+n)CHPA and (m+n)PSB. Thus, the (m+n)PSB architecture may not result in system availability (Ao) degradation. Graceful degradation with more than "n" PSU failures and hot-swapping may also be achieved in an (m+n)CHPA.

The PSB may instead be configured with (i+j) PSUs to form paralleling (i+j) redundancy (FIG. 25). In an (i+j) PSB architecture, all PSUs may initially be "on" and equally supply current to a common DC output to the CHPA. When one of the PSUs fails, the system may still operate normally with (i+j−1) PSUs supplying the needed current for the CHPA. The system may shut down with more than (i+j) PSU failures. This architecture may not provide graceful degradation due to PSU failures, but can support graceful degradation due to PAU failures. This configuration may allow the transmitter system to be designed with a small number of PSUs, providing a smaller profile and lower cost. However, the configuration may be subject to a common DC bus failure and be in the critical path, thus compromising MTBCF and Ao performance. A single DC "short" failure in any one of PAUs may bring down system operation. However, when power, power density, and reliability are equally important, this alternative configuration may provide an optimal trade-off. Therefore, to support an example 40 kW (9+1)CHPA, a (i+j)PSB, with i=2 and j=1, has been presented with 2.75 kW power supplies (FIG. 26).

Ultra-high power, such as 100 s kW SSTx, may be achieved by combining multiple CHPAs and PSBs utilizing the combining technology that has been disclosed. The disclosed SSTx scheme may provide unprecedented solid state power and reliability due to the high reliability of its major sub-assemblies, such as the CHPAs and PSBs. As an example, more than 280 kW SSTx may be achieved by combining 8 redundant (9+1)CHPAs utilizing hybrid combiners (FIG. 28).

A driver amplifier unit (DAU) (1+1) with automatic redundancy for SSTx may reduce system down time in the RF chain to a minimum (FIG. 28). Driver redundancy may include 2 DAUs and 2 RF switches, and RF switches to ensure uninterrupted operation with driver amplifier failures.

The modular design may provide hatch-ability for installation, maintenance, and when replacing an existing transmitter (FIGS. 28 and 29). This design may use an input driver divider module (IDDM), output combining module (OCM) and interface control module (ICM). Each module, with manageable dimensions and weight, can be integrated and tested independently, then transported through a navy ship's hatch (hatch-able) and integrated into the SSTx rack. The modular approach may make transmitter upgrades practical and may ease maintenance and increase system availability by reducing MTTR.

A retrofit upgrade proposal for SPS-49 radar transmitter has been disclosed (FIG. 31). The upgrade may occupy two bays and implement a full solid state transmitter using only two of the existing SPS-49 cabinet bays. This may leave a middle bay available for maintenance access.

A forward fit upgrade for the SPS-49 radar transmitter may use two 901D racks (FIG. 32). Each rack may house 4 CHPA/PSB assemblies.

A combined divider and switching combiner unit (DSCU) may provide an (m+n)-way divider and an (m+n)SCU. The DSCU module may eliminate all match cables from the DIV to the PAUs and from the PAUs to the SCU. Instead, direct interfaces with the PAUs may be provided. The (m+n) redundant CHPA may have a small profile (high power density), be easy to maintain, and provide consistent reliability and a significant cost savings.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

For example, the disclosed systems may achieve uninterrupted operation under pulse conditions, without missing a single pulse. However, some applications may not mind losing a pulse. In that case, the ICU may detect a fault condition in one of online PAUs and send a command to turn off an additional RF switch located at a significantly lower power level place where hot switching may not harm the added switch. Then, the PAU may fails over instantly, without concern for potential damage to SCU and PAUs. The described methodology may operate under CW conditions. The system may lose its signal for a period of 20 μS only, then continue operation. The disclosed power DIV may be used as a power combiner with coherent signal inputs to the multiple output ports; then the DIV input may serve as the output.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A cableless high power RF or microwave amplifier that amplifies an RF or microwave signal comprising:
   an input signal divider (DIV) that has a DIV input connector that receives the RF or microwave signal and that divides this input signal into multiple sub-input signals, each of which is delivered to a DIV output connector;
   multiple power amplifier units (PAUs), each of which has a PAU input connector that receives an RF or microwave signal and a PAU output connector that delivers an amplified version of the received RF or microwave signal; and
   an output signal switching combiner unit (SCU) that has multiple SCU input connectors and that coherently sums the signals at the multiple SCU input connectors and delivers this to an SCU output connector,
   wherein each of the PAU output connectors are electrically connected to a different one of the SCU input connectors without connecting cables, and
   wherein each of the PAU output connectors and each of the SCU input connectors are blind mate connectors.

2. The cableless high power RF or microwave amplifier of claim 1 wherein each of the DIV output connectors are connected to a different one of the PAU input connectors without connecting cables.

3. The cableless high power RF or microwave amplifier of claim 2 wherein each of the DIV output connectors and each of the PAU input connectors are blind mate connectors.

4. The cableless high power RF or microwave amplifier of claim 3 wherein the PAU input connector and the PAU output connector of each PAU both lie within the same plane.

5. The cableless high power RF or microwave amplifier of claim 4 wherein all of the DIV output connectors lie within the same plane.

6. The cableless high power RF or microwave amplifier of claim 5 wherein all of the SCU input connectors lie within the same plane.

7. The cableless high power RF or microwave amplifier of claim 6 wherein all of the DIV output connectors and all of the SCU input connectors lie in the same plane.

8. The cableless high power RF or microwave amplifier of claim 1 wherein all of the DIV output connectors and all of the SCU input connectors lie in the same plane.

9. The cableless high power RF or microwave amplifier of claim 1 wherein all of the DIV output connectors are equidistant from a central point.

10. The cableless high power RF or microwave amplifier of claim 1 wherein all of the SCU input connectors are equidistant from a central point.

11. The consolidated power divider and combiner of claim 10 wherein all of the DIV output connectors are equidistant from a central point that is at a different location than the central point from which all of the SCU input connectors are equidistant.

12. The cableless high power RF or microwave amplifier of claim 1 wherein the DIV and SCU are in a common housing.

13. The cableless high power RF or microwave amplifier of claim 2 further comprising, for each PAU:
   an electronic switch between the DIV output connector that is connected to the PAU and the PAU input connector to which the DIV output connector is connected; and
   a sense switch that causes the electronic switch to open when the PAU is removed from the high power RF or microwave amplifier, but before any electrical connection to the PAU is broken.

14. The cableless high power RF or microwave amplifier of claim 1 wherein:
   each of the PAUs is contained with a PAU housing and each of the PAU output connectors is attached to a wall of the housing of its PAU; and
   the SCU is contained within an SCU housing and each of the SCU input connectors is attached to a wall of the SCU housing.

* * * * *